(12) United States Patent
Deng et al.

(10) Patent No.: US 10,421,971 B2
(45) Date of Patent: Sep. 24, 2019

(54) ANTI-TUMOR THERAPY

(71) Applicant: The University of Chicago, Chicago, IL (US)

(72) Inventors: Liufu Deng, Chicago, IL (US); Yang-xin Fu, Chicago, IL (US); Nikolai Khodarev, Chicago, IL (US); Ralph Weichselbaum, Chicago, IL (US)

( * ) Notice: Subject to any disclaimer, the term of this patent is extended or adjusted under 35 U.S.C. 154(b) by 0 days.

(21) Appl. No.: 15/109,945

(22) PCT Filed: Oct. 24, 2014

(86) PCT No.: PCT/US2014/062228
§ 371 (c)(1),
(2) Date: Jul. 6, 2016

(87) PCT Pub. No.: WO2015/108595
PCT Pub. Date: Jul. 23, 2015

(65) Prior Publication Data
US 2016/0333355 A1    Nov. 17, 2016

Related U.S. Application Data

(60) Provisional application No. 61/927,838, filed on Jan. 15, 2014.

(51) Int. Cl.
*A61K 31/713* (2006.01)
*C12N 15/113* (2010.01)
*A61K 45/06* (2006.01)
*A61K 31/7084* (2006.01)
*A61K 31/7088* (2006.01)
*A61K 41/00* (2006.01)
*A61N 5/10* (2006.01)

(52) U.S. Cl.
CPC ...... *C12N 15/1138* (2013.01); *A61K 31/7084* (2013.01); *A61K 31/7088* (2013.01); *A61K 31/713* (2013.01); *A61K 41/0038* (2013.01); *A61K 45/06* (2013.01); *A61N 5/1077* (2013.01); *A61N 2005/1021* (2013.01); *A61N 2005/1098* (2013.01); *C12N 2310/14* (2013.01); *C12N 2320/30* (2013.01); *C12N 2320/31* (2013.01)

(58) Field of Classification Search
None
See application file for complete search history.

(56) References Cited

U.S. PATENT DOCUMENTS

| 6,331,396 B1 | 12/2001 | Silverman et al. |
| 2006/0052323 A1* | 3/2006 | Gilchrest ........... A61K 31/7088 514/44 R |
| 2011/0229560 A1 | 9/2011 | Wang et al. |
| 2013/0039933 A1* | 2/2013 | Barber ................... A61K 45/06 424/185.1 |
| 2016/0046943 A1* | 2/2016 | Pyle ..................... A61K 38/212 424/85.6 |
| 2016/0222387 A1* | 8/2016 | Khodarev ............ C12N 15/113 |

FOREIGN PATENT DOCUMENTS

WO    2012050884 A    4/2012

OTHER PUBLICATIONS

Yoshino et al (Blood 2013 122:4721) (Year: 2013).*
Le et al (Radiotherapy and Oncology 90 (2009) 273-279) (Year: 2009).*
Widau, et al. "RIG-1-like receptor LGP2 Protects Tumor Cells from Ionizing Radiation" Proceedings of the National Academy of Sciences, Jan. 13, 2014 (Jan. 13, 2014) vol. 111, No. 4 pp. E484-E491.
International Search Report and Written Opinion of the International Searching Authority issued in PCT Application No. PCT/US2014/062228, dated Feb. 4, 2015, 11 pages.

* cited by examiner

*Primary Examiner* — Catherine S Hibbert
(74) *Attorney, Agent, or Firm* — McDonnell Boehnen Hulbert & Berghoff LLP

(57) ABSTRACT

Compositions, kits and methods for treating cancer in a subject in need thereof are disclosed involving one or more genes the suppression of which renders the cancer chemosensitive and/or radiosensitive.

18 Claims, 28 Drawing Sheets

Specification includes a Sequence Listing.

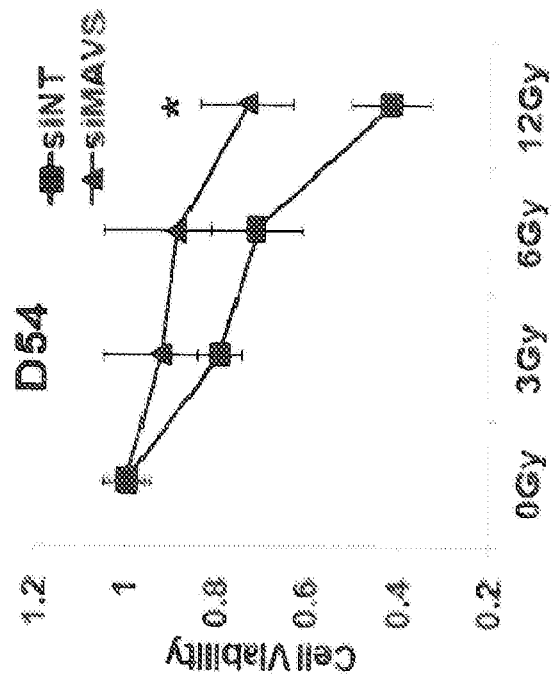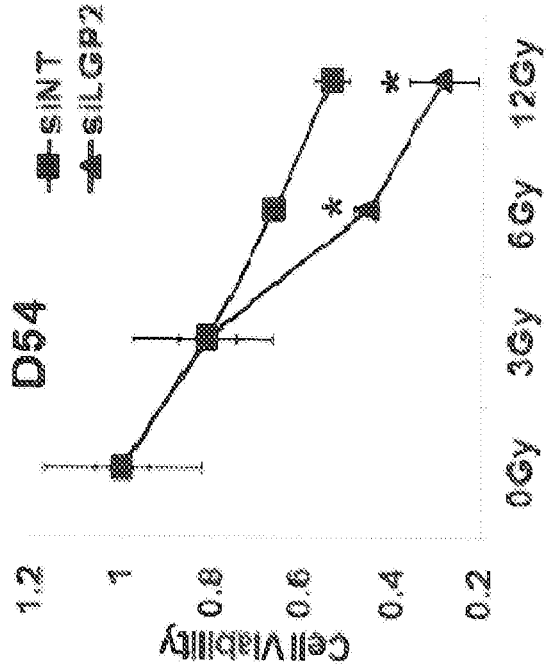
FIG. 15A
FIG. 15B

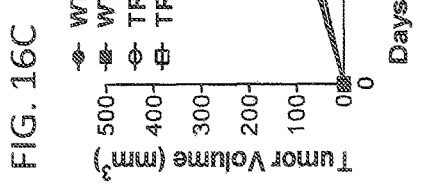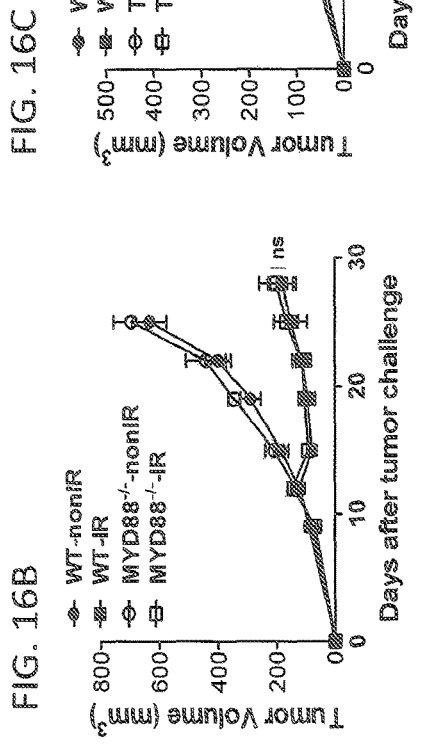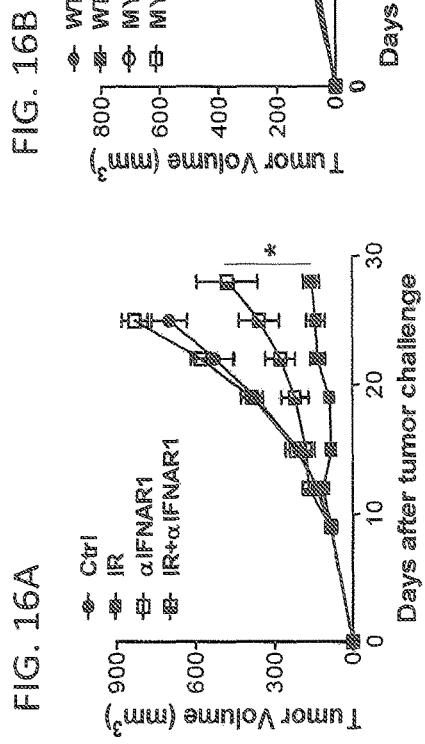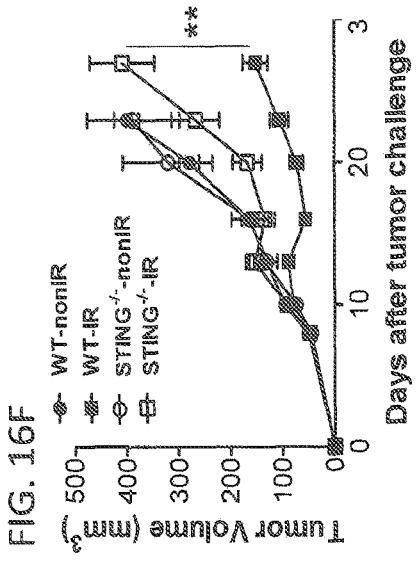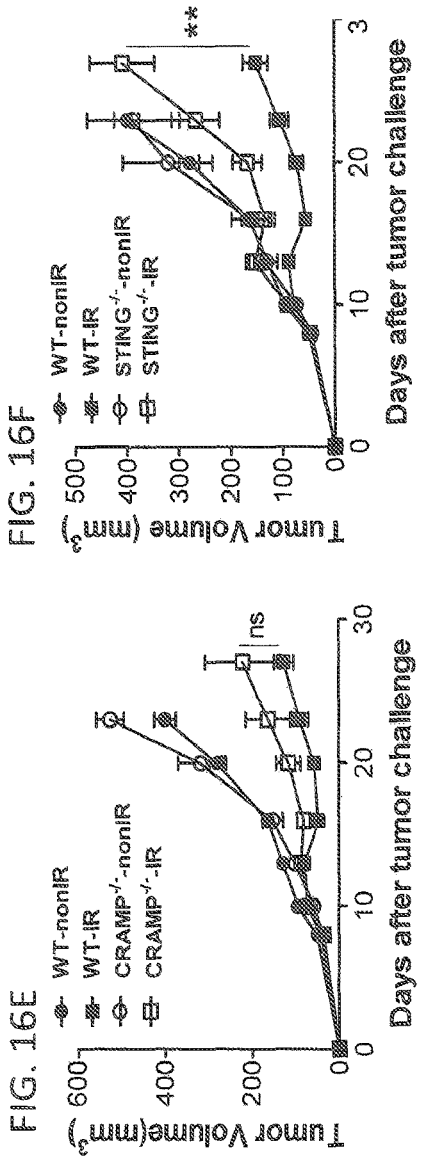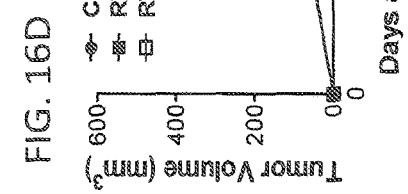
FIG. 16A  FIG. 16B  FIG. 16C
FIG. 16D  FIG. 16E  FIG. 16F

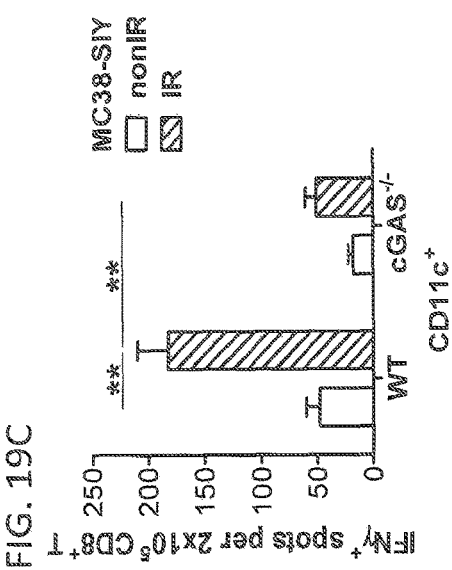
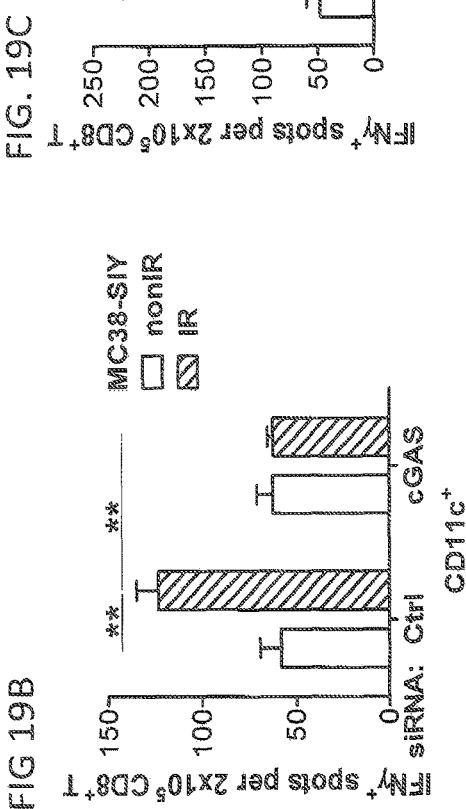
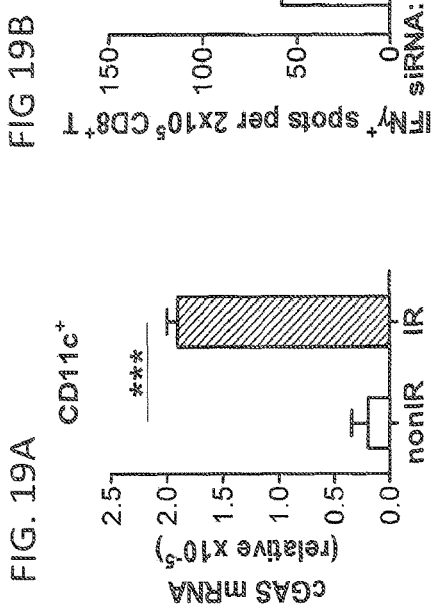
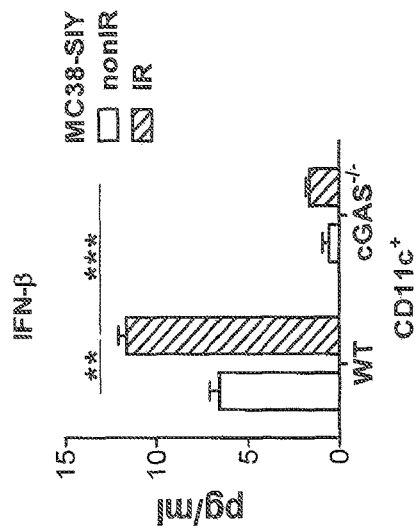
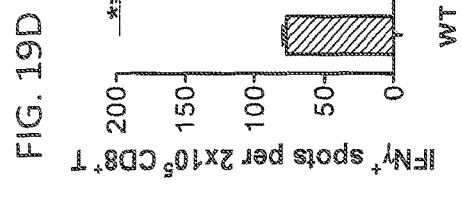

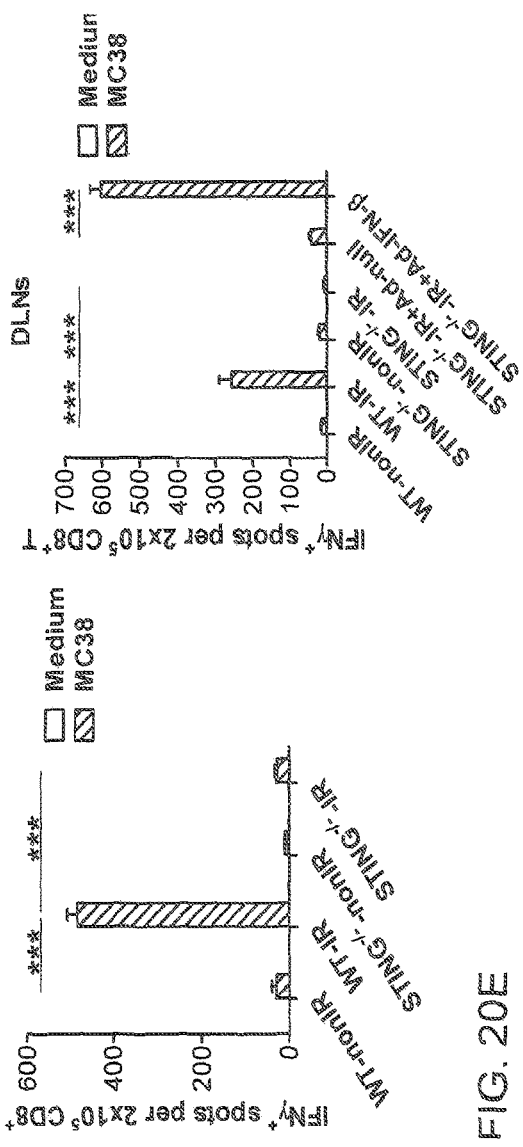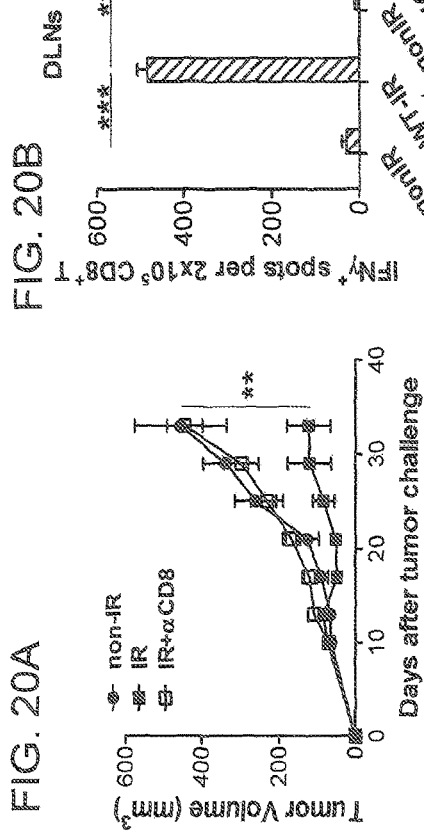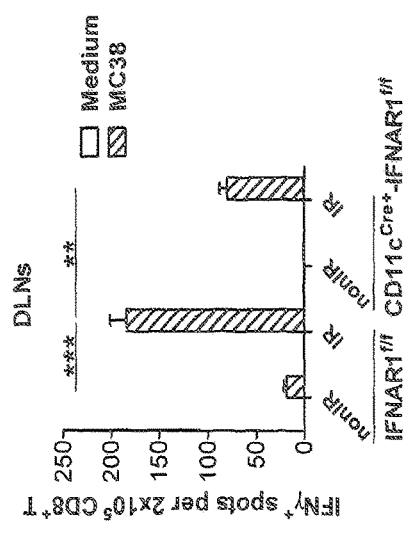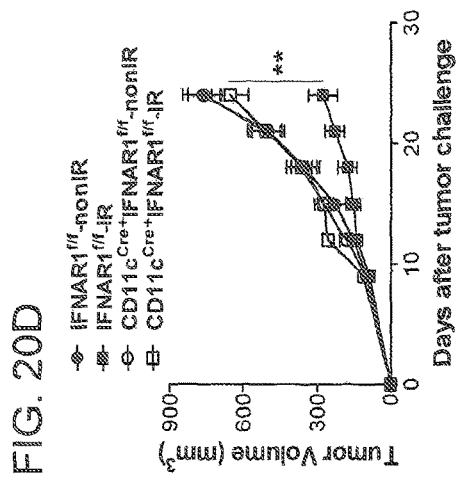
FIGS. 20 A-E

ANTI-TUMOR THERAPY

CROSS REFERENCE TO RELATED APPLICATIONS

This application represents the U.S. National Stage of International Application No. PCT/US2014/062228, filed Oct. 24, 2014, which is based on, claims priority to, and incorporates herein by reference in its entirety, U.S. Provisional Patent Application Ser. No. 61/927,838, filed Jan. 15, 2014, and entitled, "ANTI-TUMOR THERAPY."

STATEMENT CONCERNING GOVERNMENT INTEREST

Not applicable

BACKGROUND OF THE INVENTION

1. Field of the Invention

The present invention relates to the identification and control of gene targets for treatment of cancers, including chemoresistant and/or radioresistant cancers.

2. Description of the Background of the Invention

Cancer is not fully understood on a molecular level and remains a leading cause of death worldwide. One of the deadliest forms of cancer is solid tumors. One such solid tumor is lung cancer, the most common cancer worldwide and the leading cause of cancer-related death in the United States. Approximately 219,000 new diagnoses and over 159,000 deaths from lung cancer occur annually in the United States. Approximately 85% of lung cancers are non-small cell histology (NSCLC), including lung adenocarcinomas, which are the most common lung cancer type in the U.S. Treatment of early and intermediate stage NSCLC usually involves surgery, stereotactic radiotherapy, or conventional radiotherapy with or without adjuvant chemotherapy. Chemotherapy regimens for lung cancer, either concurrent with radiotherapy (RT) or adjuvant to surgery, usually incorporate platinum-based drugs such as cisplatin or carboplatin, as this has been shown to confer a survival advantage when either combined with radiotherapy or in the adjuvant setting.

Standard fractionated radiotherapy as the primary treatment for NSCLC is reserved for patients with tumors too advanced to resect, who are medically unstable, whose disease has spread beyond the chest, or in the case of small or metastatic tumor hypofractionated stereotacktic body radiotherapy. The utility of postoperative radiotherapy is controversial and subsets of patients who are likely to benefit have been proposed. These include patients with advanced lymph node metastases (N2-N3 or extra-capsular extension) and close or positive surgical margins. However, clear clinical and/or molecular selection criteria for patients who may benefit from postoperative radiotherapy remains elusive. No prognostic or predictive signature to select patients with NSCLC who may benefit from radiotherapy or chemotherapy is consistently used in clinical practice at this time.

The activity of Jak/Stat dependent genes has been shown to predict the outcome of patients with lung cancer and their response to the adjuvant radiotherapy or chemotherapy. Stat1 (Signal Transducer and Activator of Transcription 1) is a member of the Stat family of proteins, which are mediators of Jak signaling. Stat1 is phosphorylated at the tyrosine 701 position by Jak kinases and translocates to the nucleus to activate the transcription of hundreds of Interferon-Stimulated Genes (ISGs).

Further, clinical trials of Jak/Stat pathway inhibitors in hematological malignancies are ongoing for the pharmacological suppression of the Stat-related pathways. Jak inhibitors currently available include either specific inhibitors of Jak2 or combined inhibitors of Jak1 and Jak2. The radiosensitizing effects of the Jak2 inhibitor TG101209 (TargeGen Inc., CAS 936091-14-4) were recently described in two lung cancer cell lines and were associated with suppression of the Stat3 pathway. TG101209 was developed to potentially inhibit myeloproliferative disorder-associated JAK2V617F and MPLW515L/K mutations. Activation of Jak2/Stat3 signaling was demonstrated in several other lung cancer cell lines and was associated with increased oncogenic potential, tumor angiogenesis, and EGFR signaling associated with progression of lung adenocarcinomas. Further, next-generation sequencing recently revealed constitutively active Jak2 mutation (V617F) in some lung cancer patients.

To date, few publications describe the application of these drugs in lung cancer models, and mechanisms of their action in lung cancer are still poorly understood. The majority of publications regarding the application of Jak inhibitors in solid tumors, including lung cancer, explain their action based on pathways activated by Stat3, Stat5 or not directly related to Stat signaling. Jak/Stat1 pathways in solid tumors are not described in the context of therapeutic effects of Jak inhibitors, though they are already described in some myelodysplastic diseases. It is believed that Jak1 kinase is activated by Jak2 kinase and both are necessary for activation of Stat1 and Stat3. It is also believed that Stat1 and Stat3 can form heterodimers with transcriptional activity. Additionally, genes induced by Jak2/Stat3 activation overlap with IFN/Stat1-dependent genes. Finally, constitutively active oncogenic Jak2 (Jak2V617F) induces genes overlapping with the Stat1-dependent genes.

While the importance of Jak/Stat signaling, in general, for cancers continues to be investigated, the role that downstream effector genes may play in tumors remains undefined. Consequently, there is an urgent and definite need to identify the downstream effector genes that may potentially have a role in tumor development associated with activation of the Jak/Stat pathway. Such genes may provide new targets for Jak-related therapy of cancers, including, for example, lung cancer, or for sensitization of cancers for chemotherapies and/or radiotherapies. Therefore, there is a need to determine the identities of downstream effector genes in the Jak/Stat pathway of cancer, including solid tumors, that may play a role in treating cancers, and to develop effective cancer therapies around these downstream effector genes. More effective and targeted cancer therapies with potentially fewer side effects are also needed.

SUMMARY OF THE INVENTION

According to a first aspect, a method of treating cancer in a subject in need thereof in provided by regulation of endogenous IFNbeta (IFNβ) production in the subject by, for example: 1) suppressing in a therapeutically effective amount at least one of a product or expression of an Interferon-Stimulated Gene (ISG) in the subject; 2) inducing a therapeutically effective amount of activation of Type I Interferon in the subject; 3) maintaining in a therapeutically effective amount activation of Type I Interferon in the subject; and/or 4) maintaining radio/chemoprotection of normal non-disease state tissue in the subject by suppressing in a therapeutically effective amount at least one of: i) a primary RNA or DNA sensor; ii) a major adaptor protein of a RNA/DNA-dependent pathway of IFN production; and/or iii) up-regulation or activation or gene transfer of two apical repressors of a RNA/DNA-dependent pathway of IFN production. The method may also include administering to the subject a therapeutic amount of ionizing radiation.

In one embodiment, the method includes suppressing the product or the expression of the Interferon-Stimulated Gene (ISG).

In yet another embodiment, the Interferon-Stimulated Gene (ISG) includes at least one RIG1-like receptor (RLR) family member.

In another embodiment, ionizing radiation induced cytotoxic IFNβ production is substantially maintained in the subject at levels substantially found prior to the administration of the ionizing radiation.

In yet another embodiment, Mitochondrial Antiviral Signaling Protein (MAVS)-dependent induction of endogenous IFNβ production is maintained in the subject at substantially the same level found in the subject prior to the administration of the ionizing radiation.

In other embodiments, the RIG1-like receptor (RLR) family member includes, for example, RIG1 (Retinoic Acid-inducible Gene 1), LGP2 (Laboratory of Genetics and Physiology 2), and/or MDA5 (Melanoma Differentiation-Associated Protein 5).

In further embodiments, suppressing of the Interferon-Stimulated Gene (ISG) results in suppression of growth or proliferation of the cancer, cell death of the cancer, and/or sensitization of the cancer to the ionizing radiation and/or chemotherapy.

In another embodiment, suppressing production of the Interferon-Stimulated Gene includes the suppression of expression of at least one Cytoplasmic Pattern-recognition Receptor (PRR) protein, including, for example, RIG1, LGP2, and/or MDA5.

In still other embodiments, the method of treating cancer includes maintaining activation of Type I Interferon in a subject to maintain ionizing radiation and chemotherapy sensitization in the subject.

In yet other embodiments, the method includes administering to a subject a therapeutic amount of an agent that maintains activation of Type I Interferon in the subject.

In one embodiment, the agent includes at least one of a shRNA, a siRNA, a micro-RNA mimic, an antisense oligonucleotide, a chemical, and a protein inhibitor.

In another embodiment, the agent down-regulates cytoplasmic DNA-sensoring pathway-exonuclease TREX1 (Three Prime Repair Exonuclease 1).

In yet another embodiment, the agent up-regulates at least one of DAI (DNA-dependent Activator of IFN regulatory factors), IFI16 (Gamma-interferon-inducible protein Ifi-16), and Aim2 (Interferon-inducible protein AIM2).

In another embodiment, the primary RNA or DNA sensor includes at least one of RIG1, MDA5, DAI, IFI16, Aim2, and cGAS.

In one embodiment, the major adaptor protein of the RNA/DNA-dependent pathway of IFN production includes MAVS and/or STING.

In yet another embodiment, the two apical repressors of the RNA/DNA-dependent pathway of IFN production include LGP2 and/or TREX1.

In another embodiment, ionizing radiation includes brachytherapy, external beam radiation therapy, or radiation from cesium, iridium, iodine, and/or cobalt.

In still another embodiment, the method of treating cancer includes inducing Type I Interferon production in a subject to maintain ionizing radiation and chemotherapy sensitization in the subject.

In one embodiment, the method includes administering to a subject a therapeutic amount of an agent that induces the Type 1 Interferon production in the subject.

In yet another embodiment, the agent enhances STING signaling.

In another embodiment, the agent increases cGAS levels in a subject, and in yet another embodiment, the agent enhances expression of a cGAS gene in a cancerous cell in the subject.

In another embodiment, the agent is cGAMP.

In still another embodiment, the agent activates at least one endosomal toll-like receptor (TRL) including, for example, TLR3, TLR7, TLR8 and TLR9.

In one embodiment, the agent interacts with at least one adaptor protein that includes at least one of myeloid differentiation primary-response protein 88 (MyD88) and TIR-domain-containing adaptor protein inducing IFN-β (TRIF).

In another embodiment, the agent is administered to a subject that increases levels of cGAS in a cancerous cell.

In yet another embodiment, the cGAS levels are greater than about 100% of a cancerous-state control cell.

In still another embodiment, the agent is delivered to a cancerous cell by a pharmaceutical carrier, including, for example, a nanocarrier, a conjugate, a nucleic-acid-lipid particle, a vesicle, a exosome, a protein capsid, a liposome, a dendrimer, a lipoplex, a micelle, a virosome, a virus like particle, a nucleic acid complexes, and combinations thereof.

In yet another embodiment, the agent is delivered into the cytosol of a dendritic cell.

In another aspect, a pharmaceutical composition for treating cancer in a subject in need thereof is provided that includes a therapeutically effective amount of an agent that regulates endogenous IFNbeta (IFNβ) production in the subject.

In another aspect, a pharmaceutical composition for treating cancer in a subject in need thereof is provided that includes a therapeutically effective amount of an agent that induces a therapeutically effective amount of activation of Type I Interferon in the subject;

In one embodiment, the agent suppresses at least one of a product or the expression of an Interferon-Stimulated Gene (ISG) in the subject.

In yet another embodiment, the agent maintains activation of Type I Interferon in the subject.

In another embodiment, a pharmaceutical composition includes an agent that maintains radio/chemoprotection of normal non-disease state tissue in a subject by suppression of at least one of: i) a primary RNA or DNA sensor, ii) a major adaptor protein of a RNA/DNA-dependent pathway of IFN production, and iii) up-regulation or activation or gene transfer of two apical repressors of a RNA/DNA-dependent pathway of IFN production.

In still another embodiment, a pharmaceutical composition may contain one or more optional pharmaceutically acceptable carriers, diluents and excipients.

In yet another embodiment, a pharmaceutical composition includes an agent that suppresses at least one of the product or the expression of the Interferon-Stimulated Gene (ISG), which may include, for example, at least one RIG1-like receptor (RLR) family member.

In another embodiment, a pharmaceutical composition includes an agent maintains activation of Type I Interferon and includes at least one of a shRNA, a siRNA, a microRNA mimic, an antisense oligonucleotide, a chemical, and a protein inhibitor.

In yet another embodiment, a pharmaceutical composition includes an agent that down-regulates a cytoplasmic DNA-sensing pathway-exonuclease TREX1 (Three Prime Repair Exonuclease 1).

In another embodiment, a pharmaceutical composition includes an agent that down-regulates a suppressor of cytoplasmic RNA-sensing pathway-LGP2.

In yet another embodiment, a pharmaceutical composition includes an agent that up-regulates at least one of DAI (DNA-dependent Activator of IFN regulatory factors), IFI16 (Gamma-interferon-inducible protein Ifi-16), and Aim2 (Interferon-inducible protein AIM2).

In one embodiment, the pharmaceutical composition may also include a therapeutically effective amount of at least one antineoplastic agent and/or a radiotherapy agent.

In yet another embodiment, a pharmaceutical composition includes an agent that induces Type I Interferon production in the subject.

In another embodiment, a pharmaceutical composition includes an agent that enhances STING signaling.

In still another embodiment, a pharmaceutical composition includes an agent that increases cGAS levels in the subject.

In yet another embodiment, a pharmaceutical composition includes an agent that enhances expression of a cGAS gene in a cancerous cell in the subject.

In another embodiment, a pharmaceutical composition includes cGAMP.

In one embodiment, a pharmaceutical composition includes an agent that activates at least one endosomal toll-like receptor (TLR), including at least one of TLR3, TLR7, TLR8 and TLR9.

In yet another embodiment, a pharmaceutical composition includes an agent that increases level of cGAS in a cancerous cell, and in one embodiment cGAS levels are equal to or greater than about 100% of a cancerous state control cell.

In another embodiment, a pharmaceutical composition includes an agent that is delivered to the cancerous cell by a pharmaceutical carrier.

In still another embodiment, a pharmaceutical composition includes a pharmaceutical carrier that includes at least one of a nanocarrier, a conjugate, a nucleic-acid-lipid particle, a vesicle, an exosome, a protein capsid, a liposome, a dendrimer, a lipoplex, a micelle, a virosome, a virus like particle, and a nucleic acid complexes.

In yet another embodiment, a pharmaceutical composition includes an agent that is delivered into a cytosol of a dendritic cell.

In another aspect, a method of protecting normal non-disease state tissue from genotoxic stress is provided that includes suppressing in the tissue at least one of a product or the expression of an Interferon-Stimulated Gene in a therapeutically effective amount.

In one embodiment, suppressing production of the Interferon-Stimulated Gene includes administering to a tissue a neutralizing antibody to IFNβ or an antagonist of Type I IFN receptor (IFNAR1).

In yet another embodiment, administration of a neutralizing antibody or an antagonist substantially prevents cytotoxic effects of LGP2 depletion in the tissue.

In another embodiment, genotoxic stress includes exposure of a tissue to ionizing radiation, ultraviolet light, chemotherapy, and/or a ROS (Reactive Oxygen Species).

In one embodiment, a tissue is from a subject diagnosed with a cancer and the normal non-disease state tissue is substantially free of the cancer.

In yet another embodiment, a subject is a human.

In yet another aspect, a prognostic kit for use with a tissue having a high grade glioma is provided that includes at least one set of primers for QRT-PCR detection of LGP2 to determine expression levels of LGP2 in the tissue.

In one embodiment, high expression levels of LGP2 and low expression levels of LGP2 predicts improved prognosis in treating a high grade glioma.

In yet another embodiment, tissue is from brain tissue of a human subject.

In another embodiment, high expression levels of LGP2 are at least about 1.5 fold greater than an expression level of LGP2 in a normal non-disease state tissue of a human subject.

In yet another embodiment, low expression levels of LGP2 are at least about 1.5 fold less than an expression level of LGP2 in a normal non-disease state tissue of a human subject.

In still another embodiment, a prognostic kit may include at least one of a reagent for purification of total RNA from a tissue, a set of reagents for a QRT-PCR reaction, and a positive control for detection of LGP2 mRNA.

BRIEF DESCRIPTION OF THE FIGURES

FIG. 2A: Graphical representation of flow cytometric data in WiDr cells that were collected 48 h post-IR treatment. FIG. 2B: Quantification of flow cytometric experiments in D54, WiDr and Scc61 cells collected 48 h post-IR treatment. The data are represented as fold-change relative to siNT at 0 Gy. FIG. 2C and FIG. 2D: Clonogenic survival curves in D54 (FIG. 2C) and Scc61 (FIG. 2D) cells transiently transfected with siNT or siLGP2 and irradiated at 0, 3, 5 or 7 Gy. Data are represented in a semi-log scale. Western blots are representative of siRNA mediated knockdown of LGP2. In all experiments, data are presented as mean values of at least three independent measurements; error bars are standard deviations and significance was assessed using two-tailed t-test (* indicates p<0.05);

FIG. 3A: Crystal violet staining of survived colonies 12 days after irradiation of cells, transfected with Flag (upper panel) or LGP2 (lower panel). FIG. 3B: Quantification of survival fraction of mock-transfected and LGP-transfected cells (see Methods). Representative Western blot of stable Flag and LGP2 clone is inserted into panel B;

FIG. 5A: Radiation-induced expression of IFNβ mRNA. IFNβ expression in D54, WiDr, SCC61 and HEK293 cells treated with or without 6 Gy IR was measured by qRT-PCR and normalized to GAPDH expression. Data are expressed as fold-change relative to non-irradiated cells. FIG. 5B: Radiation-induced activation of IFNβ promoter. HEK293 cells were transiently co-transfected with pGL3-Ifnβ and pRL-SV40. Firefly luciferase was normalized to Renilla luciferase and is expressed relative to non-irradiated cells at each collection time. FIG. 5C: Type I IFN receptor (IFNAR1) is needed for cytotoxicity induced by IR. Wild type (Wt) and IFNAR1$^{-/-}$ MEFs were treated with the indicated doses of IR and collected 96 h post-IR. Viability was determined by methylene blue staining and extraction, followed by spectrophotometric quantification. Viability is shown relative to non-irradiated control cells. Data are represented as mean with standard deviation for assays performed in at least triplicates;

FIG. 6A: LGP2 suppresses IR-induced activation of IFNβ promoter. HEK293 cells were stably transduced with shRNA directed to LGP2 or non-targeting control (shNT). Cells were transfected with pGL3-Ifnβ and pRL-SV40, irradiated (indicated dose) and collected 72 h after IR. Firefly luciferase activity was normalized to Renilla luciferase activity and is expressed relative to non-irradiated cells. FIG. 6B: Neutralizing antibodies to IFNβ prevent cytotoxic effects of LGP2 depletion. D54 cells were depleted of LGP2 with siRNA (see FIG. 2C) and irradiated at 0, 3 or 6 Gy in the presence or absence of neutralizing antibody to IFNβ (1 µg/mL). Cell viability was assessed 96 h post-IR using methylene blue assay. Data are normalized to non-targeting siRNA at 0 Gy and represented as mean with error bars showing standard deviation for assays performed at least in triplicate. Significance was measured using two-tailed t-test (*p<0.05);

FIG. 7A: Expression of Interferon-Stimulated genes (ISGs) and LGP2 in the Phillips database (n=77). Yellow represents up-regulated and blue-down-regulated genes. Rows correspond to patients while columns correspond to individual genes in IRDS signature. FIG. 7B: Kaplan-Meier survival of LGP2-high (LGP2+) and LGP2-low (LGP2−) patients from Phillips database. FIG. 7C: Expression of ISGs and LGP2 in the TCGA database (n=382) and (FIG. 7D) Survival of LGP2+ and LGP2− patients in CGA database. p-values represent Cox proportional hazards test;

FIGS. 15A, 15B, 15C and 15D show that suppression of LGP2 in D54 and SCC61 leads to radiosensitization, while suppression of MAVS- to radioprotection_of cells.

FIGS. 16A, 16B, 16C, 16D, 16E, and 16F show STING signaling providing an antitumor effect of radiation. MC38 tumors in WT mice and KO mice were treated locally one dose of 20 Gy ionizing radiation (IR) or untreated. FIG. 16A: The antitumor effect of radiation was compromised by neutralization of type I IFNs. 500 µg anti-IFNAR was administered intratumorally on day 0 and 2 after radiation. FIG. 16B: MyD88 was non-essential for the antitumor effect of radiation. The tumor growth was shown in WT and MyD88$^{-/-}$ mice after radiation. FIG. 16C: TRIF was dispensable for the antitumor effect of radiation. The tumor growth was shown in WT and TRIF$^{-/-}$ mice after radiation. FIG. 16D: HMGB-1 was unnecessary for the antitumor effect of radiation. 200 µg anti-HMGB1 was administered i.p. on day 0 and 3 after radiation. FIG. 16E: CRAMP is dispensable for the antitumor effect of radiation. The tumor growth was shown in WT and CRAMP$^{-/-}$ mice after radiation. FIG. 16F: STING was required for the antitumor effect of radiation. The tumor growth was shown in WT and STING$^{-/-}$ mice after radiation. Representative data are shown from three (FIGS. 16A, 16B, 16C, 16D, 16E and 16F) experiments conducted with 5 (FIGS. 16A, 16B, 16C, and 16D) or 6 to 8 (FIGS. 16E and 16F) mice per group. Data are represented as mean±SEM. *P<0.05, **P<0.01 and $^{ns}$ No significant difference (Student's t test);

FIGS. 17A and 17B: STING signaling mediated the induction of IFN-β and CXCL10 by radiation. Tumors were excised on day 3 after radiation and homogenized in PBS with protease inhibitor. After homogenization, Triton X-100 was added to obtain lysates. ELISA assay was performed to detect IFN-β (FIG. 17A) and CXCL10 (FIG. 17B). FIG. 17C: STING signaling mediated the induction of type I IFN in dendritic cells after radiation. 72 hours after radiation, the single cell suspensions from tumors in WT mice and STING$^{-/-}$ mice were sorted into CD11c$^+$ and CD45$^-$ populations. IFN-β mRNA level in different cell subsets were quantified by real-time PCR assay. Representative data are shown from three experiments conducted with 4 mice per group. Data are represented as mean±SEM. *P<0.05, P<0.01 and *P<0.001 (Student's t test);

FIGS. 18A, 18B, and 18C: BMDCs were cultured with 40 Gy-pretreated MC38-SIY$^{hi}$ in the presence of fresh GM-CSF for 8 hours. Subsequently purified CD11c$^+$ cells were co-cultured with isolated CD8$^+$ T cells from naive 2 C mice for three days and analyzed by ELISPOT assays. FIG. 18A: STING amplifying DCs function with the stimulation of irradiated-tumor cells. FIG. 18B: The deficiency of IRF3 impaired DC function with the stimulation of irradiated-tumor cells. FIG. 18C: IFN-β treatment rescued the function of STING$^{-/-}$DCs. 10 ng/ml IFN-β was added into the co-culture of BMDC and irradiated-tumor cells as described above. FIG. 18D: STING signaling mediated the induction of IFN-β in DCs by irradiated-tumor cells. Isolated CD11c$^+$ cells as described above were incubated for additional 48 h and the supernatants were collected for ELISA assay. Representative data are shown from three (FIGS. 18A, 18B, 18C, and 18D) experiments. Data are represented as mean±SEM. *P<0.05, P<0.01, *P<0.001 and $^{ns}$ No significant difference (Student's t test). See also FIG. 23;

FIGS. 19A, 19B, 19C, 19D, and 19E show cGAS role in dendritic cell sensing of irradiated-tumor cells. FIG. 19A: The mRNA level of cGAS in tumor-infiltrating CD11c$^+$ was elevated after radiation. CD11c$^+$ population was sorted from tumors at 72 hour after radiation. Real-time PCR assay was performed to quantify the mRNA level of cGAS. FIGS. 19B, 19C, and 19D: ELISPOT assays were performed as described in FIG. 18A. FIG. 19B: The function of BMDCs was compromised when cGAS was silenced. BMDCs were transfected with siRNA-non-targeting control and siRNA-cGAS. Two days later after transfection, the BMDCs were harvested for the co-culture assay. FIG. 19C: cGAS$^{-/-}$ DCs stimulated with irradiated-tumor cells failed to cross-prime CD8$^+$ T cells. FIG. 19D: DMXAA and IFN-β rescued the function of cGAS$^{-/-}$DCs. 10 ng/ml IFN-β was added into the co-culture of BMDC and irradiated-tumor cells as described above. The isolated CD11c$^+$ cells were incubated with 100 g/ml DMXAA for additional three hours. FIG. 19E: cGAS signaling mediated the induction of IFN-β in DCs by irradiated-tumor cells stimulation. Representative data are shown from three (FIGS. 19A, 19B, 19C, 19D and 19E) experiments. Data are represented as mean±SEM. P<0.01 and *P<0.001 (Student's t test). See also FIG. 24;

FIGS. 20A, 20B, 20C, 20D and 20E show that STING signaling provides for effective adaptive immune responses mediated by type I IFN signaling on DCs after radiation. FIG. 20A: CD8$^+$ T cells were required for the antitumor effects of radiation. 300 μg anti-CD8 mAb was administered i.p. every three days for a total of four times starting from the day of radiation. FIG. 20B: The function of tumor-specific CD8$^+$ T cells was dependent on STING signaling following radiation. Eight days after radiation, tumor draining inguinal lymph nodes (DLNs) were removed from WT and STING$^{-/-}$ mice. CD8$^+$ T cells were purified and incubated with mIFN-γ pre-treated MC38 at the ratio of 10:1 for 48 hours and measured by ELISPOT assays. FIG. 20C: Exogenous IFN-β treatment rescued the function of CD8$^+$ T cells in STING$^{-/-}$ mice after radiation. 1×10$^{10}$ viral particles of Ad-null or Ad-IFN-β was administered intratumorally on day 2 after radiation. Tumor DLNs were removed as described in (FIG. 20B). FIG. 20D: Anti-tumor effect of radiation was dependent on type I IFN signaling on dendritic cells. The tumor growth curve was analyzed in CD11c-Cre$^+$ IFNAR$^{f/f}$ and IFNAR$^{f/f}$ after radiation. FIG. 20E: The CD8$^+$ T cell response was impaired in CD11c-Cre+IFNAR$^{f/f}$ mice after radiation. Tumor DLNs were removed as described in (FIG. 20B). Representative data are shown from three (FIGS. 20A, 20B, 20C, 20D, and 20E) experiments conducted with 5-6 (FIGS. 20A and 20D) or 3-4 (FIGS. 20B and 20C and 20E) mice per group. Data are represented as mean±SEM. P<0.01 and *P<0.001 (Student's t test);

FIGS. 21A and 21B: The administration of cGAMP enhanced the antitumor effect of radiation. MC38 tumors in WT and STING$^{-/-}$ mice were treated by one dose of 20 Gy. 10 μg 2'3'-cGAMP was administered intratumorally on day 2 and 6 after radiation. Tumor volume (FIG. 21A) and tumor-bearing mice frequency after IR (FIG. 21B) were monitored. FIG. 21C: cGAMP synergized with radiation to enhance tumor-specific CD8$^+$ T cell response. 10 μg 2'3'-cGAMP was administered intratumorally on day 2 after radiation. Tumor DLNs were removed on day 8 after radiation for ELISPOT assays as described in FIG. 5B. FIG. 21D: The synergy of cGAMP and radiation is dependent on STING. ELISPOT assay was conducted as described in FIG. 5B. Representative data are shown from three experiments conducted with 5-7 (FIGS. 21A and 21B) or 3-4 (FIGS. 21C and 21D) mice per group. Data are represented as mean±SEM. P<0.01 and *P<0.001 (Student's t test in FIGS. 21A, 21C and 21D, and log rank (Mantel-Cox) test in FIG. 21B);

FIG. 24A: The floating DNA fragments were inessential for the ability of BMDCs to cross-priming of CD8$^+$ T cells. 10 μg/ml DNase I was added in the incubation of BMDC and irradiated-MC38-SIY. The cross-priming of CD8+ T cells assay was performed. FIG. 24B: Cell-to-cell contact was responsible for the function of BMDCs with the stimulation of irradiated-tumor cells. Irradiated-MC38-SIY tumor cells were added into the insert and BMDCs were added into the well of Transwell-6 well Permeable plates with 0.4 μm pore size. Eight hours later, BMDCs were harvested and then incubated with CD8+ T cells for three days. Representative data are shown from three experiments. Data are represented as mean±SEM. $^{ns}$ No significant difference (Student's t test).

DESCRIPTION

Figure 1:
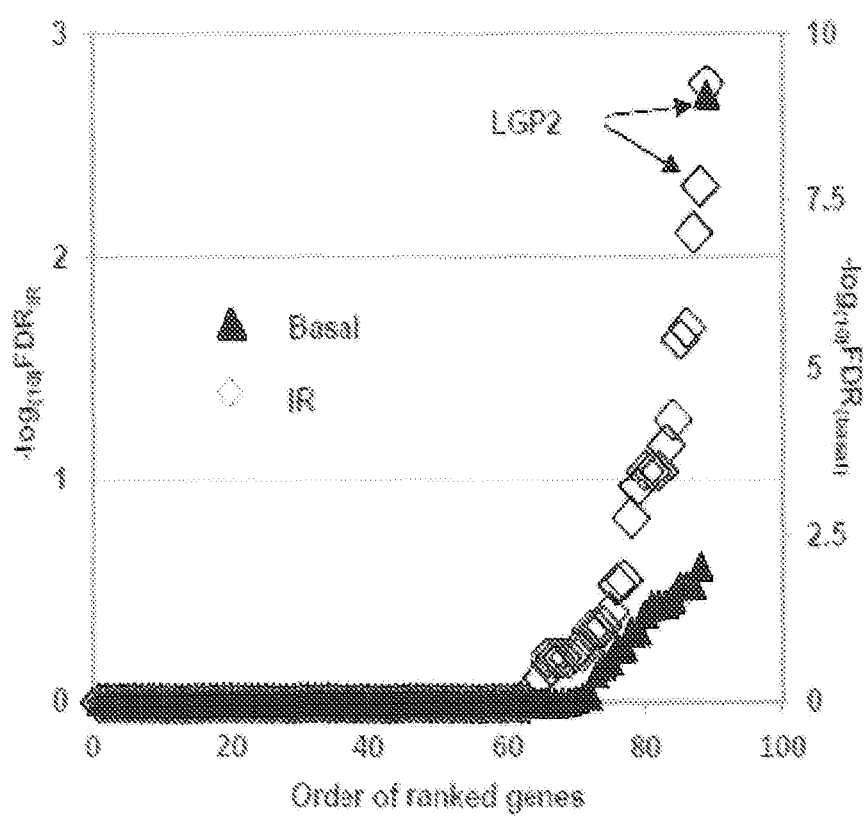
FIG. 1 shows the identification of LGP2 as pro-survival ISG. In each cell line tested 89 screened genes were ranked according to the ability of corresponding siRNAs to suppress cell viability as measured by CellTiter-Glo® luminescent assay (Promega, Madison, Wis.). FDR-corrected significance values for each gene across all tested cell lines were estimated by rank aggregation approach (see Methods). Data are presented as negative log-transformed false discovery ratios (FDR) for each gene on the basal level (closed triangles, right Y-axis) and 48 hours after irradiation at 3 Gy (open diamonds, left Y axis)

Treatment of a cancer in a subject in need thereof is provided herein, as are compositions, kits, and methods for treating cancer, and methods for identifying effector genes in the Jak/Stat pathway having a role in the treatment of cancer and therapies to treat cancer based on these effector genes. Such treatment of cancer may include maintaining ionizing radiation and/or chemotherapy sensitization of a tissue in the subject, maintaining radio/chemoprotection of normal non-disease state tissue in the subject, and/or protecting normal non-disease state tissue from genotoxic stress. A Jak/Stat dependent cancer may include any solid tumor, including lung, prostate, head and neck, breast and colorectal cancer, melanomas and gliomas, and the like. While the present disclosure may be embodied in different forms, several specific embodiments are discussed herein with the understanding that the present disclosure is to be considered only an exemplification and is not intended to limit the invention to the illustrated embodiments.

Radiotherapy used alone or in combination with surgery or chemotherapy is employed to treat primary and metastatic tumors in approximately 50-60% of all cancer patients. The biological responses of tumors to radiation have been demonstrated to involve DNA damage, modulation of signal transduction, and alteration of the inflammatory tumor microenvironment. Indeed, radiotherapy has been recently shown to induce antitumor adaptive immunity, leading to tumor control (Apetoh, L., Ghiringhelli, F., Tesniere, A., Obeid, M., Ortiz, C., Criollo, A., Mignot, G., Maiuri, M. C., Ullrich, E., Saulnier, P., et al. (2007). Toll-like receptor 4-dependent contribution of the immune system to anticancer chemotherapy and radiotherapy. Nat Med 13, 1050-1059; Lee, Y., Auh, S. L., Wang, Y., Burnette, B., Meng, Y., Beckett, M., Sharma, R., Chin, R., Tu, T., Weichselbaum, R. R., and Fu, Y. X. (2009). Therapeutic effects of ablative radiation on local tumor require CD8+ T cells: changing strategies for cancer treatment. Blood 114, 589-595). The blockade of immune checkpoints has been shown to improve the efficacy of radiotherapy on local and distant tumors in experimental systems and more recently in clinical observations (Deng, L., Liang, H., Burnette, B., Beckett, M., Darga, T., Weichselbaum, R. R., and Fu, Y. X. (2014). Irradiation and anti-PD-L1 treatment synergistically promote antitumor immunity in mice. J Clin Invest 124, 687-695; Postow, M. A., Callahan, M. K., Barker, C. A., Yamada, Y., Yuan, J., Kitano, S., Mu, Z., Rasalan, T., Adamow, M., Ritter, E., et al. (2012). Immunologic correlates of the abscopal effect in a patient with melanoma. N Engl J Med 366, 925-931). Furthermore, radiotherapy sculpts innate immune response in a type I IFNs-dependent manner to facilitate adaptive immune response (Burnette, B. C., Liang, H., Lee, Y., Chlewicki, L., Khodarev, N. N., Weichselbaum, R. R., Fu, Y. X., and Auh, S. L. (2011). The efficacy of radiotherapy relies upon induction of type i interferon-dependent innate and adaptive immunity. Cancer Res 71, 2488-2496). However, the molecular mechanism for host type I IFNs induction following local radiation had not yet been defined. We have also previously demonstrated that overexpression of Stat1-pathway plays an important role in the response of tumor cells to ionizing radiation (IR), though mechanisms were unclear.

Radiotherapy is the most common modality of the antitumor treatment and is used in the majority of known tumors as either the means to reduce initial tumor volume or adjuvant treatment to reduce chances of local or distant recurrence after primary surgical excision of the tumor. Often in the post-surgery treatment chemotherapy is prescribed but the outcome of the chemotherapy-treated patients does not exceed 5% success over not-treated patients. It is now believed that downstream effector genes in the Jak/Stat pathway have a causal role in treatment-resistant cancers, including solid tumors, and if downstream effector genes can be identified having a direct relationship to treatment resistance, new therapies could be developed for treatment resistant cancers.

We have now discovered that the Rig-I-like receptor (RLR) LGP2 is a potent regulator of tumor cell survival. It is believed that LGP2 suppresses the RNA-activated cytoplasmic RLR pathway and inhibits the mitochondrial antiviral signaling protein (MAVS)-dependent induction of endogenous IFNbeta (IFNβ) production. It is further believed that suppression of LGP2 leads to enhanced IFN-beta expression resulting in increased tumor cell killing, while suppression of MAVS leads to protection of tumor cells from ionizing radiation-induced killing. Neutralizing antibodies to IFNbeta protect tumor cells from the cytotoxic effects of IR.

Consistent with this observation, mouse embryonic fibroblasts (MEFs) from IFNalpha Receptor I knock-out mice (IFNAR1$^{-/-}$) are radioresistant compared to wild-type MEFs. In high grade gliomas, where survival rates correlate with response to radiotherapy, elevated levels of LGP2 expression are associated with poor clinical outcomes. It is contemplated that these results demonstrate that the cellular response to radiation occurs through RLR-dependent pathways of the innate immune response to pathogens converging on the induction of IFNbeta.

We also demonstrate that another cytoplasmic DNA sensing pathway responsible for activation of Type I Interferons also contain members, which suppression can lead to radioprotection or radiosensitization. Apical suppressor of cytoplasmic DNA-sensing pathway-exonuclease TREX1 protect cells from IR and its down-regulation by shRNA (small hairpin RNA) renders SCC61 cells radiosensitive. Contrary to this suppression of adapter protein STING, responsible for DNA-dependent activation of Type I IFNs, render cells radioresistant. This connection we have discovered reveals novel pathways by which IR causes cellular cytotoxicity and identifies previously unrecognized targets to enhance tumor cell killing by radio/chemotherapy or protect normal tissues from genotoxic stress.

Maintaining Type I IFN production can be achieved, for example, by suppression of negative regulators of RNA and DNA dependent pathways as LGP2 and TREX1. Activation of Type I IFN production can be measured by means known in the art, including, for example, QRT-PCR, or hybridization of mRNA with specific probes on custom arrays or commercial arrays available from, for example, Affymetrix Inc., Agilent Technologies, Inc., Nanostring Technologies, Inc., GeneQuant (GE Healthcare, Little Chalfont, United Kingdom) or Luminex Corp., or using protein detection by ELISA.

While the bane of radiotherapy (IR) of cancer is the emergence of radioresistant cells, we have also discovered that radioresistance is induced by LGP2, a resident RIG-I like receptor protein also known as RNA helicase DHX58. IR induces interferon and stimulates accumulation of LGP2. In turn LGP2 shuts off the synthesis of interferon and blocks its cytotoxic effects. Ectopic expression of LGP2 enhances resistance to IR whereas depletion enhances cytotoxic effects of IR. Herein we show that LGP2 is associated with radioresistance in numerous diverse cancer cell lines. Examination of available databases links expression of LGP2 with poor prognosis in cancer patients.

From our observations, we contemplate that cytoplasmic pattern-recognition receptors (PRRs) are also potent targets for radio/chemosensitization of tumor cells or protection of normal cells from genotoxic stress, including, for example, exposure to IR, ultraviolet light (UV), chemotherapy, and/or ROS (Reactive Oxygen Species). We further contemplate from our observations that the pathway of Type I IFN production is a target for radio/chemosensitization or protection. Further, it is believed that RIG1-like receptors (RLRs), including RIG1 (Retinoic Acid-inducible Gene 1), LGP2, MDA5 and other molecules of this type, are responsible for activation of IFN response through interaction with cytoplasmic RNA, and are targets for radio/chemosensitization or protection. It is further contemplated that MAVS (also known as IPS1 (Interferon-beta Promoter Stimulator 1)) are an effector protein of RNA-dependent pathway of IFN production and are a target for normal tissues radioprotection or (through activation) tumor radio/chemosensitization. We further contemplate that cytoplasmic DNA sensors and regulatory molecules like TREX1, DAI, IFI16, Aim2 and other molecules of this type as targets for radio/chemosensitization or protection; and STING or TMEM173 or MPYS (plasma membrane tetraspanner) (a.k.a. MITA or ERIS) as target for normal tissues radio/chemoprotection or through activation-tumor radio/chemosensitization. Further, a method where tumor radio/chemosensitization may be achieved by suppression of the apical repressors of the RNA/DNA-dependent pathways of IFN production are further contemplated herein as is a method where normal tissue radio/chemoprotection may be achieved by suppression of the major effector proteins of the RNA/DNA-dependent pathways of IFN production. A further method where protection of normal tissues from toxic effects of IR and chemotherapy may be achieved by depletion of IFNs (e.g., with neutralizing Abs) or agonists of IFNAR1 (interferon-alpha receptor 1) (e.g., such as with an antagonist of IFNAR1), is also contemplated as are prognostic markers for patients with high grade gliomas where high expression of LGP2 predicts poor prognosis while low expression of LGP2 predicts improved prognosis.

In another aspect of the present disclosure, we now demonstrate that STING, but not MyD88, provides for type I IFN-dependent antitumor effects of radiation. As shown herein, STING in dendritic cells (DCs) controlled radiation-mediated IFN-β induction and were activated by irradiated-tumor cells. The cytosolic DNA sensor cyclic GMP-AMP synthase (cGAS) mediated DCs sensing of irradiated-tumor cells. Moreover, STING provided for radiation-induced adaptive immune responses, which relied on type I IFN signaling on DCs. Exogenous IFN-β treatment rescued cGAS/STING-deficient immune responses. Accordingly, enhancing STING signaling by cGAMP administration promoted antitumor efficacy of radiation. Our results reveal that the molecular mechanism of radiation-mediated antitumor immunity depends on a proper cytosolic DNA-sensing pathway, pointing towards a new understanding of radiation and host interactions. Furthermore, we uncover herein a new strategy to improve radiotherapy by cGAMP treatment. For example, it is contemplated that administration of a therapeutic amount of 2'3'-Cgamp (InvivoGen; cyclic [G(2',5') pA(3',5')p]); CAS 1441190-66-4), and/or one or more therapeutically active derivatives or mimics thereof, to a subject in need thereof promotes antitumor efficacy of radiation therapy as compared to an untreated control subject. For example, cGAMP can be formulated for injection via intravenous, intramuscular, sub-cutaneous, intratumoral, and/or intraperitoneal routes. Typically, for a human adult (weighing approximately 70 kilograms), an effective amount or therapeutically effective amount can be administered by those skilled in the art. For example, a subject is administered from about 0.01 mg to about 3000 mg (including all values and ranges there between), or from about 5 mg to about 1000 mg (including all values and ranges there between), or from about 10 mg to about 100 mg (including all values and ranges there between). A dose may be administered on an as needed basis or every 1, 2, 3, 4, 5, 6, 7, 8, 9, 10, 11, 12, 18, or 24 hours (or any range drivable therein) or 1, 2, 3, 4, 5, 6, 7, 8, 9, or 10 times per day (or any range derivable therein). The subject may be treated for 1, 2, 3, 4, 5, 6, 7, 8, 9, 10 or more days (or any range derivable therein) or until tumor has disappeared or been reduced. cGAMP can be administered 1, 2, 3, 4, 5, 6, 7, 8, 9, or more times. It is also contemplated that other agents that enhance STING signaling may also be utilized in the therapeutic methods described herein to promote antitumor efficacy of radiation in a subject, including, for example other STING activators such as members of the combretastatin (CAS 82855-09-2) family of phenols, including combretastatin A-1 (combretastatin A1 diphosphate (OXi4503 or CA1P); CAS 109971-63-3), combretastatin B-1 (CAS 109971-64-4), combretastatin A-4 (CAS 117048-59-6), and derivatives and analogs thereof such as Ombrabulin™ (Sanofi-Aventis, (CAS 181816-48-8, 253426-24-3(HCL)); or DMXAA (also known as Vadimezan™ or ASA404) (Novartis, CAS 117570-53-3).

In yet another aspect of the present disclosure, it is contemplated that radiation causes tumor cell nucleic acids and/or stress proteins to trigger the activation of TLRs-MyD88/TRIF signaling. Although not wishing to be bound by theory, it is believed based on published research that the innate immune system is the major contributor to host-defense in response to pathogens invasion or tissue damage. The initial sensing of infection and injury is mediated by pattern recognition receptors (PRRs), which recognize pathogen-associated molecular patterns (PAMPs) and damage-associated molecular patterns (DAMPs). The first-identified and well-characterized of class of PRRs I are the toll-like receptors (TLRs), which are responsible for detecting PAMPs and DAMPs outside the cell and in endosomes and lysosomes. Under the stress of chemotherapy and targeted therapies, the secretion of HMGB-1, which binds to TLR4, has been reported to be essential to antitumor effects. However, whether the same mechanism dominates radiotherapy has yet to be determined. Four endosomal TLRs (TLR3, TLR7, TLR8 and TLR9) that respond to microbial and host-mislocalized nucleic acids in cytoplasm have more recently been revealed. Through interaction of the adaptor proteins, myeloid differentiation primary-response protein 88 (MyD88) and TIR-domain-containing adaptor protein inducing IFN-β (TRIF), the activation of these four endosomal TLRs leads to significant induction of type I IFN production. Given that radiation induces production of type I IFNs, it is contemplated herein that the trigger for activation of TLRs-MyD88/TRIF signaling is by tumor cell nucleic acid and/or stress proteins generated by radiotherapy.

Although not wishing to be bound by theory, it is believed for activation of TLR3 in a subject, the subject can be administered polyinosine-polycytidylic acid poly(I:C) (0.4 mg/kg); a double-stranded DNA; a double-stranded RNA; or stathmin (Entrez Gene ID: 3925 (human), 16765 (mouse)) or a stathmin-like protein (0.4 m/kg), which is generally understood to be a protein with an α-helix structure having an amino acid homology of at least about 85%, or at least about 90%, or at least about 92% to that of amino acid residues 44-138 of human stathmin (Entrez Gene ID: 3925), including, for example, SCGIO ((Superior Cervical Ganglion 10; stathmin-2; STMN2, SCG10, SCHN10; Entrez Gene ID: 11075 (human), 20257 (mouse)), SCLIP (SCGIO-like protein; stathmin-3; STMN3; Entrez Gene ID: 50861 (human), 20262 (mouse)), and RB3 (stathmin-4; WO2007089151), and analogs and derivatives thereof such as, for example, natural or synthetic amino acid analogs thereof. A contemplated effective dose administered daily can be determined by those skilled in the art and can range, for example, from about 0.01 µg/kg to 1 g/kg or from about 0.5 µg/kg to about 400 mg/kg body weight as described in U.S. patent application Ser. No. 12/162,916. Contemplated compounds for the activation of TLR7 or TLR8 are described in U.S. Pat. No. 7,560,436. For example, TLR7 can be activated by administering to a subject imidazoquinoline compounds (for example, R-848 (InvivoGen, CAS 144875-48-9), 3M-13 and 3M-019 (both by 3M Pharmaceuticals, St. Paul, Minn.)) and those described in U.S. Pat. Nos. 4,689,338, 4,929,624, 5,238,944, 5,266,575, 5,268, 376, 5,346,905, 5,352,784, 5,389,640, 5,395,937, 5,494,916, 5,482,936, 5,525,612, 6,039,969 and 6,110,929. Other contemplated TLR7 activators include guanosine analogs, pyrimidinone compounds such as bropirimine and bropirimine analogs and the like. Imidazoquinoline compounds include, but are not limited to imiquimod (also referred to as Aldara, R-837, S-26308; InvivoGen, CAS 99011-02-6). TLR8 can be activated by, for example, administering to a subject an imidazoquinoline compound (for example, 3M-2 and 3M-3 (both by 3M Pharmaceuticals, St. Paul, Minn.); or R-848 (InvivoGen, CAS 144875-48-9)). It is further contemplated for activation of TLR9, a subject can be administered one or more CpG oligodeoxynucleotides (or CpG ODN), which are short single-stranded synthetic DNA molecules. Each CpG contains a cytosine triphosphate deoxynucleotide and a guanine triphosphate deoxynuclerotide, with a phosphodiester link between consecutive nucleotides. It is believed that the CpG motifs classified as pathogen-associated molecular patterns (PAMPs) are recognized by TLR9, which is expressed in B cells and in plasmacytoid dendritic cells in humans and some primates. CpG useful in the present disclosure may be from microbial DNA or synthetically produced, and are generally categorized into five classes: 1) Class A (Type D), 2) Class B (Type K), 3) Class C, 4) Class P, and 5) Class S. Class A ODN includes ODN 2216, which stimulates large amounts of Type I interferon production, including IFNα, induces the maturation of plasmacytoid dendritic cells, and is a strong activator of NK cells through indirect cytokine signaling. Class A ODN is generally characterized by the presences of a poly G sequence at the 5' end, the 3' end, or both, a partially phosphorothioated-modified backbone, an internal palindrome sequence and GC dinucleotides contained within the internal palindrome. Class B ODN includes ODN 2006 (InvivoGen, ODN 7909, PF_3512676) and ODN 2007 (InvivoGen), which is a strong stimulator of human B cell and monocyte maturation and to a lesser extent a stimulator of IFN and the maturation of pDC. Structural characteristics of Class B ODN include an about a 18 to 28 nucleotide length, a fully phosphorothioated (PS-modified) backbone and one or more 6mer CpG motif 5'-Pu Py C G Py Pu-3'.

Although there are no direct activators of MyD88 or TRIF known at this time, it is contemplated that as agents are discovered or developed that interact with these proteins, these agents can be used and incorporated into the therapeutic methods and disclosure described herein.

A newly defined endoplasmic reticulum associated protein STING (stimulator of interferon genes) has also been demonstrated to be a mediator for type I IFN induction by intracellular exogenous DNA in a TLR-independent manner. Cytosolic detection of DNA activates STING in the cytoplasm, which binds to TBK1 (TANK-binding kinase 1) and IKK (IκB kinase), that in turn activates the transcription factors IRF3 (interferon regulatory factor 3)/STAT6, and NF-κB (nuclear factor κB), respectively. Subsequently, nuclear translocation of these transcription factors leads to the induction of type I IFNs and other cytokines that participate in host defense. In the past six years, STING has been demonstrated to be essential for the host protection against DNA pathogens through various mechanisms. STING is also a mediator for autoimmune diseases which are initiated by the aberrant cytoplasmic DNA. Following the recognition of cytosolic DNA, cGAMP synthase (cGAS) catalyzes the generation of 2' to 5' cyclic GMP-AMP (cGAMP), which binds to and activates STING signaling. More recently, cGAS has been considered as a universal cytosol DNA sensor for STING activation, such as in the setting of viral infection and lupus erythematosus. Now we elucidate the role of host cGAS-STING in the sensing of irradiated-tumor cells. Here, we demonstrate that radiotherapy is dominated by a distinct mechanism different from chemotherapy and targeted therapies with antibodies, which rely on HMGB-1-TLR4-MyD88 interaction. Antitumor effects of radiation are controlled by newly defined cGAS-STING-dependent cytosolic DNA sensing pathway, which drives a rigorous innate immune response and a robust adaptive immune response to radiation.

In another aspect of the present disclosure, it is contemplated that an agent administered to a subject undergoing radiotherapy that increases cGAS levels in a cancerous cell as compared to an untreated cancerous state control cell, promotes antitumor efficacy of the radiation as compared to an untreated (that is, no agent is administered to the subject undergoing radiotherapy) control subject. While not wishing to be bound by theory, is it believed that cGAS mediates type I IFN production to enhance the function of dendritic cells in response to irradiated-tumor cells. We therefore contemplate that DNA from irradiated-tumor cells delivered into the cytosol of dendritic cells binds to cGAS to trigger STING-dependent type I IFN induction. Although cancer type, tissue and/or subject dependent, it is contemplated that elevated cGAS levels generally greater than about 10%, 25%, 50%, 75%, 100% or greater in a treated cancerous cells as compared to an untreated control cell provides the desired antitumor efficacy in a subject undergoing radiotherapy for a particular cancer. Such agents that increase cGAS levels in a cell include, for example DNA damaging agents used in the clinic at clinical doses. In one embodiment, the agent is delivered to a cancerous cell by a pharmaceutical carrier such as a nanocarrier, a conjugate, a nucleic-acid-lipid particle, a vesicle, a exosome, a protein capsid, a liposome, a dendrimer, a lipoplex, a micelle, a virosome, a virus like particle, a nucleic acid complexes, and mixtures and derivatives thereof. In yet another embodiment, the agent is delivered into the cytosol of the subject's dendritic cell by, for example, the pharmaceutical carrier via intratumoral (IT), intraveinous (IV), and/or intraperitoneal (IP) administration.

Therefore, this disclosure provides insight into understanding the mechanism of radiation-mediated tumor regression and forms new strategies for improvements in radiotherapy efficacy in cancer patients.

High and low expression of LGP2 refers to expression levels of about +/−1.5 fold, respectively, as related to average level of expression of this gene in investigated and published databases.

Reactive Oxygen Species (ROS) are molecules containing oxygen and generally very chemically reactive. Examples include oxygen ions and peroxides. ROS also is created as a natural by-product of the normal metabolism of oxygen, but when a cell is exposed to environmental stress such as UV or heat exposure, ROS levels can increase dramatically resulting in significant cell damage known as oxidative stress. Such damage includes damage to cellular proteins, lipids and DNA, that may lead to fatal lesions in a cell that contributes to carcinogenesis. Ionizing radiation may also generate ROS in a cell and may result in considerable damage to the cell.

A shRNA (small hairpin RNA or short hairpin RNA) is a sequence of RNA getting its name from a tight hairpin turn that can be used to silence target gene expression via RNA interference (RNAi). Expression of shRNA in cells is generally known in the art and is typically accomplished by the delivery of plasmids or through viral or bacterial vectors.

A siRNA (small interfering RNA (siRNA) (also known as short interfering RNA or silencing RNA) is a class of double-stranded RNA molecules, 20-25 base pairs in length. siRNA plays a role in several important pathways including the RNA interference (RNAi) pathway and the RNAi-related pathways. siRNA may, for example, interfere with the expression of specific genes with complementary nucleotide sequence.

LPG2, MDA5, and RIG-1 are members of the RIG-1-like receptor dsRNA helicase enzyme family. In humans, LGP2 (Laboratory of Genetics and Physiology 2) is encoded by the DHX58 gene; RIG-1 (retinoic acid-inducible gene 1) is encoded by the DDX58 gene; and MDA5 (Melanoma Differentiation-Associated protein 5) is encoded by the IFIH1gene. LGP2 (Human Entrez GeneID: 79132; Mouse Entrez GeneID: 80861) may also be identified by the symbols LGP-2, DHX58, D11LGP2, D11lgp2e, and RLR-3; RIG-1 (Human Entrez GeneID: 23586; Mouse Entrez GeneID: 230073) may also be identified by the symbols RIGI, DDX58, and RLR-1; and MDA5 (Human Entrez GeneID: 64135; Mouse Entrez GeneID: 71586) may also be identified as MDA-5, IFIHI, Hlcd, IDDM19, and RLR-2.

MAVS (Mitochondrial antiviral-signaling protein) is a protein that in humans is encoded by the MAVS gene. The MAVS protein (Human Entrez GeneID: 57506; Mouse Entrez GeneID: 228607) may also be identified by the symbols CARDIF; IPS-1, IPS1, and VISA.

In humans, TREX1 (Three prime repair Exonuclease 1) is an enzyme that is encoded by the TREX1gene. TREX1 (Human Entrez GeneID: 11277; Mouse Entrez GeneID: 22040) may also be identified by the symbols AGS1, CRV, DRN3, and HERNS.

DAI (DNA-dependent Activator of IFN regulatory factors), also identified as DLM-1/ZBP1, functions as a DNA sensor in humans and is generally thought to activate the innate immune system.

IFI16 (Gamma-interferon-inducible protein Ifi-16) in humans is a protein that is encoded by the IFI16 gene. IFI16 (Human Entrez GeneID: 3428; Mouse Entrez GeneID: 15951) may also be identified by the symbols IFI-16, IFNGIP1 and PYHIN2, and be known as interferon-inducible myeloid differentiation transcriptional activator.

AIM2 (Interferon-inducible protein AIM2) is a protein that in humans is encoded by the AIM2 gene and a member of the IFI16 family. AIM2 (Human Entrez GeneID: 9447; Mouse Entrez GeneID: 383619) may also be known as Absent In Melanoma 2 and by the symbol PYHIN4.

STING (Stimulator of Interferon (IFN) Genes) in humans is encoded by the TMEM173 gene and may also be identified by the symbols TMEM173, ERIS, MITA, MPYS, and NET23.

cGAS (cyclic-GMP-AMP synthase) in humans is encoded by the MB21D1/C6orf150 gene and may also be identified by the symbols cGAS, MB21D1, and C6orf150. cGAS may also be known as cGAMP synthase.

It is further contemplated that a treatment regimen may include administering an antineoplastic agent (e.g., chemotherapy) along with IR (or radiotherapy) to treat a resistant cancer cell. An illustrative antineoplastic agent or chemotherapeutic agent include, for example, a standard taxane. Taxanes are produced by the plants of the genus *Taxus* and are classified as diterpenes and widely uses as chemotherpy agents including, for example, paclitaxel, (Taxol®, Bristol-Meyers Squibb, CAS 33069-62-4) and docetaxel (Taxotere®, Sanofi-Aventis, CAS 114977-28-5). Other chemotherapeutic agent include semi-synthetic derivatives of a natural taxoid such as cabazitaxel (Jevtana®, Sanofi-Aventis, CAS 183133-96-2). Other chemotherapeutic agent also include an androgen receptor inhibitor or mediator. Illustrative androgen receptor inhibitors include, a steroidal anti-androgen (for example, cyperterone, CAS 2098-66-0); a non-steroidal antiandrogen (for example, flutamide, Eulexin®, Schering-Plough, CAS 13311-84-7); nilutamide (Nilandron®, CAS 63612-50-0); enzalutamide (Xtandi®, Medivation®, CAS 915087-33-1); bicalutamide (Casodex, AstraZeneca, CAS 90357-06-5); a peptide antiandrogen; a small molecule antiandrogen (for example, RU58642 (Roussel-Uclaf S A, CAS 143782-63-2); LG120907 and LG105 (Ligand Pharmaceuticals); RD162 (Medivation, CAS 915087-27-3); BMS-641988 (Bristol-Meyers Squibb, CAS 573738-99-5); and CH5137291 (Chugai Pharmaceutical Co. Ltd., CAS 104344603904)); a natural antiandrogen (for example, ataric acid (CAS 4707-47-5) and N-butylbensensulfonamide (CAS 3622-84-2); a selective androgen receptor modulator (for example, enobosarm (Ostarine®, Merck & Company, CAS 841205-47-8); BMS-564,929 (Bristol-Meyer Squibb, CAS 627530-84-1); LGD-4033 (CAS 115910-22-4); AC-262,356 (Acadia Pharmaceuticals); LGD-3303 (Ganolix Lifescience Co., Ltd., 9-chloro-2-ethyl-1-methyl-3-(2,2,2-trifluoroethyl)-3H-pyrrolo[3,2-f]quinolin-7(6H)-one; S-40503, Kaken Pharmaceuticals, 2-[4-(dimethylamino)-6-nitro-1,2,3,4-tetrahydroquinolin-2-yl]-2-methylpropan-1-ol); andarine (GTx-007, S-4, GTX, Inc., CAS 401900-40-1); and S-23 (GTX, Inc., (2S)—N-(4-cyano-3-trifluoromethylphenyl)-3-(3-fluoro-4-chlorophenoxy)-2-hydroxy-2-methyl-propanamide)); or those described in U.S. Patent Appln. No. 2009/0304663. Other neoplastic agents or chemotherapeutic agents that may be used include, for example: alkylating agents such as nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; biological response modifiers such as interferon alphenomes; other agents such as platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MTH); adrenocortical suppressant such as mitotane (o,p'-DDD) and aminoglutethimide; taxol analogues/derivatives; hormone agonists/antagonists such as flutamide and tamoxifen; and GnRH and analogues thereof. Examples of other chemotherapeutic can be found in Cancer Principles and Practice of Oncology by V. T. Devita and S. Hellman (editors), 6.sup.th edition (Feb. 15, 2001), Lippincott Williams & Wilkins Publishers.

Radiotherapy is based on ionizing radiation delivered to a target area that results in death of reproductive tumor cells. Some examples of radiotherapy include the radiation of cesium, palladium, iridium, iodine, or cobalt and is usually delivered as ionizing radiation delivered from a linear accelerator or an isotopic source such as a cobalt source. Also variations on linear accelerators are Cyberkine and Tomotherapy. Particle radiotherapy from cyclotrons such as Protons or Carbon nuclei may be employed. Also radioisotopes delivered systemically such as p32 or radiou 223 may be used. The external radiotherapy may be systemic radiation in the form of sterotacktic radiotherapy total nodal radiotherapy or whole body radiotherapy but is more likely focused to a particular site, such as the location of the tumor or the solid cancer tissues (for example, abdomen, lung, liver, lymph nodes, head, etc.). The radiation dosage regimen is generally defined in terms of Gray or Sieverts time and fractionation, and must be carefully defined by the radiation oncologist. The amount of radiation a subject receives will depend on various consideration but the two important considerations are the location of the tumor in relation to other critical structures or organs of the body, and the extent to which the tumor has spread. One illustrative course of treatment for a subject undergoing radiation therapy is a treatment schedule over a 5 to 8 week period, with a total dose of 50 to 80 Gray (Gy) administered to the subject in a single daily fraction of 1.8 to 2.0 Gy, 5 days a week. A Gy is an abbreviation for Gray and refers to 100 rad of dose.

Radiotherapy can also include implanting radioactive seeds inside or next to an site designated for radiotherapy and is termed brachytherapy (or internal radiotherapy, endocurietherapy or sealed source therapy). For prostate cancer, there are currently two types of brachytherapy: permanent and temporary. In permanent brachytherapy, radioactive (iodine-125 or palladium-103) seeds are implanted into the prostate gland using an ultrasound for guidance. Illustratively, about 40 to 100 seeds are implanted and the number and placement are generally determined by a computer-generated treatment plan known in the art specific for each subject. Temporary brachytherapy uses a hollow source placed into the prostate gland that is filled with radioactive material (iridium-192) for about 5 to about 15 minutes, for example. Following treatment, the needle and radioactive material are removed. This procedure is repeated two to three times over a course of several days.

Radiotherapy can also include radiation delivered by external beam radiation therapy (EBRT), including, for example, a linear accelerator (a type of high-powered X-ray machine that produces very powerful photons that penetrate deep into the body); proton beam therapy where photons are derived from a radioactive source such as iridium-192, caesium-137, radium-226 (no longer used clinically), or colbalt-60; Hadron therapy; multi-leaf collimator (MLC); and intensity modulated radiation therapy (IMRT). During this type of therapy, a brief exposure to the radiation is given for a duration of several minutes, and treatment is typically given once per day, 5 days per week, for about 5 to 8 weeks. No radiation remain in the subject after treatment. There are several ways to deliver EBRT, including, for example, three-dimensional conformal radiation therapy where the beam intensity of each beam is determined by the shape of the tumor. Illustrative dosages used for photon based radiation is measured in Gy, and in an otherwise healthy subject (that is, little or no other disease states present such as high blood pressure, infection, diabetes, etc.) for a solid epithelial tumor ranges from about 60 to about 80 Gy, and for a lymphoma ranges from about 20 to about 40 Gy. Illustrative preventative (adjuvant) doses are typically given at about 45 to about 60 Gy in about 1.8 to about 2 Gy fractions for breast, head, and neck cancers.

When radiation therapy is a local modality, radiation therapy as a single line of therapy is unlikely to provide a cure for those tumors that have metastasized distantly outside the zone of treatment. Thus, the use of radiation therapy with other modality regimens, including chemotherapy, have important beneficial effects for the treatment of metastasized cancers.

Radiation therapy has also been combined temporally with chemotherapy to improve the outcome of treatment. There are various terms to describe the temporal relationship of administering radiation therapy and chemotherapy, and the following examples are illustrative treatment regimens and are generally known by those skilled in the art and are provided for illustration only and are not intended to limit the use of other combinations. "Sequential" radiation therapy and chemotherapy refers to the administration of chemotherapy and radiation therapy separately in time in order to allow the separate administration of either chemotherapy or radiation therapy. "Concomitant" radiation therapy and chemotherapy refers to the administration of chemotherapy and radiation therapy on the same day. Finally, "alternating" radiation therapy and chemotherapy refers to the administration of radiation therapy on the days in which chemotherapy would not have been administered if it was given alone.

It should be noted that other therapeutically effective doses of radiotherapy can be determined by a radiation oncologist skilled in the art and can be based on, for example, whether the subject is receiving chemotherapy, if the radiation is given before or after surgery, the type and/or stage of cancer, the location of the tumor, and the age, weight and general health of the subject.

It is further contemplated that subsets of gene targets, including those identified or described herein, could be used as a therapeutic tool for diagnosing and/or treating a tumor or cancer. For example, siRNA pools (or other sets of molecules individually specific for one or more predetermined targets including, for example, shRNA pools, small molecules, and/or peptide inhibitors, collectively "expression inhibitors" or "active ingredients" or "active pharmaceutical ingredients") may be generated based on one or more (e.g., 2 or 4 or 8 or 12, or any number) targets and used to treat a subject in need thereof (e.g., a mammal having a chemoresistant or radioresistant cancer). Upon rendering of the subject's cancer chemosensitive and/or radiosensitive, therapeutic intervention in the form of antineoplastic agents and/or ionizing radiation as known in the art (see for example, U.S. Pat. No. 6,689,787, incorporated by reference) may be administered to reduce and/or eliminate the cancer. It is contemplated that therapeutic intervention may occur before, concurrent, or subsequent the treatment to render the subject chemosensitive or radiosensitive. It is further envisioned that particular subsets of targets may be advantageous over others based on the particular type of cancer and/or tissue of origin for providing a therapeutic effect. Administration of such therapies may be accomplished by any means known in the art.

In one embodiment, a kit may include a panel of siRNA pools directed at one or more targets as identified by or in the present disclosure. It is envisioned that a particular kit may be designed for a particular type of cancer and/or a specific tissue. The kit may further include means for administering the panel to a subject in need thereof. In addition, the kit may also include one or more antineoplastic agents directed at the specific type of cancer against which the kit is directed and one or more compounds that inhibit that Jak/Stat pathway.

Kits may further be a packaged collection of related materials, including, for example, a single and/or a plurality of dosage forms each approximating an therapeutically effective amount of an active ingredient, such as, for example, an expression inhibitor and/or a pharmaceutical compound as described herein that slows, stops, or reverses the growth or proliferation of a tumor or cancer or kills tumor or cancer cells, and/or an additional drug. The included dosage forms may be taken at one time, or at a prescribed interval. Contemplated kits may include any combination of dosage forms.

A kit may also be a prognostic kit for use with a tissue suffering from or having a cancer, including, for example, a tissue taken from a subject suffering from a high grade glioma. The prognostic kit may contain at least one set of primers for QRT-PCR detection of LGP2 to determine expression levels of LGP2 in the tissue. The prognostic kit may also include at least one of: a reagent for purification of total RNA from the tissue, a set of reagents for a QRT-PCR reaction, and/or a positive control for detection of LGP2 mRNA. Generally, high expression levels of LGP2 and low expression levels of LGP2 predict improved prognosis in treating the cancer in the tissue or the subject from which the tissue was derived. The tissue may also be from any part of the subject in which the cancer is present including, for example, tissue from the brain. As for thresholds of prognosis for LGP2 levels, the use of high and low+/−1.5 fold as related to average level of expression of this gene in investigated and published databases can be used. For example, "high expression" levels of LGP2 may be, for example, at least about 1.5 fold greater than an expression level of LGP2 in a normal non-disease state tissue; while "low expression" levels of LGP2 may be, for example, at least about 1.5 fold less than an expression level of LGP2 in a normal non-disease state tissue.

In another embodiment, a method of treating a subject in need thereof includes administering to the subject one or more molecules that target one or more genes such as siRNA and/or shRNA pools. The method may further include, for example, treatment of the subject with one or more antineoplastic agents, ionizing radiation, and/or one or more compounds that inhibit that Jak/Stat pathway.

Suppression of a gene refers to the absence of expression of a gene or a decrease in expression of a gene or suppression of a product of a gene such as the protein encoded by the given gene as compared to the activity of an untreated gene. Suppression of a gene may be determined by detecting the presence or absence of expression of a gene or by measuring a decrease of expression of a gene by any means known in the art including, for example, detecting a decrease in the level of the final gene product, such as a protein, or detecting a decreased level of a precursor, such as mRNA, from which gene expression levels may be inferred when compared to normal gene activity, such as a negative (untreated) control. Any molecular biological assay to detect mRNA or an immunoassay to detect a protein known in the art can be used. A molecular biological assay includes, for example, polymerase chain reaction (PCR), Northern blot, Dot blot, or an analysis method with microarrays. An immunological assay includes, for example, ELISA (enzyme-linked immunosorbent assay) with a microtiter plate, radioimmunoassay (RIA), a fluorescence antibody technique, Western blotting, or an immune structure dyeing method. Suppression of a gene may also be inferred biologically in vivo, in situ, and/or in vitro, by the suppression of growth or proliferation of a tumor or cancer cell, cell death of a tumor or cancer cell, and/or the sensitization of a tumor or cancer cell to chemotherapy and/or radiotherapy. Illustratively, a therapeutically effective amount or a therapeutically effective amount of gene suppression in a subject results in the suppression of growth or proliferation of a tumor or cancer cell, cell death of the tumor or cancer cell, sensitization of the tumor or cancer cell to chemotherapy and/or radiotherapy, and/or protecting normal non-disease state tissue from genotoxic stress. As each subject is different and each cancer is different, the quantitative amount to achieve a therapeutically effective amount in a subject may be determined by a trained professional skilled in the area on a case by case basis. Illustratively, a therapeutically effective amount of gene suppression may include, for example, less than or equal to about 95% of normal gene activity, or less than or equal to about 90% of normal gene activity, or less than or equal to about 85% of normal gene activity, or less than or equal to about 80% of normal gene activity, or less than or equal to about 75% of normal gene activity, or less than or equal to about 65% of normal gene activity, or less than or equal to about 50% of normal gene activity, or less than or equal to about 35% of normal gene activity, or less than or equal to about 25% of normal gene activity, or less than or equal to about 15% of normal gene activity, or less than or equal to about 10% of normal gene activity, or less than or equal to about 7.5% of normal gene activity, or less than or equal to about 5% of normal gene activity, or less than or equal to about 2.5% of normal gene activity, or less than or equal to about 1% of normal gene activity, or less than or equal to about 0% of normal gene activity.

Suppression of identified genes individually or in combination combined with ionizing radiation and/or any chemotherapeutic agents may improve the outcome of patients treated with the ionizing radiation or any chemotherapy agent or any treatment designed to improve outcome of the cancer patients if such treatment is combined with the suppression of any of these genes or their combination.

Based on the functional groups, we also contemplate that suppression of the chemokine signaling, or suppression of negative regulators of interferon response, or suppression of protein degradation or mitochondria-related anti-apoptotic molecules or anti-viral proteins or extracellular matrix proteins (ECM) alone or in combination with ionizing radiation or any chemotherapy drug or any treatment designed to improve outcome of the cancer patients will improve cancer treatment. This is based on the functional associations between detected targets. DHX58 (also known as LGP2) is known as an apical suppressor of RNA dependent activation of the Type I interferons alpha and beta. IFITM1 and OASL are known anti-viral proteins. USP18 and HERC5 are enzymes involved in protein ISGylation/de-ISGylation, known to protect proteins from ubiquitin-dependent degradation in proteosome complex, while PSMB9 and PSMB10 are proteasome subunits. EPSTL1, LGALS3P and TAGLN are involved in the structure and functional regulation of ECM. CXCL9 and CCL2 are chemokines with multiple functions including growth-promoting functions for tumor cells.

Jak (Janus kinase) refers to a family of intracellular, nonreceptor tyrosine kinases and includes four family members, Janus 1 (Jak-1), Janus 2 (Jak-2), Janus 3 (Jak-3), and Tyrosine kinase 2 (Tyk2).

Stat (Signal Transducer and Activator of Transcription) plays a role in regulating cell growth, survival and differentiation and the family includes Stat1, Stat2, Stat3, Stat4, Stat5 (Stat5a and Stat5b), and Stat6.

The term "subject" refers to any organism classified as a mammal, including mice, rats, guinea pigs, rabbits, dogs, cats, cows, horses, monkeys, and humans.

As used herein, the term "cancer" refers to a class of diseases of mammals characterized by uncontrolled cellular growth. The term "cancer" is used interchangeably with the terms "tumor," "solid tumor," "malignancy," "hyperproliferation" and "neoplasm." Cancer includes all types of hyperproliferative growth, hyperplasic growth, neoplastic growth, cancerous growth or oncogenic processes, metastatic tissues or malignantly transformed cells, tissues, or organs, irrespective of histopathologic type or stage of invasiveness. Illustrative examples include, lung, prostate, head and neck, breast and colorectal cancer, melanomas and gliomas (such as a high grade glioma, including glioblastoma multiforme (GBM), the most common and deadliest of malignant primary brain tumors in adult humans).

As used herein, the phrase "solid tumor" includes, for example, lung cancer, head and neck cancer, brain cancer, oral cancer, colorectal cancer, breast cancer, prostate cancer, pancreatic cancer, and liver cancer. Other types of solid tumors are named for the particular cells that form them, for example, sarcomas formed from connective tissue cells (for example, bone cartilage, fat), carcinomas formed from epithelial tissue cells (for example, breast, colon, pancreas) and lymphomas formed from lymphatic tissue cells (for example, lymph nodes, spleen, thymus). Treatment of all types of solid tumors regardless of naming convention is within the scope of this invention.

As used herein, the term "chemoresistant" refers to a tumor or cancer cell that shows little or no significant detectable therapeutic response to an agent used in chemotherapy.

As used herein, the term "radioresistant" refers to a tumor or cancer cell that shows little or no significant detectable therapeutic response to an agent used in radiotherapy such as ionizing radiation.

As used herein, the term "chemosensitive" refers to a tumor or cancer cell that shows a detectable therapeutic response to an agent used in chemotherapy.

As used herein, the term "radiosensitive" refers to a tumor or cancer cell that shows a detectable therapeutic response to an agent used in radiotherapy.

As used herein, the phrases "chemotherapeutic agent," "cytotoxic agent," "anticancer agent," "antineoplastic agent" and "antitumor agent" are used interchangeably and refer to an agent that has the effect of inhibiting the growth or proliferation, or inducing the killing, of a tumor or cancer cell. The chemotherapeutic agent may inhibit or reverse the development or progression of a tumor or cancer, such as for example, a solid tumor.

As used herein, the term "chemotherapy" refers to administration of at least one chemotherapeutic agent to a subject having a tumor or cancer.

As used herein, the term "radiotherapy" refers to administration of at least one "radiotherapeutic agent" to a subject having a tumor or cancer and refers to any manner of treatment of a tumor or cancer with a radiotherapeutic agent. A radiotherapeutic agent includes, for example, ionizing radiation including, for example, external beam radiotherapy, stereotatic radiotherapy, virtual simulation, 3-dimensional conformal radiotherapy, intensity-modulated radiotherapy, ionizing particle therapy and radioisotope therapy.

Compositions herein may be formulated for oral, rectal, nasal, topical (including buccal and sublingual), transdermal, vaginal, injection/injectable, and/or parental (including subcutaneous, intramuscular, intravenous, and intradermal) administration. Other suitable administration routes are incorporated herein. The compositions may be presented conveniently in unit dosage forms and may be prepared by any methods known in the pharmaceutical arts. Examples of suitable drug formulations and/or forms are discussed in, for example, Hoover, John E. Remington's Pharmaceutical Sciences, Mack Publishing Co., Eston, Pa.; 18.sup.th edition (1995); and Liberman, H. A. and Lachman, L. Eds., Pharmaceutical Dosage Forms, Marcel Decker, New York, N.Y., 1980. Illustrative methods include the step of bringing one or more active ingredients into association with a carrier that constitutes one or more accessory ingredients. In general, the compositions may be prepared by bringing into association uniformly and intimately one or more active ingredients with liquid carriers or finely divided solid carriers or both, and then, if necessary, shaping the product.

Pharmaceutical formulations may include those suitable for oral, intramuscular, rectal, nasal, topical (including buccal and sub-lingual), vaginal or parenteral (including intramuscular, subcutaneous and intravenous) administration or in a form suitable for administration by inhalation or insufflation. One or more of the compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

A salt may be a pharmaceutically suitable (i.e., pharmaceutically acceptable) salt including, but not limited to, acid addition salts formed by mixing a solution of the instant compound with a solution of a pharmaceutically acceptable acid. A pharmaceutically acceptable acid may be, for example, hydrochloric acid, methanesulphonic acid, fumaric acid, maleic acid, succinic acid, acetic acid, benzoic acid, oxalic acid, citric acid, tartaric acid, carbonic acid or phosphoric acid.

Suitable pharmaceutically-acceptable salts may further include, but are not limited to salts of pharmaceutically-acceptable inorganic acids, including, for example, sulfuric, phosphoric, nitric, carbonic, boric, sulfamic, and hydrobromic acids, or salts of pharmaceutically-acceptable organic acids such propionic, butyric, maleic, hydroxymaleic, lactic, mucic, gluconic, benzoic, succinic, phenylacetic, toluenesulfonic, benezenesulfonic, salicyclic sulfanilic, aspartic, glutamic, edetic, stearic, palmitic, oleic, lauric, pantothenic, tannic, ascorbic, and valeric acids.

Various pharmaceutically acceptable salts include, for example, the list of FDA-approved commercially marketed salts including acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

A hydrate may be a pharmaceutically suitable (i.e., pharmaceutically acceptable) hydrate that is a compound formed by the addition of water or its elements to a host molecule (for example, the free form version of the compound) including, but not limited to, monohydrates, dihydrates, etc. A solvate may be a pharmaceutically suitable (i.e., pharmaceutically acceptable) solvate, whereby solvation is an interaction of a solute with a solvent which leads to stabilization of the solute species in a solution, and whereby the solvated state is an ion in a solution complexed by solvent molecules. Solvates and hydrates may also be referred to as "analogues" or "analogs."

A prodrug may be a compound that is pharmacologically inert but is converted by enzyme or chemical action to an active form of the drug (i.e., an active pharmaceutical ingredient) at or near the predetermined target site. In other words, prodrugs are inactive compounds or partially active compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism.

Carrier prodrugs are formed by combining the active drug (e.g., active ingredient) with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartite prodrugs. Prodrugs where the carrier is linked to the drug by a separate structure are referred to as tripartite prodrugs, whereby the carrier is removed by an enzyme-controlled metabolic process, and whereby the linking structure is removed by an enzyme system or by a chemical reaction. A hydroxy-protecting group includes, for example, a tert-butyloxy-carbonyl (t-BOC) and t-butyl-dimethyl-silyl (TBS). Other hydroxy protecting groups contemplated are known in the art.

In another embodiment, a dosage form and/or composition may include one or more active metabolites of the active ingredients in place of or in addition to the active ingredients disclosed herein.

Dosage form compositions containing the active ingredients may also contain one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (for example, anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, an oral dosage form may include capsules (a solid oral dosage form consisting of a shell and a filling, whereby the shell is composed of a single sealed enclosure, or two halves that fit together and which are sometimes sealed with a band and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), and capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle).

Oral dosage forms contemplated herein also include granules (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), or syrup (an oral solution containing high concentrations of sucrose or other sugars; the term has also been used to include any other liquid dosage form prepared in a sweet and viscid vehicle, including oral suspensions).

Oral dosage forms contemplated herein may further include a tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, for example, citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), and the like.

Injection and infusion dosage forms (i.e., parenteral dosage forms) include, but are not limited to, the following. Liposomal injection includes or forms liposomes or a lipid bilayer vesicle having phospholipids that encapsulate an active drug substance. Injection includes a sterile preparation intended for parenteral use. Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution suitable for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

A parenteral carrier system may include one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

Inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols). Inhalation dosage forms further include foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. Inhalation dosage forms also include metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and aerosol spray being an aerosol product which utilizes a compressed gas as the propellant to provide the force necessary to expel the product as a wet spray and being applicable to solutions of medicinal agents in aqueous solvents.

Pharmaceutically suitable inhalation carrier systems may include pharmaceutically suitable inactive ingredients known in the art for use in various inhalation dosage forms, such as (but not limited to) aerosol propellants (for example, hydrofluoroalkane propellants), surfactants, additives, suspension agents, solvents, stabilizers and the like.

A transdermal dosage form may include, but is not limited to, a patch being a drug delivery system that often contains an adhesive backing that is usually applied to an external site on the body, whereby the ingredients either passively diffuse from, or are actively transported from some portion of the patch, and whereby depending upon the patch, the ingredients are either delivered to the outer surface of the body or into the body; and other various types of transdermal patches such as matrix, reservoir and others known in the art. The "pharmaceutically suitable transdermal carrier system" includes pharmaceutically suitable inactive ingredients known in the art for use in various transdermal dosage forms, such as (but not limited to) solvents, adhesives, diluents, additives, permeation enhancing agents, surfactants, emulsifiers, liposomes, and the like.

Commonly used techniques for the introduction of the nucleic acid molecules into cells (for example, the cytosol of a dendritic cell), tissues, and organisms that can also be used in the present disclosure include the use of various carrier systems, reagents and vectors, including, for example, pharmaceutically-acceptable carriers such as nanocarriers, conjugates, nucleic-acid-lipid particles, vesicles, exosomes, protein capsids, liposomes, dendrimers, lipoplexes, micelles, virosomes, virus like particles, nucleic acid complexes, and mixtures thereof. Nanocarriers generally range in the size from about 1 nm to about 100 nm or about 200 nm in diameter, and can be made from, for example, micelles, polymers, carbon-based materials, liposomes, and other substances known to those skilled in the art.

The dosing of an agent of the present disclosure to a human subject may be determined by those skilled in the art based upon known methods such as animal studies and clinical trials involving human subjects. For example, Budman D R, Calvert, A H, and Rowinsky E K, *Handbook of Anticancer Drug Development*, describes dose-escalation studies to find the maximum tolerable dosage (MTD) along with dose-limiting toxicity (DLT). Generally, the starting dose can be derived by allometric scaling from dosing studies in mice. The lethal dose ($LD_{10}$) is also determined in mice. Following mice studies, ¹/₁₀ of the mouse $LD_{10}$ is administered to a cohort of healthy subjects. Escalating dose administers a dose 100%, 67%, 50%, 40%, and 33% thereafter of the previously described dose (¹/₁₀ mouse $LD_{10}$) (in other words, the second dose level is 100% greater than the first, the third is 67% greater than the second and so forth) to determine the pharmacokinetics of the agent in the subjects, which is then used to determine proper dosing regimens, including dosage amounts, routes of administration, timing of administration, etc. This is followed by more dosing studies in diseased subjects to determine a therapeutically effective dosage parameters in treating the disease in a broader population of subjects. Suitable dosage amounts and dosing regimens may also be in consideration of a variety of factors, including one or more particular conditions being treated, the severity of the one or more conditions, the genetic profile, age, health, sex, diet, and weight of the subject, the route of administration alone or in combination with pharmacological considerations including the activity, efficacy, bioavailability, pharmacokinetic, and toxicological profiles of the particular compound employed, whether a drug delivery system is utilized and/or whether the drug is administered as part of a drug combination. Therefore, the dosage regimen to be employed may vary widely and may necessarily deviate from the dosage regimens set forth herein.

In regard to an expression inhibitor of the present disclosure, it is contemplated that dosage forms may include an amount of one or more expression inhibitors (or inhibitors of expression) ranging from about 1 to about 1400 mg, or about 5 to about 100 mg, or about 25 to about 800 mg, or about 100 to about 500 mg, or 0.1 to 50 milligrams (±10%), or about 10 to about 100 milligrams (±10%), or about 5 to about 500 milligrams (±10%), or about 0.1 to about 200 milligrams (±10%), or about 1 to about 100 milligrams (±10%), or about 5 to about 50 milligrams (±10%), or about 30 milligrams (±10%), or about 20 milligrams (±10%), or about 10 milligrams (±10%), or about 5 milligrams (±10%), per dosage form, such as, for example, a tablet, a pill, a bolus, and the like.

A dosage form of the present disclosure may be administered to a subject in need thereof, for example, once per day, twice per day, once every 6 hours, once every 4 hours, once every 2 hours, hourly, twice an hour, twice a day, twice a week, or monthly.

The phrase "therapeutically effective" is intended to qualify the amount that will achieve the goal of improvement in disease severity and/or the frequency of incidence over non-treatment, while limiting, reducing, or avoiding adverse side effects typically associated with disease therapies. A "therapeutic effect" relieves to some extent one or more of the symptoms of a cancer disease or disorder. In reference to the treatment of a cancer, a therapeutic effect refers to one or more of the following: 1) reduction in the number of cancer cells by, for example, killing the cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disease or disorder; and/or 7) relieving or reducing the side effects associated with the administration of an anticancer agent. "Therapeutic effective amount" is intended to qualify the amount required to achieve a therapeutic effect. For example, a therapeutically effective amount of an expression inhibitor (or inhibitors of expression) may be any amount that begins to improve cancer treatment in a subject. In one embodiment, an effective amount of an expression inhibitor used in the therapeutic regime described herein may be, for example, about 1 mg, or about 5 mg, or about 10 mg, or about 25 mg, or about 50 mg, or about 100 mg, or about 200 mg, or about 400 mg, or about 500 mg, or about 600 mg, or about 1000 mg, or about 1200 mg, or about 1400 mg, or from about 10 to about 60 mg, or about 50 mg to about 200 mg, or about 150 mg to about 600 mg per day. Further, another effective amount of an expression inhibitor used herein may be that which results in a detectable blood level of above about 1 ng/dL, 5, ng/dL, 10 ng/dL, 20, ng/dL, 35 ng/dL, or about 70 ng/dL, or about 140 ng/dL, or about 280 ng/dL, or about 350 ng/dL, or lower or higher.

The term "pharmaceutically acceptable" is used herein to mean that the modified ion is appropriate for use in a pharmaceutical product. Pharmaceutically acceptable cations include metallic ions and organic ions. Other metallic ions include, but are not limited to appropriate alkali metal salts, alkaline earth metal salts and other physiological acceptable metal ions. Exemplary ions include aluminium, calcium, lithium, magnesium, potassium, sodium and zinc in their usual valences. Organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

It is further contemplated that one active ingredient may be in an extended release form, while an optional second, third, or fourth other active ingredient, for example, may or may not be, so the recipient experiences, for example, a spike in the second, third, or fourth active ingredient that dissipates rapidly, while the first active ingredient is maintained in a higher concentration in the blood stream over a longer period of time. Similarly, one of the active ingredients may be an active metabolite, while another may be in an unmetabolized state, such that the active metabolite has an immediate effect upon administration to a subject whereas the unmetabolized active ingredient administered in a single dosage form may need to be metabolized before taking effect in the subject.

Also contemplated are solid form preparations that include at least one active ingredient which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Solutions or suspensions may be applied topically and/or directly to the nasal cavity, respiratory tract, eye, or ear by conventional means, for example with a dropper, pipette or spray.

Alternatively, one or more of the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form, for example, in capsules or cartridges of, for example, gelatin, or blister packs from which the powder may be administered by means of an inhaler.

The pharmaceutical preparations may be in unit dosage forms. In such form, the preparation may be subdivided into unit doses containing appropriate quantities of the active component. The unit dosage form can be a packaged preparation, such as a kit or other form, the package containing discrete quantities of preparation, such as packeted tablets, capsules, liquids or powders in vials or ampoules. Also, the unit dosage form can be a capsule, tablet, cachet, or lozenge, or it can be the appropriate number of any of these in packaged form.

The present disclosure is further illustrated by the following examples, which should not be construed as limiting in any way. The contents of all cited references throughout this application are hereby expressly incorporated by reference. The practice of the present invention will employ, unless otherwise indicated, conventional techniques of pharmacology and pharmaceutics, which are within the skill of the art.

EXAMPLES

Example 1

The RIG-I Like Receptor LGP2 Protects Tumor Cells from Ionizing Radiation

Methods

Gene Selection

We compiled 14 gene expression datasets containing interferon-stimulated genes in cancer cells as shown below in Table No. 1.

TABLE NO. 1

Fourteen Gene Expression Datasets

| PMID | Citation |
|---|---|
| 14755057 | Khodarev NN, et al. STAT1 is overexpressed in tumors selected for radioresistance and confers protection from radiation in transduced sensitive cells. *Proc Natl Acad Sci USA* (2004) 101(6): 1714-1719 |
| 15657362 | Becker M, et al. Distinct gene expression patterns in a tamoxifen-sensitive human mammary carcinoma xenograft and its tamoxifen-resistant subline MaCa 3366/TAM. Mol Cancer Ther (2005) Jan; 4(1): 151-68 |
| 16075456 | Pedersen MW, et al. Analysis of the epidermal growth factor receptor specific transcriptome: effect of receptor expression level and an activating mutation. J Cell Biochem 2005 Oct 1; 96(2): 412-27 |
| 16652143 | Patterson SG, et al. Novel role of Stat1 in the development of docetaxel resistance in prostate tumor cells. Oncogene 2006 Oct 5; 25(45): 6113-22 |
| 17072862 | Fryknas M, et al. STAT1 signaling is associated with acquired crossresistance to doxorubicin and radiation in myeloma cell lines. Int J Cancer 2007 Jan 1; 120(1): 189-95 |
| 17440099 | Tsai MH, et al. Gene expression profiling of breast, prostate, and glioma cells following single versus fractionated doses of radiation. Cancer Res 2007 Apr 15; 67(8): 3845-52 |
| 17868458 | Buess M, et al. Characterization of heterotypic interaction effects in vitro to deconvolute global gene expression profiles in cancer. Genome Biol 2007; 8(9): R191 |
| 20197756 | Meng Y, et al. Ad.Egr-TNF and local ionizing radiation suppress metastases by interferon-beta-dependent activation of antigen-specific CD8+ T cells. Mol Ther 2010 May; 18(5): 912-20 |
| 20682643 | Luszczek W, et al. Combinations of DNA methyltransferase and histone deacetylase inhibitors induce DNA damage in small cell lung cancer cells: correlation of resistance with IFN-stimulated gene expression. Mol Cancer Ther 2010 Aug; 9(8): 2309-21 |
| 20875954 | Dobbin E, et al. Proteomic analysis reveals a novel mechanism induced by the leukemic oncogene Tel/PDGFRβ in stem cells: activation of the interferon response pathways. Stem Cell Res 2010 Nov; 5(3): 226-43 |
| 21074499 | Chen E, et al. Distinct clinical phenotypes associated with JAK2V617F reflect differential STAT1 signaling. Cancer Cell 2010 Nov 16; 18(5): 524-35 |
| 21185374 | Englert NA, et al. Persistent and non-persistent changes in gene expression result from long-term estrogen exposure of MCF-7 breast cancer cells. J Steroid Biochem Mol Biol 2011 Feb; 123(3-5): 140-50 |
| 23056240 | Pitroda SP, et al. Tumor endothelial inflammation predicts clinical outcome in diverse human cancers. PLoS One 2012; 7(10): e46104 |
| NA | Khodarev NN, et al. (unpublished) |

Probe set IDs for each dataset were annotated using Ingenuity Pathway Analysis (IPA—www.ingenuity.com/). Genes were included in the final screening set if they were in the IRDS or if they were reported in ≥2 other studies. After initial inclusion, all selected genes were screened in the Interferome database (www.interferome.org/) to select genes activated by IFNs. In total, 89 candidate ISGs (Interferon Stimulated Genes) downstream from IFN/Stat were identified below in Table No. 2.

TABLE NO. 2

Identified Candidate ISGs

| Gene Symbol | Gene Name | Entrez Gene ID |
|---|---|---|
| ABCC3 | ATP-binding cassette, sub-family C (CFTR/MRP), member 3 | 8714 |
| B2M | beta-2-microglobulin | 567 |

TABLE NO. 2-continued

Identified Candidate ISGs

| Gene Symbol | Gene Name | Entrez Gene ID |
|---|---|---|
| BST2 | bone marrow stromal cell antigen 2 | 684 |
| CCL2 | chemokine (C-C motif) ligand 2 | 6347 |
| CCL5 | chemokine (C-C motif) ligand 5 | 6352 |
| CCNA1 | cyclin A1 | 8900 |
| CD74 | CD74 molecule, major histocompatibility complex, class II invariant chain | 972 |
| CMPK2 | cytidine monophosphate (UMP-CMP) kinase 2, mitochondrial | 129607 |
| CTSS | cathepsin S | 1520 |
| CXCL1 | chemokine (C—X—C motif) ligand 1 (melanoma growth stimulating activity, alpha) | 2919 |
| CXCL10 | chemokine (C—X—C motif) ligand 10 | 3627 |
| CXCL3 | chemokine (C—X—C motif) ligand 3 | 2921 |
| CXCL9 | chemokine (C—X—C motif) ligand 9 | 4283 |
| DAZ1 | deleted in azoospermia 1 | 1617 |
| DDX58 | DEAD (Asp-Glu-Ala-Asp) box polypeptide 58 | 23586 |
| DDX60 | DEAD (Asp-Glu-Ala-Asp) box polypeptide 60 | 55601 |
| DDX60L | DEAD (Asp-Glu-Ala-Asp) box polypeptide 60-like | 91351 |
| DHX58 (LGP2) | DEXH (Asp-Glu-X-His) box polypeptide 58 | 79132 |
| DTX3L | deltex 3-like (Drosophila) | 151636 |
| EIF2AK2 | eukaryotic translation initiation factor 2-alpha kinase 2 | 5610 |
| EPSTI1 | epithelial stromal interaction 1 (breast) | 94240 |
| GBP1 | guanylate binding protein 1, interferon-inducible, 67 kDa | 2633 |
| GBP2 | guanylate binding protein 2, interferon-inducible | 2634 |
| HERC5 | hect domain and RLD 5 | 51191 |
| HERC6 | hect domain and RLD 6 | 55008 |
| HNMT | histamine N-methyltransferase | 3176 |
| IFI16 | interferon, gamma-inducible protein 16 | 3428 |
| IFI27 | interferon, alpha-inducible protein 27 | 3429 |
| IFI35 | interferon-induced protein 35 | 3430 |
| IFI44 | interferon-induced protein 44 | 10561 |
| IFI44L | interferon-induced protein 44-like | 10964 |
| IFI6 | interferon, alpha-inducible protein 6 | 2537 |
| IFIH1 | interferon induced with helicase C domain 1 | 64135 |
| IFIT1 | interferon-induced protein with tetratricopeptide repeats 1 | 3434 |
| IFIT2 | interferon-induced protein with tetratricopeptide repeats 2 | 3433 |
| IFIT3 | interferon-induced protein with tetratricopeptide repeats 3 | 3437 |
| IFITM1 | interferon induced transmembrane protein 1 (9-27) | 8519 |
| IFITM2 | interferon induced transmembrane protein 2 (1-8D) | 10581 |
| IFITM3 | interferon induced transmembrane protein 3 (1-8U) | 10410 |
| IGFBP3 | insulin-like growth factor binding protein 3 | 3486 |
| IL7R | interleukin 7 receptor | 3575 |
| IRF1 | interferon regulatory factor 1 | 3659 |
| IRF7 | interferon regulatory factor 7 | 3665 |
| IRF9 | interferon regulatory factor 9 | 10379 |
| ISG15 | ISG15 ubiquitin-like modifier | 9636 |
| LAMP3 | lysosomal-associated membrane protein 3 | 27074 |
| LGALS3BP | lectin, galactoside-binding, soluble, 3 binding protein | 3959 |
| LY6E | lymphocyte antigen 6 complex, locus E | 4061 |
| LY96 | lymphocyte antigen 96 | 23643 |
| MARCKS | myristoylated alanine-rich protein kinase C substrate | 4082 |
| MCL1 | myeloid cell leukemia sequence 1 (BCL2-related) | 4170 |
| MGP | matrix Gla protein | 4256 |
| MX1 | myxovirus (influenza virus) resistance 1, interferon-inducible protein p78 (mouse) | 4599 |
| MX2 | myxovirus (influenza virus) resistance 2 (mouse) | 4600 |
| NLRC5 | NLR family, CARD domain containing 5 | 84166 |
| NMI | N-myc (and STAT) interactor | 9111 |
| OAS1 | 2',5'-oligoadenylate synthetase 1, 40/46 kDa | 4938 |
| OAS2 | 2'-5'-oligoadenylate synthetase 2, 69/71 kDa | 4939 |
| OAS3 | 2'-5'-oligoadenylate synthetase 3, 100 kDa | 4940 |
| OASL | 2'-5'-oligoadenylate synthetase-like | 8638 |
| PARP12 | poly (ADP-ribose) polymerase family, member 12 | 64761 |
| PLSCR1 | phospholipid scramblase 1 | 5359 |
| PRIC285 | peroxisomal proliferator-activated receptor A interacting complex 285 | 85441 |
| PSMB10 | proteasome (prosome, macropain) subunit, beta type, 10 | 5699 |
| PSMB8 | proteasome (prosome, macropain) subunit, beta type, 8 (large multifunctional peptidase 7) | 5696 |
| PSMB9 | proteasome (prosome, macropain) subunit, beta type, 9 (large multifunctional peptidase 2) | 5698 |
| RNF213 | ring finger protein 213 | 57674 |
| RSAD2 | radical S-adenosyl methionine domain containing 2 | 91543 |
| RTP4 | receptor (chemosensory) transporter protein 4 | 64108 |
| SAMD9 | sterile alpha motif domain containing 9 | 54809 |

TABLE NO. 2-continued

Identified Candidate ISGs

| Gene Symbol | Gene Name | Entrez Gene ID |
|---|---|---|
| SAMD9L | sterile alpha motif domain containing 9-like | 219285 |
| SAMHD1 | SAM domain and HD domain 1 | 25939 |
| SP110 | SP110 nuclear body protein | 3431 |
| SRGN | serglycin | 5552 |
| STAT1 | signal transducer and activator of transcription 1, 91 kDa | 6772 |
| TAGLN | transgelin | 6876 |
| TAP1 | transporter 1, ATP-binding cassette, sub-family B (MDR/TAP) | 6890 |
| THBS1 | thrombospondin 1 | 7057 |
| TIMP3 | TIMP metallopeptidase inhibitor 3 | 7078 |
| TNFSF10 | tumor necrosis factor (ligand) superfamily, member 10 | 8743 |
| TPD52L1 | tumor protein D52-like 1 | 7164 |
| TRIM14 | tripartite motif-containing 14 | 9830 |
| TRIM21 | tripartite motif-containing 21 | 6737 |
| UBA7 | ubiquitin-like modifier activating enzyme 7 | 7318 |
| UBE2L6 | ubiquitin-conjugating enzyme E2L 6 | 9246 |
| USP18 | ubiquitin specific peptidase 18 | 11274 |
| VAMP5 | vesicle-associated membrane protein 5 (myobrevin) | 10791 |
| WARS | tryptophanyl-tRNA synthetase | 7453 |
| XAF1 | XIAP associated factor 1 | 54739 | siRNA Screen siRNA screening of the selected ISGs was performed as follows. On day 1, Lipofectamine RNAiMAX diluted in Opti-MEM (Life Technologies) was added to 0.075 µL/well using a Tecan Freedom EVO 200 robotic liquid handling station to the previously prepared 384-well microplates (Corning/3712) containing immobilized individual siRNAs (Dharmacon siGENOME) plated in triplicate for each target ISG. Cells were added using a Thermo Electron MultiDrop Combi dispenser at 500 cells/well in 50 µL of RPMI 1640 media supplemented with 10% FCS. The final siRNA concentration in each well was 50 nM. Plates were incubated overnight at 37° C., and on day 2 were treated with IR at a dose of 3 Gy or untreated. Plates were further incubated at 37° C. and then assayed for viability at 48 hours post-IR using the highly sensitive luciferase-based CellTiterGlo® assay (Promega, Madison, Wis.). Luminescent reagent was added using a Thermo Electron MultiDrop Combi, and luminescent measurements were taken 90 minutes later using Molecular Devices Analyst GT. This platform was provided by the Cellular Screening Core (CSC), Institute for Genomics & Systems Biology, University of Chicago.

Individual siRNAs against LGP2 were validated in HCT116 and MCF10A cell lines by viability assay. Viability was assayed at 120 hours post-transfection (72 hours post-IR) using the CellTiter-Glo® Luminescent Cell Viability Assay (Promega, Madison, Wis.). This experiment was repeated to confirm reproducibility of the data. The top two siRNA's were selected for subsequent qRT-PCR experiments to confirm suppression of LGP2 mRNA on the basal level and after IFNβ treatment. Based on these data, two individual siRNA were selected and used in all subsequent experiments: #3: (SEQ ID NO: 1, 5'-CCAGUACCUA-GAACUUAA-3') and #4 (SEQ ID NO:2, 5'-AGAAUGAGCUGGCCCACUU-3')

Cell Cultures

B6 Wt and B6/IFNAR1−/− mice were generously provided by Yang-Xin Fu at the University of Chicago and used in accordance with the animal experimental guidelines set by the Institute of Animal Care and Use Committee. Primary murine embryonic fibroblasts (MEFs) were obtained from 13.5 d postcoitus embryos and cultivated in DMEM supplemented with 10% FBS, non-essential amino acids and penicillin/streptomycin for no more than 7 passages as previously described. MEFs were immortalized with a retrovirus expressing SV40-large T antigen (Addgene plasmid 13970. Tumor cell lines used for siRNA screen and subsequent experiments were: Scc61 and Nu61 (head and neck squamous cell carcinoma); D54, T98G and U251 (glioblastoma multiforme); WiDr and HCT116 (colorectal carcinoma); MDA-MB-231 and MCF7 (breast adenocarcinoma); MCF10a (immortalized human mammary epithelial cells); DU154 (prostate cancer); A549 and NCI-H460 (lung adenocarcinoma); and T24 (bladder cancer). Cell lines were cultivated as follows: Scc61 and Nu61 in DMEM/F12 with 20% FBS, 1% P/S, and 1% HC; D54, T98G and WiDr in MEM with 10% FBS and 1% P/S; U251, HCT116, MDA-MB-231, MCF7, in DMEM high glucose with 10% FBS and 1% P/S; MCF10A MEBM with MEGM kit (ATCC), cholera toxin (100 ng/mL), and 1% P/S; DU145 in DMEM F12 with 10% FBS and 1% P/S; A549 and NCI-H460 in RPMI with 10% FBS and 1% P/S; T24 in McCoy's 5A Medium with 10% FBS and 1% P/S.

Retro- and Lentiviral Production and Transduction

Retrovirus was produced using complete packaging ecotropic Plat-E cells (Cell Biolabs) by FUGENE mediated transfection of pBABE-puro SV40 LT (Zhao J J, et al. (2003) Human mammary epithelial cell transformation through the activation of phosphatidylinositol 3-kinase. *Cancer cell* 3(5):483-495). Lentivirus was produced by co-transfection of VSVG, VPR and pLKO.1 lentiviral vector with inserted LGP2 shRNA sequence (SEQ ID NO:3, ATTCTTGCGGTCATCGAACAG, Thermo Scientific) or non-targeting control (Thermo Scientific) into HEK293X cells. Supernatants containing infectious viral particles were harvested 48 h post-transfection and passed through a 0.45 µm filter. Infections of exponentially growing cells were performed with virus-containing supernatant supplemented with 8 µg/mL polybrene. In lentiviral shRNA experiments, transduced cells were continually selected in the presence of puromycin (1-2 µg/ml).

Western Blotting

Western blotting was performed as described previously (Khodarev N N, et al. (2007) Signal transducer and activator of transcription 1 regulates both cytotoxic and prosurvival functions in tumor cells. *Cancer Res* 67(19):9214-9220).

The following antibodies were utilized: anti-LGP2 (sc134667; Santa Cruz) (1:1,000) and anti-Actin-HRP (Sc47778, Santa Cruz) (1:5000). Secondary antibodies conjugated to horseradish peroxidase (HRP) (Santa Cruz) were used at 1:10,000. Experimental findings were confirmed in at least three independent experiments.

qRT-PCR

Total RNA was extracted using TRIzol reagent (Invitrogen), treated with DNase I (Invitrogen) and reverse transcribed using SuperScript III (Invitrogen), and the cDNA products were resuspended in 20 µl of $H_2O$ and used for PCR with Fast SYBR green master mix and a StepOnePlus real-time PCR system (both from Applied Biosystems). The following human gene-specific primers were used: IFNβ sense primer 5'-AACTTTGACATCCCTGAGGAGATT-3' (SEQ ID NO:4) and antisense primer 5'-GCGGCGTCCTC-CTTCTG-3'(SEQ ID NO:5); GAPDH sense 5'-CTCT-GCTCCTCCTGTTCGAC-3'(SEQ ID NO:6) and antisense 5'-GTTAAAAGCAGCCCTGGTGA-3'(SEQ ID NO:7). All samples were amplified in duplicate and every experiment was repeated independently at least two times. Relative gene expression was determined using the $2^{-\Delta\Delta CT}$ method, with GAPDH as the internal control.

Luciferase Assay

To measure IFNβ promoter activity, HEK293 cells were transiently co-transfected using Fugene (Roche) with pGL3-Ifnβ-Luc (Lin R, Genin P, Mamane Y, & Hiscott J (2000) Selective DNA binding and association with the CREB binding protein coactivator contribute to differential activation of alpha/beta interferon genes by interferon regulatory factors 3 and 7. *Molecular and cellular biology* 20(17): 6342-6353) and an expression plasmid carrying the Renilla luciferase gene driven by the SV40 promoter (Promega). In some experiments, co-transfection mixes also included p3xFLAG-CMV10-LGP2 (Bamming D & Horvath C M (2009) Regulation of signal transduction by enzymatically inactive antiviral RNA helicase proteins MDA5, RIG-I, and LGP2. *J Biol Chem* 284(15):9700-9712) expression plasmid (or p3xFLAG-CMV10control). The following day, cells were irradiated at indicated dose and collected at indicated time in passive lysis buffer (Promega). Firefly and Renilla luciferase activities were measured using a dual-luciferase assay system (Promega). For siRNAs experiments, siRNA against LGP2 (see above) or non-targeting (Dharmacon) were transfected with RNAimax 24 h prior to transfection of luciferase/Renilla plasmids. Mean luciferase values were normalized and quantified from duplicate runs for each of at least three separate experiments.

Viability Assay

To determine cell viability, cells were plated in triplicate in 96-well plates at a density of 3,000 cells per well and treated with increasing amounts of ionizing radiation. At the indicated time, cells were stained using 0.4% methylene blue in 50% methanol (Leonova K I, et al. (2013) p53 cooperates with DNA methylation and a suicidal interferon response to maintain epigenetic silencing of repeats and noncoding RNAs. *Proc Natl Acad Sci USA* 110(1):E89-98). Dye was extracted from stained cells using 3% HCl solution for spectrophotometric quantitation at 660 nm. In some experiments, neutralizing antibodies to IFNβ (PBL Interferon Source, 1 µg/mL) or isotype control $IgG_1$ (RD Systems) were incubated with cells 1 h prior irradiation.

Clonogenic Assay

Cells were seeded to form colonies in p60 plates and treated the next day with 1, 3, 5, or 7 Gy IR. When sufficiently large colonies with at least 50 cells were visible (approximately 12-15 days), the plates were fixed with methanol and stained with crystal violet as previously described. Colonies with more than 50 cells were counted and the surviving fraction was calculated (Mauceri H J, et al. (1998) Combined effects of angiostatin and ionizing radiation in antitumour therapy. *Nature* 394(6690):287-291). For siRNAs experiments, the indicated siRNA was transfected 24 h prior to plating for the clonogenic assay. In overexpression experiments, D54 cells were transfected with p3xFLAG-CMV10 or p3xFLAG-CMV10-LGP2, selected in G418 for two weeks (200 µg/mL) and individual clones were verified for stable LGP2 expression and assessed in clonogenic assays.

Flow cytometric analysis. Single-cell suspensions of cells were isolated and incubated with anti-annexin V and propidium iodide according to the manufacturer's instructions (Annexin V Apoptosis Detection Kit, eBioscience). Samples were analyzed on a FACSCanto flow cytometer (BD Biosciences), and data were analyzed with FlowJo software (TreeStar, Inc.).

Statistical Analysis

A. siRNA Screen Analysis.

For each of the basal level and IR screens, the intensities of the plate were first log 2 transformed and then normalized with normalized percent inhibition (NPI) method to correct for plate effect. The normalized intensities were further divided by the per-plate median absolute deviations (MAD) in order to adjust the variance. The procedures were performed using Bioconductor package cellHTS2 (Boutros M, Bras L P, & Huber W (2006) Analysis of cell-based RNAi screens. *Genome biology* 7(7):R66). To identify the genes that lead to the most consistent decrement in cell viability when suppressed across 14 cell lines, we conducted a rank aggregation on the gene rank lists obtained from basal level and IR screens, separately. The Robust Rank Aggregation (RAA) algorithm implemented in R package RobustRank-Aggreg was applied (Kolde R, Laur S, Adler P, & Vilo J (2012) Robust rank aggregation for gene list integration and meta-analysis. *Bioinformatics* 28(4):573-580). Briefly, the RRA method assumes a null model where the ranks of each gene are uniformly distributed over the rank lists. For each plate, the 89 genes were sorted in descending order of their median normalized intensity of the three replicates. Then for each position in the sorted list, the probability that a randomly sampled rank from the null model has a lower rank value than the value at that position in the sorted list can be calculated. The minimum of the resulting probabilities over all positions in the sorted list is defined as the rank score of the gene, which can then be converted into an estimated P-value of the gene through Bonferroni correction (Dunn O J (1961) Multiple Comparisons Among Means. *Journal of the American Statistical Association* 56(293):52-64). The derived P-values are subject to multiple testing correction to control the false discovery rate (FDR) by Benjamini-Hochberg procedure (Benjamini Y & Hochberg Y (1995) Controlling the False Discovery Rate—a Practical and Powerful Approach to Multiple Testing. *J Roy Stat Soc B Met* 57(1): 289-300). To further evaluate the stability of Bonferroni corrected P-values, we applied leave-one-out permutation test on the robust rank aggregation algorithm (Vosa U, et al. (2013) Meta-analysis of microRNA expression in lung cancer. *International Journal of Cancer* 132(12):2884-2893.). The analysis was conducted by performing RRA on a subset of 14 gene lists with one randomly selected list excluded. The procedure was repeated 100,000 times and the P-values from each permutation for each gene were then averaged.

B. Database Analysis.

Glioblastoma datasets were collected from the Cancer Genome Atlas (CGA) (n=382) and Phillips et al. study (n=77) (Phillips H S, et al. (2006) Molecular subclasses of high-grade glioma predict prognosis, delineate a pattern of disease progression, and resemble stages in neurogenesis. *Cancer cell* 9(3):157-173). Only patients with a history of prior radiation therapy were included in the analysis. mRNA expression values were normalized to the median value across all patient samples within each respective dataset. Gene expression data were visualized using hierarchical clustering. ISG expression was based on the mRNA expression of interferon-inducible genes as reviewed in (Khodarev N R, B, Weichselbaum, R (2012) Molecular Pathways: Interferon/Stat1 pathway: role in the tumor resistance to genotoxic stress and aggressive growth *Clinical Cancer Research* 18(11):1-7). Kaplan-Meier survival analysis with a log-rank test was used to compare overall survival for LGP2-positive patients, defined as 1.5-fold increased expression above the group median, versus LGP2-negative patients. Cox proportional hazard analysis of overall survival was performed to determine the hazard ratio for overall survival of LGP2-positiveversus LGP2-negative patients. All analyses were performed using JMP 9.0 (SAS Institute Inc.; Cary, N.C.). A p-value≤0.05 was considered statistically significant.

C. Quantitative Data Analysis.

Data are presented as means±standard deviations (SD) for three or more representative experiments. Statistical significance was calculated using Student's t test.

Discussion

Several studies have shown that the response of tumor cells to ionizing radiation (IR) is associated with Interferon (IFN)-mediated signaling (Khodarev N N, et al. (2004) STAT1 is overexpressed in tumors selected for radioresistance and confers protection from radiation in transduced sensitive cells. *Proc Natl Acad Sci USA* 101(6):1714-1719; Khodarev N N, et al. (2007) Signal transducer and activator of transcription 1 regulates both cytotoxic and prosurvival functions in tumor cells. *Cancer Res* 67(19):9214-9220; Tsai M H, et al. (2007) Gene expression profiling of breast, prostate, and glioma cells following single versus fractionated doses of radiation. *Cancer Res* 67(8):3845-3852; John-Aryankalayil M, et al. (2010) Fractionated radiation therapy can induce a molecular profile for therapeutic targeting. *Radiat Res* 174(4):446-458; Cheon H, Yang J, & Stark G R (2011) The functions of signal transducers and activators of transcriptions 1 and 3 as cytokine-inducible proteins. *J Interferon Cytokine Res* 31(1):33-40; Amundson S A, et al. (2004) Human in vivo radiation-induced biomarkers: gene expression changes in radiotherapy patients. *Cancer Res* 64(18):6368-6371). IFN signaling leads to the induction of multiple Interferon-Stimulated Genes (ISGs) (Borden E C, et al. (2007) Interferons at age 50: past, current and future impact on biomedicine. *Nat Rev Drug Discov* 6(12):975-990; Samuel C E (2001) Antiviral actions of interferons. *Clin Microbiol Rev* 14(4):778-809, table of contents), and activates growth arrest and cell death in exposed cell populations (Kotredes K P & Gamero A M (Interferons as inducers of apoptosis in malignant cells. *J Interferon Cytokine Res* 33(4):162-170). However, the precise mechanism of IR-mediated induction of IFN signaling is unknown. Tumor cell clones that survive an initial cytotoxic insult are subsequently resistant to exposure to both IR and pro-death components of IFN signaling (Khodarev N R, B, Weichselbaum, R (2012) Molecular Pathways: Interferon/Stat1 pathway: role in the tumor resistance to genotoxic stress and aggressive growth *Clinical Cancer Research* 18(11):1-7). These clones express IFN dependent enhanced levels of constitutively expressed ISGs, which overlap in part with ISGs initially induced by cytotoxic stress. Many of these constitutively expressed ISGs have been characterized as anti-viral genes (Perou C M, et al. (1999) Distinctive gene expression patterns in human mammary epithelial cells and breast cancers. *Proc Natl Acad Sci USA* 96(16):9212-9217). Recently, enhanced levels of constitutively expressed ISGs have been reported in advanced cancers and were often associated with a poor prognosis related to aggressive tumor growth, metastatic spread, resistance to a IR/chemotherapy, or combinations of these factors (Perou C M, et al. (1999) Distinctive gene expression patterns in human mammary epithelial cells and breast cancers. *Proc Natl Acad Sci USA* 96 (16):9212-9217; Weichselbaum R R, et al. (2008) An interferon-related gene signature for DNA damage resistance is a predictive marker for chemotherapy and radiation for breast cancer. *Proc Natl Acad Sci USA* 105(47):18490-18495; Martin D N, Starks A M, & Ambs S (Biological determinants of health disparities in prostate cancer. *Curr Opin Oncol* 25(3):235-241; Duarte C W, et al. (Expression signature of IFN/STAT1 signaling genes predicts poor survival outcome in glioblastoma multiforme in a subtype-specific manner. *PLoS One* 7(1):e29653; Hix L M, et al. (Tumor STAT1 transcription factor activity enhances breast tumor growth and immune suppression mediated by myeloid-derived suppressor cells. *J Biol Chem* 288(17):11676-11688; Haricharan S & Li Y (STAT signaling in mammary gland differentiation, cell survival and tumorigenesis. *Mol Cell Endocrinol*; Camicia R, et al. (BAL1/ARTD9 represses the anti-proliferative and pro-apoptotic IFNgamma-STAT1-IRF1-p53 axis in diffuse large B-cell lymphoma. *J Cell Sci* 126(Pt 9):1969-1980). The studies presented herein are based on the hypothesis that a specific set of constitutively expressed ISGs, whose enhanced expression by cytotoxic stress, confers a selective advantage to individual tumor clones (Cheon H, Yang J, & Stark G R (2011) The functions of signal transducers and activators of transcriptions 1 and 3 as cytokine-inducible proteins. *J Interferon Cytokine Res* 31(1):33-40.; Kotredes K P & Gamero A M (Interferons as inducers of apoptosis in malignant cells. *J Interferon Cytokine Res* 33(4): 162-170; Khodarev N R, B, Weichselbaum, R (2012) Molecular Pathways: Interferon/Stat1 pathway: role in the tumor resistance to genotoxic stress and aggressive growth *Clinical Cancer Research* 18(11):1-7; Weichselbaum R R, et al. (2008) An interferon-related gene signature for DNA damage resistance is a predictive marker for chemotherapy and radiation for breast cancer. *Proc Natl Acad Sci USA* 105(47):18490-18495; Cheon H, et al. (2013) IFNbeta-dependent increases in STAT1, STAT2, and IRF9 mediate resistance to viruses and DNA damage. *The EMBO journal* 32(20):2751-2763).

To test this hypothesis, we designed a targeted siRNA screen against 89 ISGs selected from 2 sources. The first included ISGs identified in our earlier screen and designated the Interferon-Related DNA Damage Signature (IRDS) (Khodarev N N, et al. (2004) STAT1 is overexpressed in tumors selected for radioresistance and confers protection from radiation in transduced sensitive cells. *Proc Natl Acad Sci USA* 101(6):1714-1719; Weichselbaum R R, et al. (2008) An interferon-related gene signature for DNA damage resistance is a predictive marker for chemotherapy and radiation for breast cancer. *Proc Natl Acad Sci USA* 105(47):18490-18495). The second set included related ISG signatures that have been reported in the literature (as described above in Methods and in Table No. 1). The 89 genes were individually targeted in 14 tumor cell lines derived from malignant gliomas, lung, breast, colon, head and neck, prostate and bladder cancers.

One of our most significant finding from this screen was that the RNA helicase LGP2 (DHX58) confers survival and mediates the response to IR of multiple tumor cell lines. LGP2, an abbreviation of Laboratory of Genetics and Physiology 2, acts as a suppressor of the RNA-activated cytoplasmic RIG-1-like receptors pathway (Malur M, Gale M, Jr., & Krug R M (2013) LGP2 downregulates interferon production during infection with seasonal human influenza A viruses that activate interferon regulatory factor 3. *J Virol* 86(19):10733-10738; Komuro A & Horvath C M (2006) RNA- and virus-independent inhibition of antiviral signaling by RNA helicase LGP2. *J Virol* 80(24):12332-12342). This pathway is a subtype of pattern recognition receptors responsible for primary recognition of pathogen and host-associated molecular patterns and the subsequent activation of Type I interferon production that orchestrates an innate immune response (Akira S, Uematsu S, & Takeuchi O (2006) Pathogen recognition and innate immunity. *Cell* 124(4):783-801; Kawasaki T, Kawai T, & Akira S (2011) Recognition of nucleic acids by pattern-recognition receptors and its relevance in autoimmunity. *Immunol Rev* 243 (1):61-73; Multhoff G & Radons J (2012) Radiation, inflammation, and immune responses in cancer. *Front Oncol* 2:58). In addition to its role in inhibiting IFNβ expression, Suthar et al. recently demonstrated that LGP2 governs CD8$^+$ T cell fitness and survival by inhibiting death-receptor signaling (Suthar M S, et al. (2012) The RIG-I-like receptor LGP2 controls CD8(+) T cell survival and fitness. *Immunity* 37(2): 235-248). Here we demonstrate that suppression of LGP2 leads to an enhanced IFNβ expression and increased killing of tumor cells. Our results thereby provide the first mechanistic connection between IR-induced cytotoxic response in tumor cells and the LGP2-IFNβ pathway.

An siRNA screen targeting 89 Interferon Stimulated Genes (ISGs) in 14 different cancer cell lines pointed to the RIG-I-like receptor LGP2 (Laboratory of Genetics and Physiology 2, also RNA helicase DHX58) as playing a key role in conferring tumor cell survival following cytotoxic stress induced by ionizing irradiation (IR). Studies on the role of LGP2 revealed the following; (i) Depletion of LGP2 in 3 cancer cells lines resulted in significant increase in cell death following IR, (ii) Ectopic expression of LGP2 in cells increased resistance to IR, and (iii) IR induced enhanced LGP2 expression in 3 cell lines tested.

Our studies designed to define the mechanism by which LGP2 acts point to its role in regulation of IFNβ. Specifically, (i) Suppression of LGP2 leads to enhanced IFNβ, (ii) Cytotoxic effects following IR correlated with expression of IFNβ inasmuch as inhibition of IFNβ by neutralizing antibody conferred resistance to cell death, and (iii) Mouse embryonic fibroblasts (MEFs) from IFN Receptor 1 knockout mice (IFNAR1$^{-/-}$) are radioresistant compared to wild-type MEFs. The role of LGP2 in cancer may be inferred from cumulative data showing elevated levels of LGP2 in cancer cells are associated with more adverse clinical outcomes. Our results below indicate that cytotoxic stress exemplified by IR induces IFNβ and enhances the expression of LGP2. Enhanced expression of LGP2 suppresses the ISGs associated with cytotoxic stress by turning off the expression of IFNβ.

Results

Expression of LGP2 is Associated with Tumor Cell Survival.

On the basis of our earlier studies (Khodarev N N, et al. (2004) STAT1 is overexpressed in tumors selected for radioresistance and confers protection from radiation in transduced sensitive cells. *Proc Natl Acad Sci USA* 101(6): 1714-1719; Khodarev N N, et al. (2007) Signal transducer and activator of transcription 1 regulates both cytotoxic and prosurvival functions in tumor cells. *Cancer Res* 67(19): 9214-9220; Weichselbaum R R, et al. (2008) An interferon-related gene signature for DNA damage resistance is a predictive marker for chemotherapy and radiation for breast cancer. *Proc Natl Acad Sci USA* 105(47):18490-18495; Khodarev N N, et al. (2009) STAT1 pathway mediates amplification of metastatic potential and resistance to therapy. *PLoS One* 4(6):e5821), we hypothesized the existence of ISGs that are constitutively expressed in aggressive cancers and confer pro-survival functions following cytotoxic stress caused by DNA damaging agents. To identify the key members of this group, we compiled a list of ISGs associated with aggressive tumors from multiple published studies (see Table No. 1). In total, 89 genes identified in Table No. 2 were selected for further evaluation based on either inclusion in the IRDS (Weichselbaum R R, et al. (2008) An interferon-related gene signature for DNA damage resistance is a predictive marker for chemotherapy and radiation for breast cancer. *Proc Natl Acad Sci USA* 105 (47):18490-18495) or inclusion in at least two reported ISG-related signatures. To test whether expression of these genes conferred a survival advantage to tumor cells we performed a targeted siRNA screen in a panel of 14 cell lines consisting of 2 lung cancer, 3 high grade glioma, 3 breast cancer and normal breast epithelium, 2 colon cancer, 2 head and neck cancer, 1 bladder cancer, and 1 prostate cancer cell lines. Each tumor cell line, both untreated and after exposure to 3 Gy, was targeted with pooled siRNAs against each of the selected 89 genes and scored on the basis of cell viability. To identify genes with pro-survival functions common across multiple cell lines tested we used a rank aggregation approach assuming each cell line was an independent dataset (Adler P, et al. (2009) Mining for coexpression across hundreds of datasets using novel rank aggregation and visualization methods. *Genome biology* 10(12):R139; Boulesteix A L & Slawski M (2009) Stability and aggregation of ranked gene lists. *Briefings in bioinformatics* 10(5):556-568). With different modes of normalizations and perturbations LGP2 was invariably the top ranked gene in unirradiated cells (See FIG. 1). In addition, LGP2 was among the top ranked genes conferring survival to multiple cancer cell lines after irradiation at 3 Gy. The focus of this report is on the role of LGP2 in the regulation of cell survival.

LGP2 Blocks Apoptosis Induced by IR.

Figure 2A:
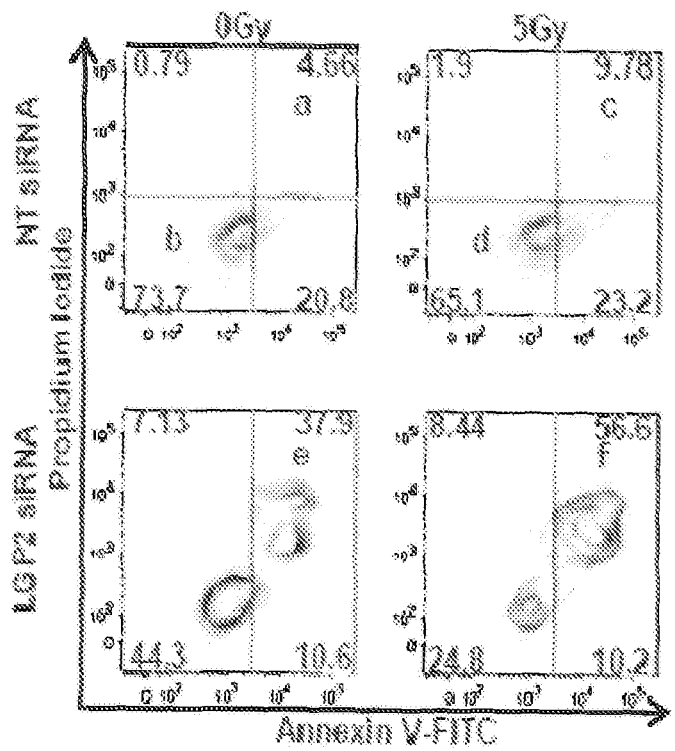
FIGS. 2A, 2B, 2C and 2D show knockdown of LGP2 enhances radiation-induced killing. Cell death was quantified by flow cytometric analysis using Annexin-V and propidium iodide staining. Tumor cells were treated with IR (5 Gy) 24 h post-transfection with indicated siRNA.
Figure 2B:
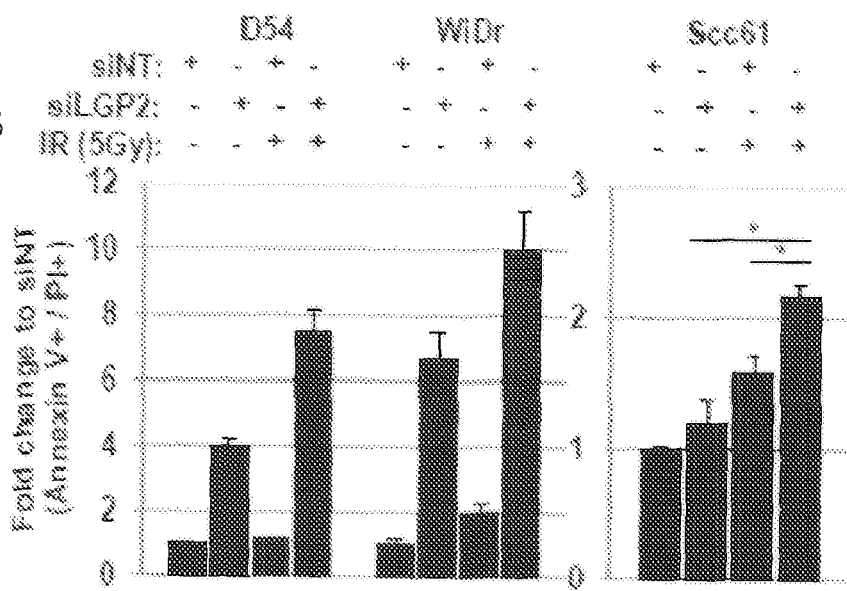

The desirable endpoint of radiotherapy is induction of apoptosis in irradiated cells. To define the role of LGP2 in determination of the outcome of IR treatment we tested the effects of depletion of LGP2 on induction of apoptosis by IR in WiDr, D54, and Scc61 cancer cell lines. As detailed in Methods and in the figure legends the cell lines were transfected with non-targeted (scrambled) siRNA (siNT) or targeted (siLGP2) siRNA and either mock-irradiated or irradiated (5 Gy) 24 hrs after transfection. The cells were stained with Annexin V and propidium iodide and scored for both markers by flow cytometry 48 hours after IR or mock treatment. The results were as follows:

As shown in FIG. 2A and in FIG. 2B, transfection of WiDr cells with a non-targeting (scrambled) siRNA (siNT) led to a small (4.66%) increase in double-positive cells (FIG. 2A, panel a), while 73.7% of the cell population remained viable under these conditions (FIG. 2A, panel b). Irradiation of siNT-transfected cells led to an approximately 2-fold increase in cell death (9.8%) with an 8.6% reduction in viable cells (65.1%) (FIG. 2A, panels c and d, respectively). Suppression of LGP2 alone led to an increase in double-positive cells to 37.9% (8.1-fold increase) (FIG. 2A panel e). The combination of LGP2 suppression followed by irradiation led to further accumulation of double-positive cells to 56.6%; a 12.1-fold increase relative to the non-irradiated siNT control (FIG. 2A, panel f).

Figure 2C:
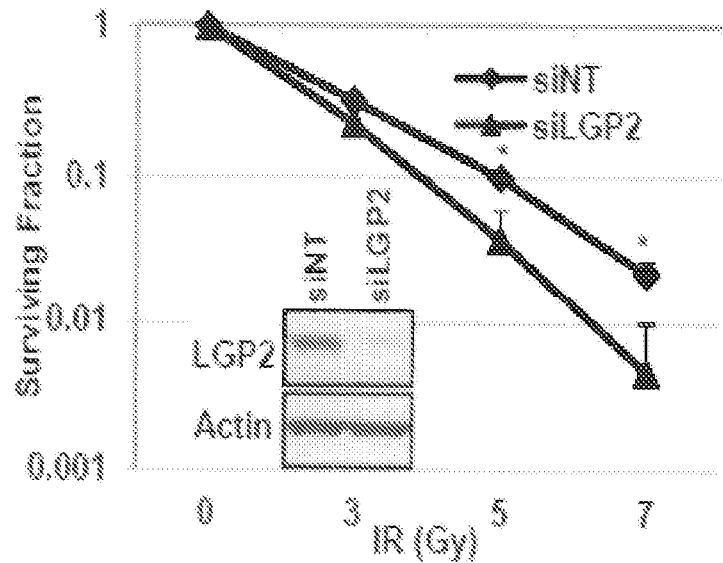
Figure 2D:
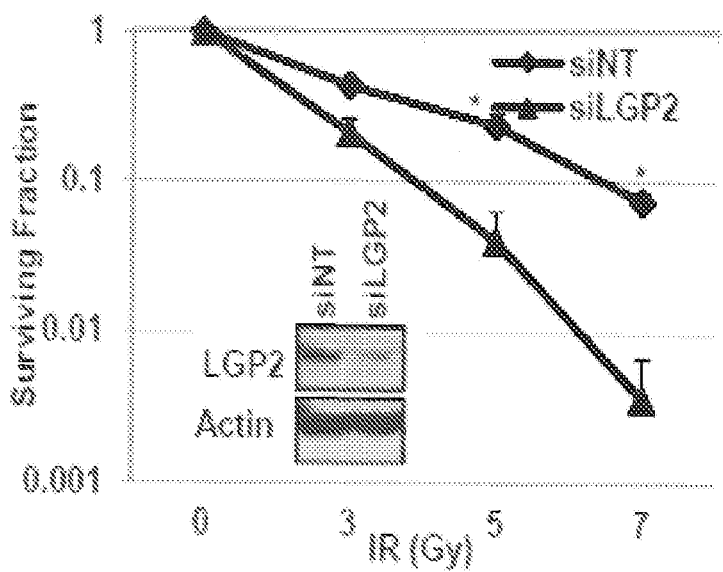

Similar data were obtained with D54 and Scc61 cells (FIG. 2B). As shown in FIG. 2B (left panel), siRNA knockdown of LGP2 in the D54 cells led to a 4-fold increase in cell death at baseline and a 7.5-fold increase following irradiation. The same conditions led to 6.4-fold cell death at baseline and 10-fold induction following IR in the WiDr cell line (FIG. 2B, left panel). A similar pattern was found in the Scc61 cell line (FIG. 2B, right panel, p<0.05). Clonogenic survival analyses revealed that siRNA-mediated depletion of LGP2 reduced radioresistance in both D54 and Scc61 cell lines. Compared to siNT control, irradiation of LGP2 depleted cells lead to 4.7 fold decrease in the survival fraction in D54 cells (p=0.014) and a 20.3-fold decrease in the survival fraction of Scc61 cells (p=0.00056) at 7 Gy (FIGS. 2C and D, respectively). We conclude that suppression of LGP2 results in apoptosis and radiosensitization.

Overexpression of LGP2 Protects Cells from IR.

Figure 3A:
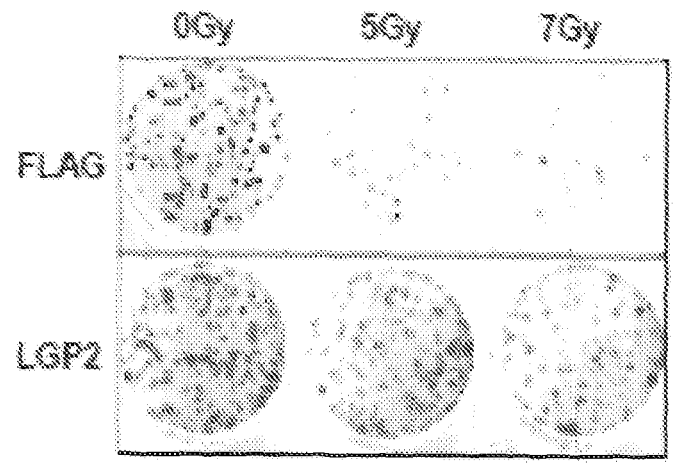
FIGS. 3A and 3B show overexpression of LGP2 inhibits radiation-induced killing. D54 cells were stably transfected by full-size p3xFLAG-CMV10-LGP2 (LGP2) or control p3xFLAG-CMB10 (Flag). Selected clones were propagated, plated in 6-well plates and irradiated at 0, 5 and 7 Gy.
Figure 3B:
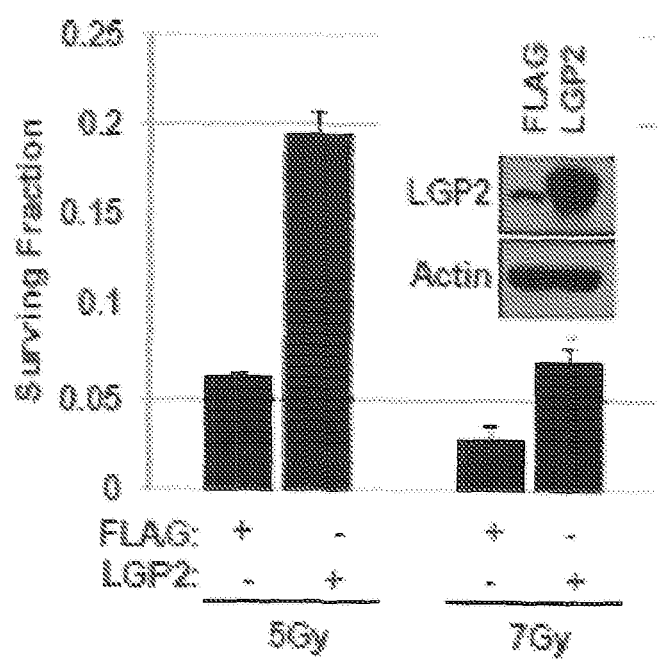

To verify the conclusion that LGP2 protects tumor cells cytotoxic effects of radiotherapy, we investigated the clonogenic survival of tumor cells expressing the full-length cDNA of LGP2. In this experiment, D54 cells were stably transfected with the plasmid p3xFLAG-CMV10-LGP2 encoding LGP2 or control p3xFLAG-CMV10 (Flag). Positive clones were plated in 6-well plates and exposed to 0, 5 or 7 Gy. The amounts of LGP2 protein in mock (Flag) transfected and LGP2 transfected cells are shown in the insert in FIG. 3B. FIG. 3A shows the surviving cell colonies stained with crystal violet 12 days after irradiation. Panel B shows the fraction of mock-transfected and LGP2-transfected cells that survived exposure to IR quantified as described in materials and methods. We conclude that ectopic expression of LGP2 confers increased resistance to IR.

IR Induces Expression of LGP2.

Figure 4:
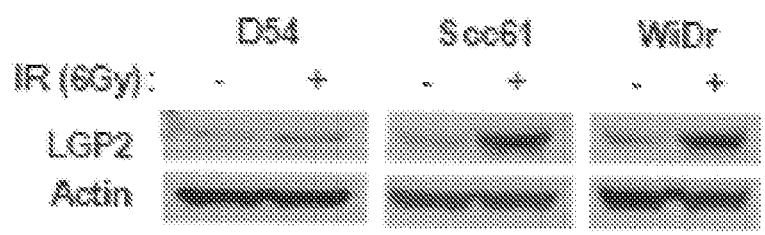
FIG. 4 shows that LGP2 is radioinducible. D54, WiDr and Scc61 cells were irradiated at 6 Gy; 72 hours post-IR cells lysates were analyzed by Western blotting.

We next asked if exposure to IR would up-regulate LGP2 expression in tumor cells. In this experiment D54, Scc61 and WiDr cells were mock-treated or exposed to 6 Gy. The cells were harvested 72 hrs after IR, solubilized, and tested for the presence of LGP2 by immunoblotting with anti-LGP2 antibody; Actin served as loading control. As shown in FIG. 4, a significant increase in LGP2 expression was observed in IR treated cells. We conclude that IR induces the expression of LGP2.

IR Induces Cytotoxic Type I IFN.

Figure 5A:
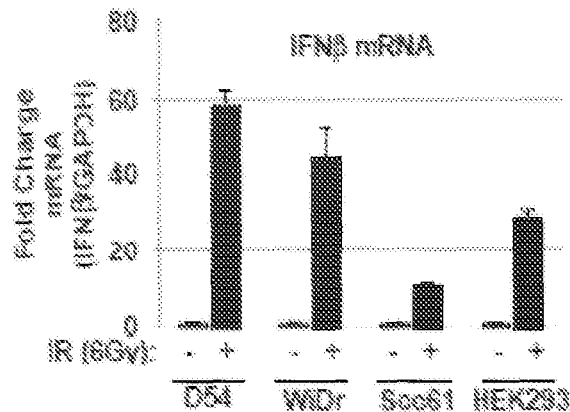
FIGS. 5A, 5B, and 5C show that IR induces cytotoxic IFNβ response.
Figure 5B:
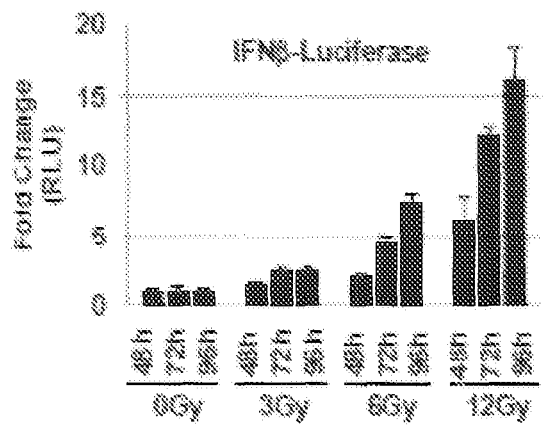

LGP2 functions to suppress Type I IFN production in response to viral infection or transfection of double-stranded RNA mimetics (Komuro A & Horvath C M (2006) RNA- and virus-independent inhibition of antiviral signaling by RNA helicase LGP2. *J Virol* 80(24):12332-12342; Saito T, et al. (2007) Regulation of innate antiviral defenses through a shared repressor domain in RIG-I and LGP2. *Proc Natl Acad Sci USA* 104(2):582-587; Yoneyama M, et al. (2005) Shared and unique functions of the DExD/H-box helicases RIG-I, MDA5, and LGP2 in antiviral innate immunity. *Journal of immunology* 175(5):2851-2858; Komuro A, Bamming D, & Horvath C M (2008) Negative regulation of cytoplasmic RNA-mediated antiviral signaling. *Cytokine* 43(3):350-358; Rothenfusser S, et al. (2005) The RNA helicase Lgp2 inhibits TLR-independent sensing of viral replication by retinoic acid-inducible gene-I. *Journal of immunology* 175(8):5260-5268). The objective of the studies described in this section was to determine whether IR induces a Type 1 IFN response. In these studies D54, WiDr, Scc61 or HEK293 cells were mock-treated or exposed to 6 Gy. The cells were harvested 72 hrs after IR, and IFNβ expression relative to GAPDH was determined by real time-PCR. As shown in FIG. 5A, exposure to IR increased the relative expression of IFNβ mRNA in D54, WiDR, SCC61 and HEK293 cell lines by 58, 42, 12 and 28-fold respectively. In a complementary approach, we investigated the ability of IR to activate a plasmid reporter under the control of IFNβ promoter (IFNβ-Luc) (Lin R, Genin P, Mamane Y, & Hiscott J (2000) Selective DNA binding and association with the CREB binding protein coactivator contribute to differential activation of alpha/beta interferon genes by interferon regulatory factors 3 and 7. *Molecular and cellular biology* 20(17):6342-6353). In these experiments HEK293 cells were co-transfected with IFNβ-Luc and pRL-SV40. At 24 hrs after transfection, cells were mock-treated or exposed to 3, 6, or 12 Gy. Cells were harvested 48, 72 or 96 hrs and analyzed for dual luciferase activity. As shown in FIG. 5B, IR activated IFNβ expression in a dose- and time-dependent manner.

Figure 5C:
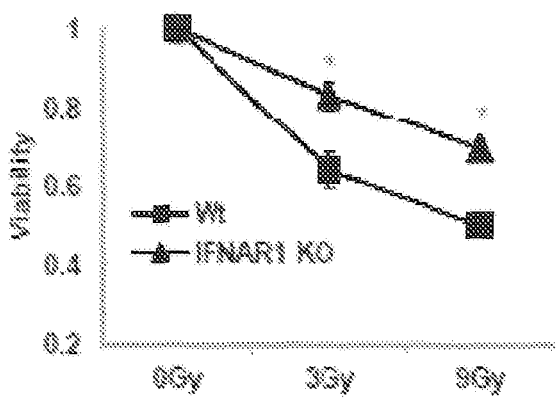

To determine if induction of IFNβ by IR was cytotoxic, we determined the relative radiosensitivity of immortalized murine embryo fibroblasts lacking the Type I IFN receptor 1 (IFNAR1$^{-/-}$) as compare to wild type MEFs (Wt). In this experiments, IFNAR1$^{-/-}$ and Wt MEFs were mock-treated or exposed to 3 or 9 Gy. Cells were assessed for viability 96 hrs after IR as described in Material and Methods. FIG. 5C shows that IFNAR1$^{-/-}$ MEFs are radioresistant as compared to Wt MEFs. We conclude that IR induces the production of cytotoxic Type I Interferon.

Depletion of LGP2 Enhances IFNβ-Dependent Cytotoxicity.

Figure 6A:
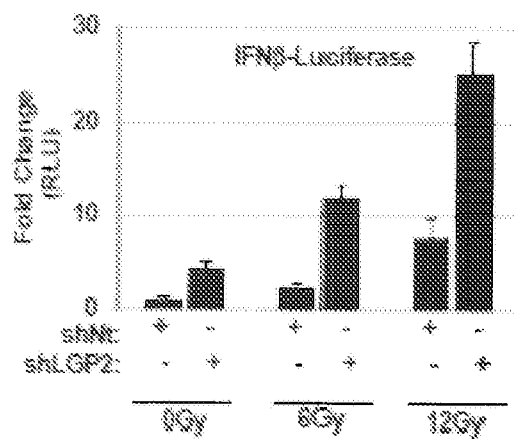
FIGS. 6A and 6B show that LGP2 inhibits IR-induced cytotoxic IFNβ.

We next assessed the role of LGP2 in regulating the IR-induced IFNβ response. HEK293 cells were transduced with lentiviral shRNA to stably reduce the levels of LGP2 or control non-targeting (shNT). Stably transduced cells were co-transfected with IFNβ-Luc and pRL-SV40, mock-treated or exposed to 6 or 12 Gy and collected 72 hrs after IR. Suppression of LGP2 led to a significant increase in IFNβ reporter activity at mock-treated and greatly increased IR-induced IFNβ (FIG. 6A).

Figure 6B:
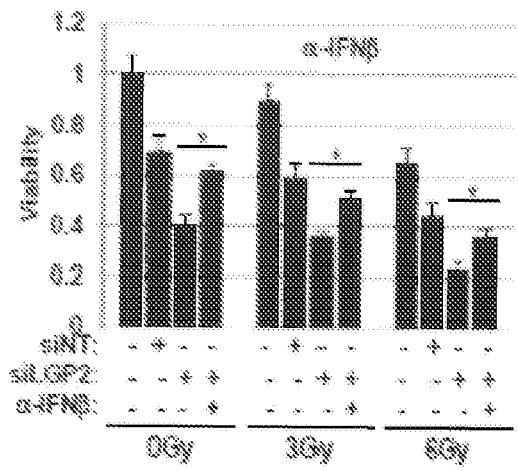

We next examined whether the radiosensitizing effects of LGP2 depletion were associated with a release of cytotoxic IFNβ. In this experiment, D54 cells were incubated with neutralizing antibodies against IFNβ and mock treated or exposed to 3 or 6 Gy; viability was assessed 96 hrs after IR. As shown in FIG. 6B, neutralizing antibodies against IFNβ partially restored viability of D54 cells with LGP2 knockdown to the level of control cells (siNT). These data are consistent with earlier studies from our laboratory demonstrating that neutralizing antibodies to IFNs partially protected human tumor xenografts from IR-mediated cytotoxicity (Khodarev N N, et al. (2007) Signal transducer and activator of transcription 1 regulates both cytotoxic and prosurvival functions in tumor cells. *Cancer Res* 67(19): 9214-9220). These data also indicate that IR-induced tumor cell killing is mediated, in part, by the production of autocrine IFNβ (Khodarev N N, et al. (2007) Signal transducer and activator of transcription 1 regulates both cytotoxic and prosurvival functions in tumor cells. *Cancer Res* 67(19): 9214-9220; Khodarev N R, B, Weichselbaum, R (2012) Molecular Pathways: Interferon/Stat1 pathway: role in the tumor resistance to genotoxic stress and aggressive growth

*Clinical Cancer Research* 18(11):1-7). We conclude that LGP2 suppresses IR induced cytotoxic IFNβ production in tumor cells.

LGP2 Expression Predicts Poor Clinical Outcome in High Grade Gliomas.

Figure 7A:
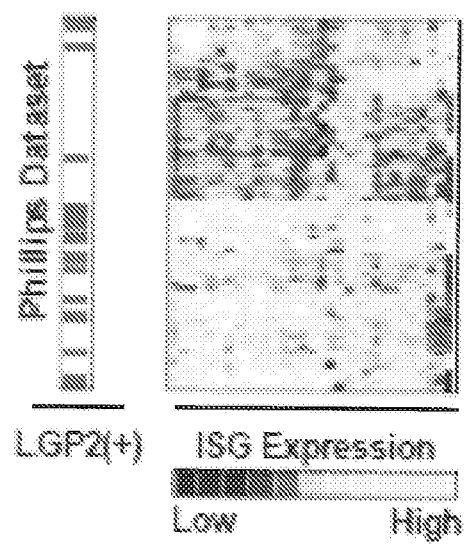
FIGS. 7A, 7B, 7C, and 7D show that expression of LGP2 is associated with poor overall survival in patients with GBM.
Figure 7B:
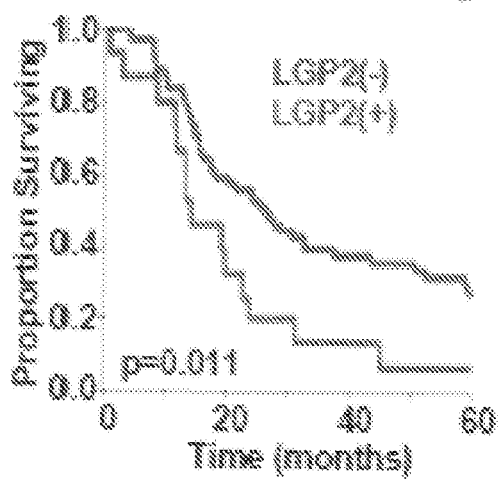
Figure 7C:
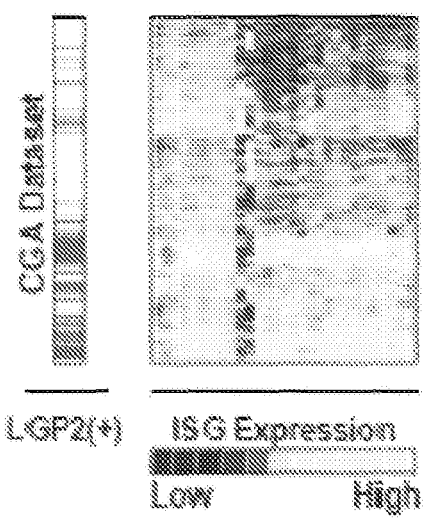
Figure 7D:
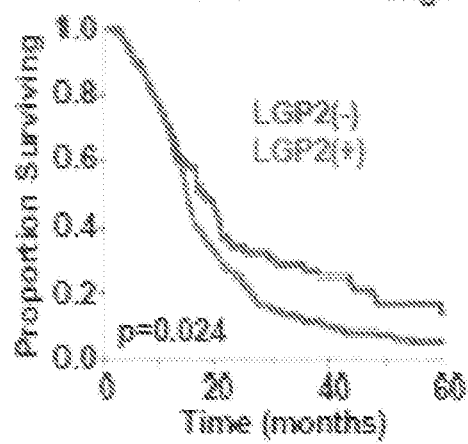

The studies described above suggest that depletion of LGP2 increases radiosensitivity whereas overexpression of LGP2 increases radioresistance of tumor cells. A key question is whether the results presented here are consistent with clinical experience and in particular the clinical outcomes in patients undergoing radiotherapy. Multiple studies have demonstrated an overall survival benefit for post-operative radiation therapy after surgical resection compared to surgery alone in the management of newly diagnosed glioblastoma multiforme (GBM) (Walker M D, et al. (1978) Evaluation of BCNU and/or radiotherapy in the treatment of anaplastic gliomas. A cooperative clinical trial. *Journal of neurosurgery* 49(3):333-343; Kristiansen K, et al. (1981) Combined modality therapy of operated astrocytomas grade III and IV. Confirmation of the value of postoperative irradiation and lack of potentiation of bleomycin on survival time: a prospective multicenter trial of the Scandinavian Glioblastoma Study Group. *Cancer* 47(4):649-652; Laperriere N, Zuraw L, Cairncross G, & Cancer Care Ontario Practice Guidelines Initiative Neuro-Oncology Disease Site G (2002) Radiotherapy for newly diagnosed malignant glioma in adults: a systematic review. *Radiotherapy and oncology: journal of the European Society for Therapeutic Radiology and Oncology* 64(3):259-273). In addition, the response of GBM tumors to radiation predicts the patient lifespan after treatment. In this regard, we described elsewhere that ISG expression correlated with poor overall survival in patients with GBM (Duarte C W, et al. (Expression signature of IFN/STAT1 signaling genes predicts poor survival outcome in glioblastoma multiforme in a subtype-specific manner. *PLoS One* 7(1):e29653). To investigate whether LGP2 gene expression is also related to clinical outcomes in patients with GBM, we analysed two independent GBM datasets from the Cancer Genome Atlas (CGA, see http://cancergenome.nih.gov/) (n=382) and the Phillips et al. study (n=77) (Phillips H S, et al. (2006) Molecular subclasses of high-grade glioma predict prognosis, delineate a pattern of disease progression, and resemble stages in neurogenesis. *Cancer cell* 9(3):157-173). In FIGS. 7A and 7C the relative expression of ISGs separates each dataset into ISG-positive and ISG-negative groups. FIGS. 7A and 7C further demonstrate that expression of LGP2 is highly associated with expression of ISGs. To examine the association of LGP2 expression with patient survival, we compared overall survival in the patient cohorts with relatively high and relatively low expression of LGP2. As is shown in FIGS. 7B and 7D, high expression of LGP2 was significantly associated with a 2.3-fold increased risk for death in the Phillips dataset (p=0.011, Cox proportional hazards test) and a 1.4-fold increased risk for death in the TCGA dataset (p=0.024). These data demonstrate that LGP2 gene expression is associated with poor clinical outcome in patients with GBM and support our hypothesis that this protein may serve as a potential biomarker and target for the radiosensitization of high grade gliomas.

Conclusions

The salient features of the results are as follows:

(i) We demonstrated a correlation between expression of LPG2 and resistance to IR in most of the 14 human cancers cell lines of diverse origins. In follow up studies we demonstrated that depletion of LGP2 enhanced cytotoxic sequelae of IR whereas overexpression of LGP2 increased the fraction of cells resistant to cytotoxicity induced by IR.

(ii) LGP2 is a constitutive cytoplasmic protein whose accumulation is enhanced by IFN and hence it is defined as an ISG. Several studies have identified a link between ISGs and aggressive tumor phenotypes with poor outcomes or radio/chemoresistance (Cheon H, Yang J, & Stark G R (2011) The functions of signal transducers and activators of transcriptions 1 and 3 as cytokine-inducible proteins. *J Interferon Cytokine Res* 31(1):33-40; Khodarev N R, B, Weichselbaum, R (2012) Molecular Pathways: Interferon/Stat1 pathway: role in the tumor resistance to genotoxic stress and aggressive growth *Clinical Cancer Research* 18(11):1-7). In studies designed to explore in more detail the interaction between LGP2, IFN and IR we showed that IR induces both IFNβ and enhances the accumulation of LPG2, that overexpression of LGP2 causes a significant reduction of IFNβ gene expression and lastly, that inhibition of IFNβ by neutralizing antibody results in increased resistance to cytotoxic effects induced by IR.

(iii) A survey of available databases suggests a correlation between the expression of LGP2 and poor outcomes in patients with malignant glioblastoma.

The significance of the studies presented here are as follows:

(i) Expression of LGP2 emerged as necessary and on the basis of the effects of ectopic expression as sufficient for enabling enhanced survival of cancer cells exposed to cytotoxic doses of IR. Since chemotherapeutic drugs may mimic the effects of IR, LGP2 may indeed be the primary but perhaps not unique ISG to block cytotoxic manifestations associated with IFN production in cells subjected to DNA damaging agents. Therefore it is contemplated that identification of the mechanism by which LGP2 acts to block IFN production may be a key to development of adjunct therapies to block its function and enhance therapeutic outcomes.

Figures 8A, 8B:
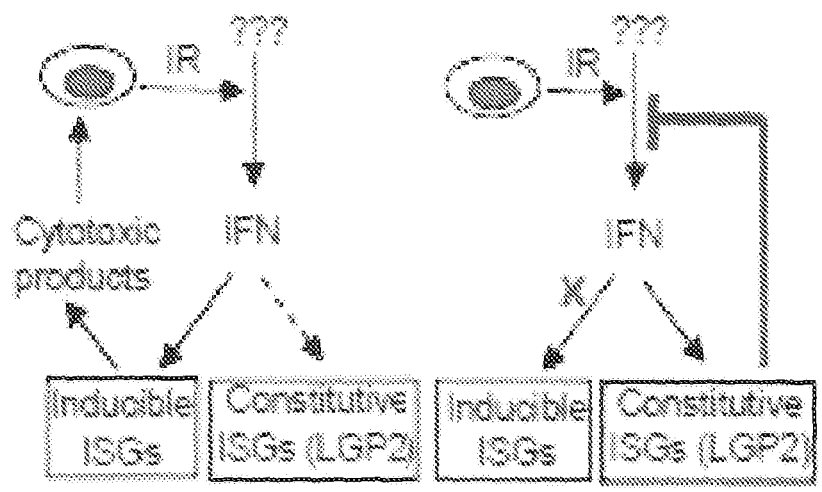
FIGS. 8A and 8B show activation of IFNβ by IR is suppressed by LGP2. Acute response to IR leads to activation of IFNβ and induction of ISGs with cytotoxic functions (Panel A). Chronic exposure to cytotoxic stress leads to constitutive expression of some ISGs with pro-survival functions and LGP2-dependent suppression of the autocrine IFNβ loop.
Figure 9:
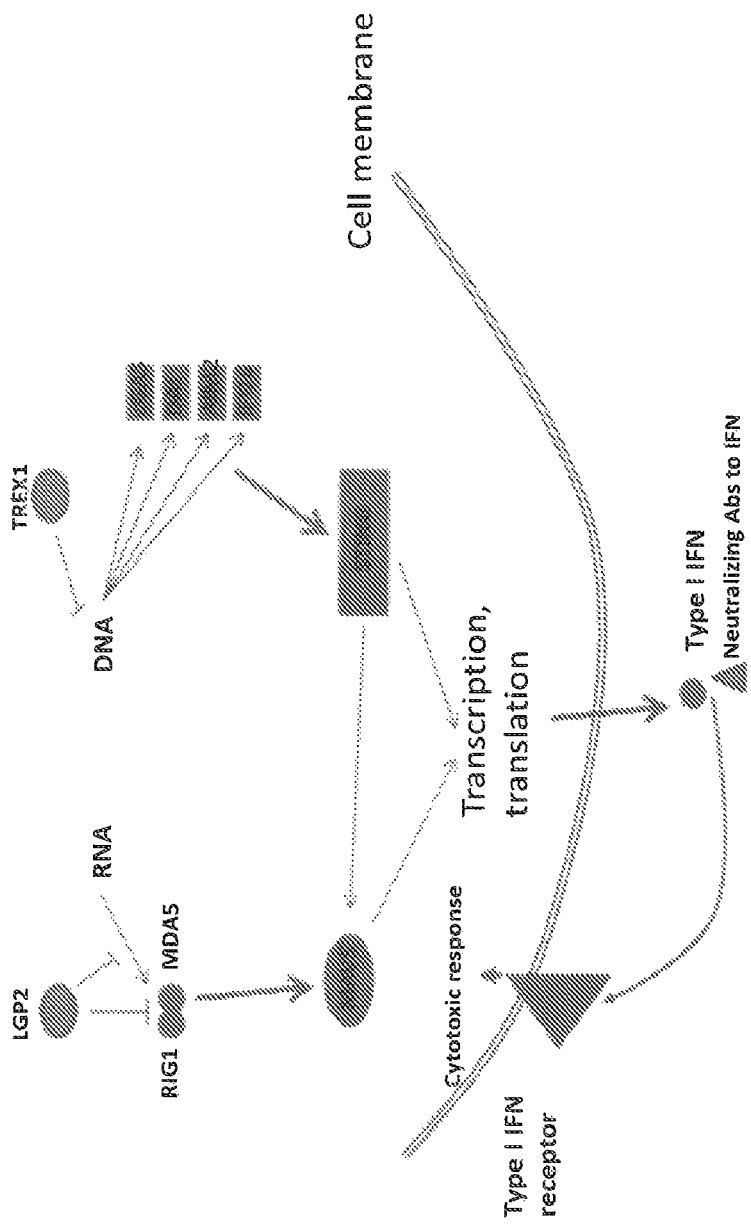
FIG. 9 shows schematics of cytoplasmic sensors for RNA and DNA. Two primary RNA sensors are RIG1 (DDX58) and MDA5 (IFIH1), while family of DNA sensors is redundant and includes, for example, cGAS (MB21D1), DAI (ZBP1, DLM1) AIM2, IFI16 and several other proteins. LGP2 (DHX58) represents apical suppressor of RNA-dependent pathway while exonuclease TREX1 (DNase III)-apical suppressor of DNA pathway. RNA pathway converges on adaptor protein MAVS (aka IPS1; VISA; CARDIFF) and DNA pathway converges on the adaptor protein STING (aka TMEM173; MPYS; MITA; ERIS). Both adaptor proteins activate NFkB-dependent, IRF3/IRF7-dependent transcription of Type I IFNs, which can further act through autocrine and paracrine loops as cytotoxins and/or signaling molecules. We found that for these pathways suppression of proteins with pro-IFN function (primary sensors, adaptor proteins) render cells radioresistant. On contrary, suppression of proteins with anti-IFN function (LGP2, TREX1) renders cells radiosensitive. These data are shown below in FIGS. 10-15.
Figure 10:
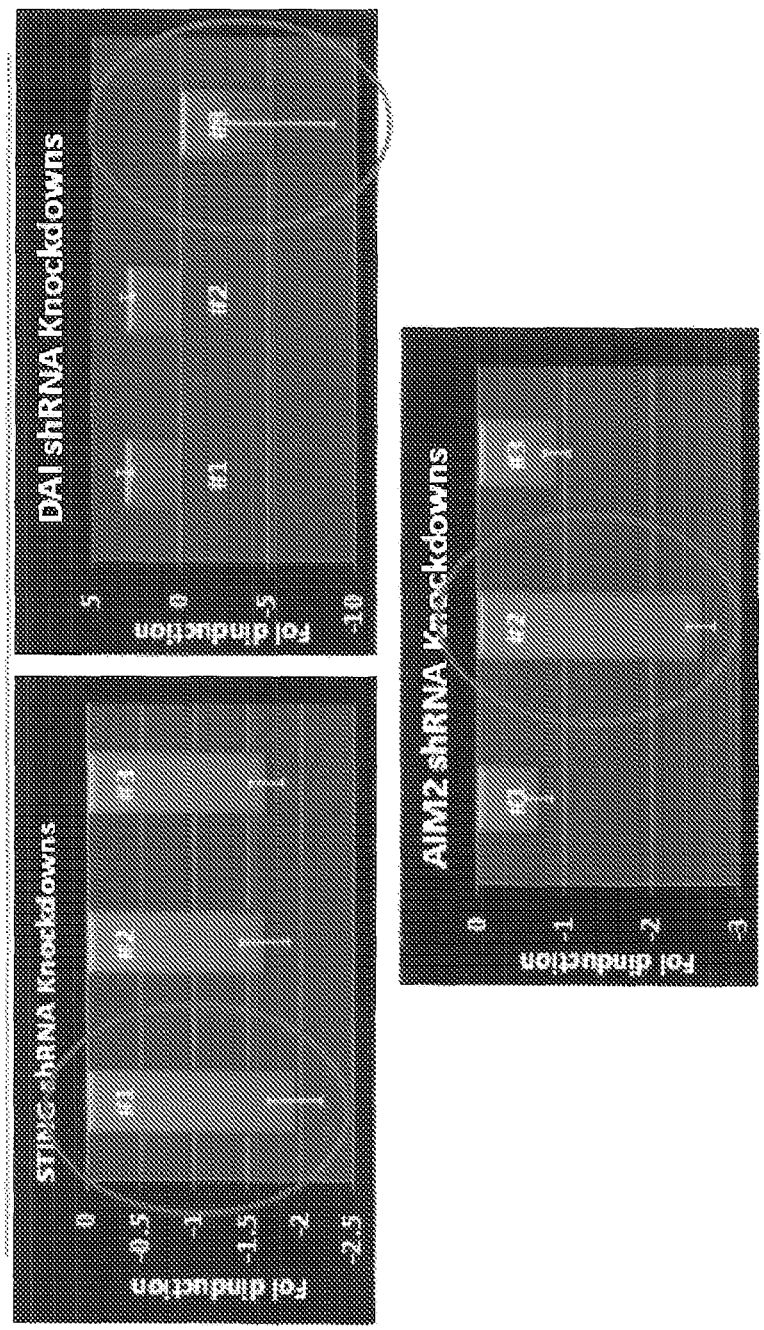
FIG. 10 shows RT-PCR confirmation of stable shRNA-derived knock-downs (KDs) of STING, DAI and AIM2 genes in SCC61 cell line. In other experiments we used siRNAs or embryonic fibroblasts from transgenic (knock-out) mice.
Figure 11:
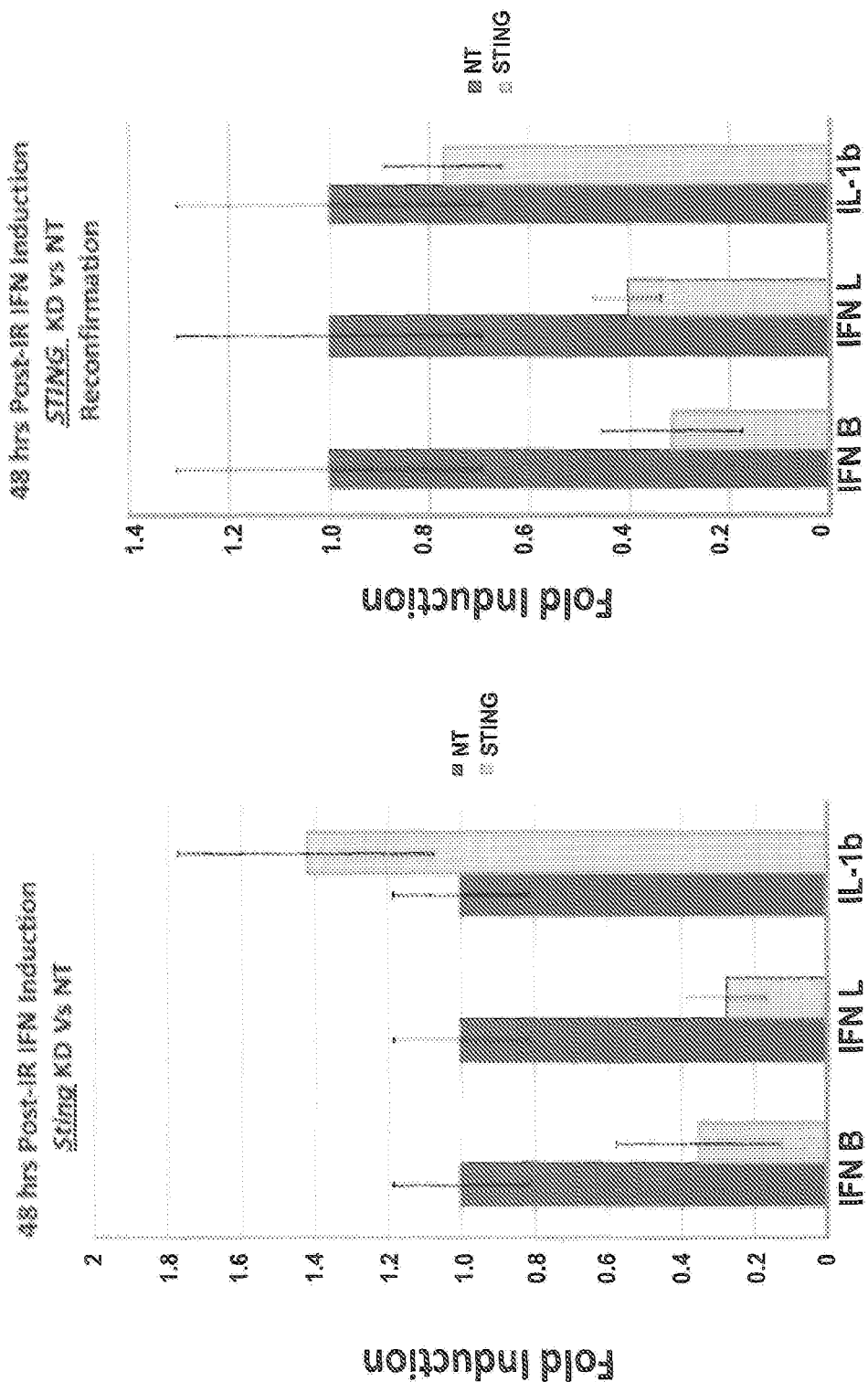
FIG. 11 shows that suppression of STING in SCC61 cell line leads to the suppression of IR-induced IFN-beta and IFN-lambda, but not IL-1b.
Figure 12:
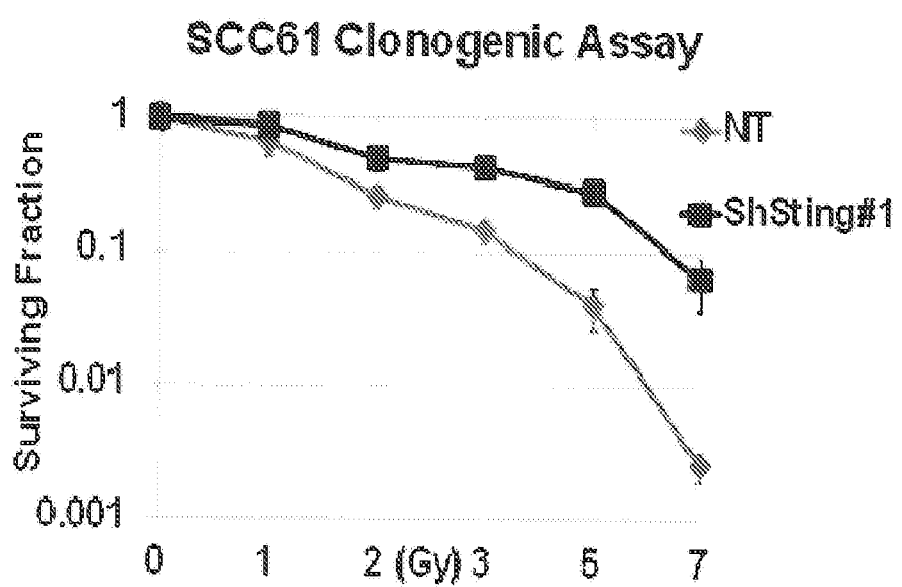
FIG. 12 shows that KD of STING in SCC61 leads to radioprotection of cells.
Figure 13:
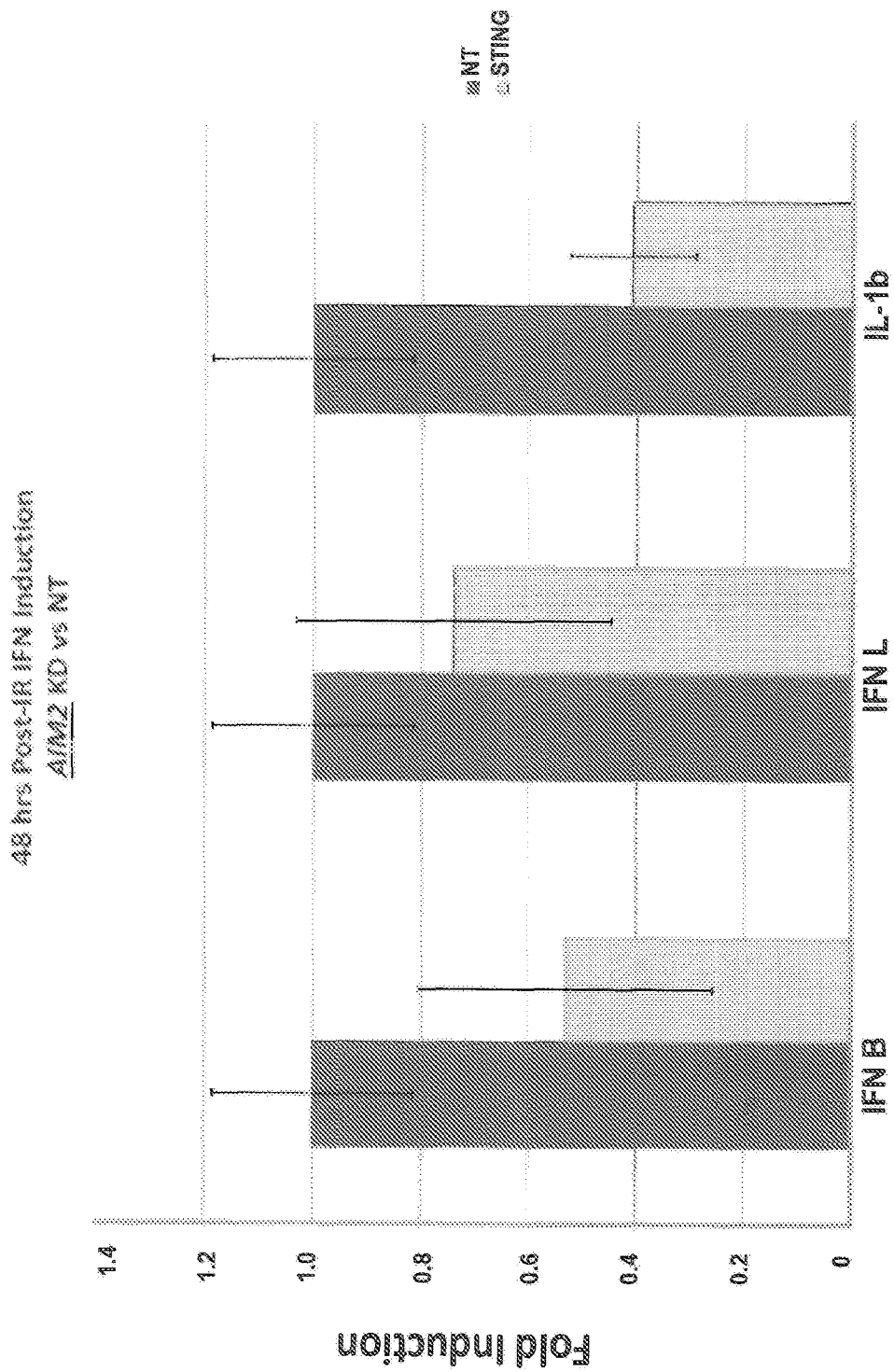
FIG. 13 shows that KD of AIM2 in our experimental system leads to the suppression of IR-induced IFN-beta and IFN-lambda, which allows predict radioprotective effects of suppression of this protein.
Figure 14:
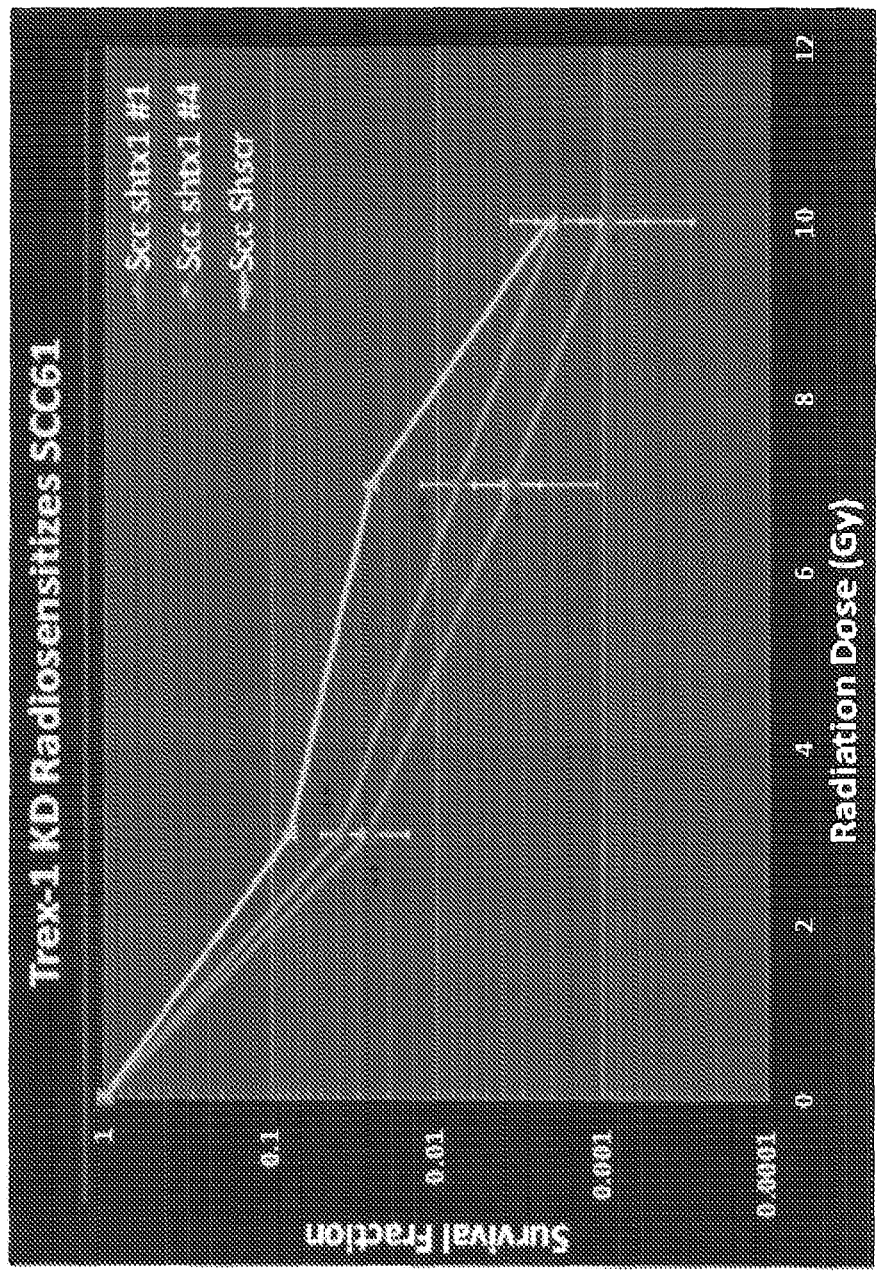
FIG. 14 shows that suppression of TREX1 in SCC61 leads to radiosensitization of cells (see FIG. 1)
Figure 15D:
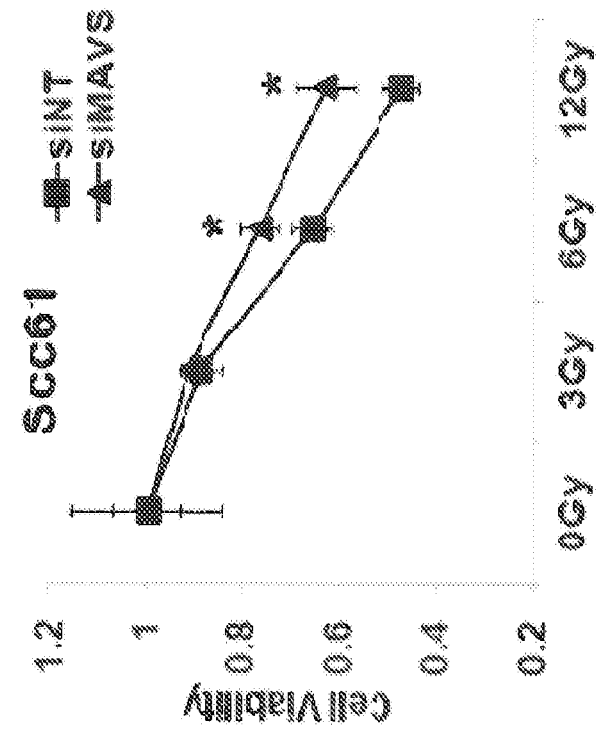
Figure 15C:
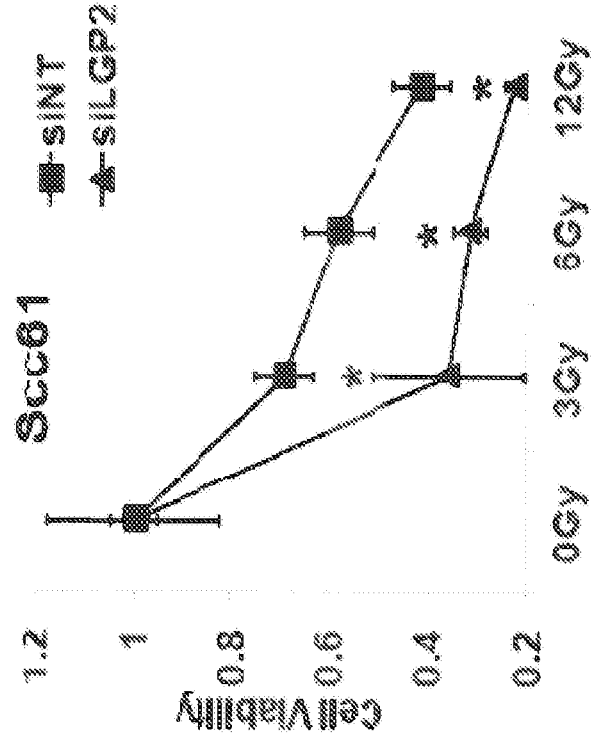
Figure 15F:
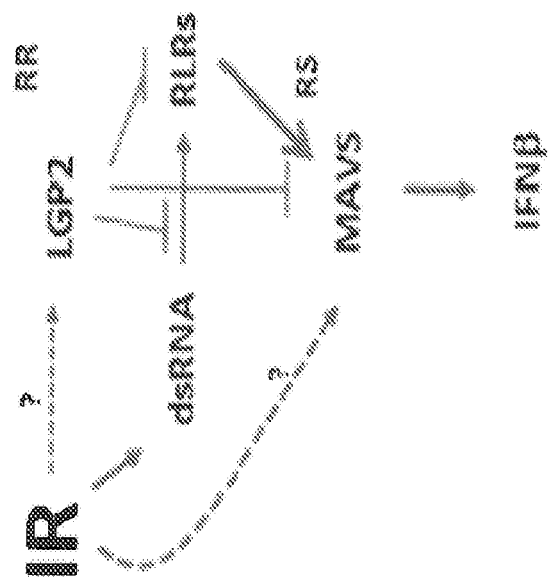
FIG. 15F shows schematics of interaction between LGP2 and MAVS in generation of IR-induced IFN-mediated cytotoxic response.
Figure 15E:
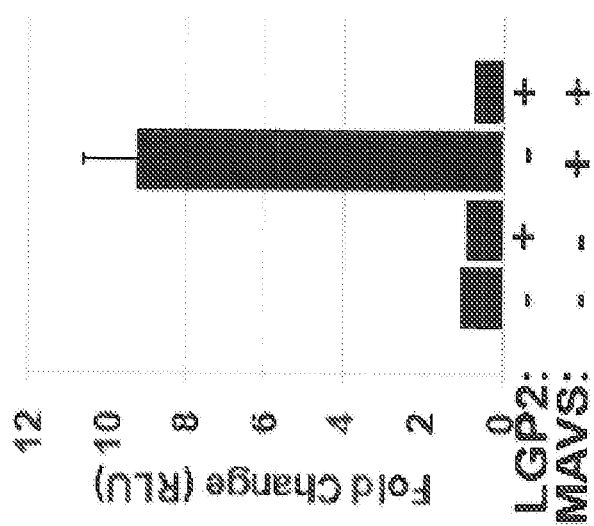
FIG. 15E shows that MAVS up-regulates transcription of IFN-beta, while LGP2 suppresses this MAVS-dependent effect

(ii) In light of the overwhelming evidence that LGP2 is a constitutive cellular protein whose accumulation is enhanced by IFN the obvious question is under what conditions is LGP2 inoperative and what activates its anti-IFN functions. In principle, LGP2 acts as a classic feedback inhibitor (FIG. 8) that is activated by an unknown mechanism. The solution to this puzzle is likely to greatly accelerate the mean by which its function could be blocked.

Example 2

STING Signaling Mediates Antitumor Effects of Radiation

Methods

Mice

Six- to eight-week old C57BL/6J mice were purchased from Harlan. MyD88$^{-/-}$, TRIF$^{-/-}$, CRAMP$^{-/-}$, 2 C CD8$^+$ T cell receptor (TCR)-Tg, CD11c-Cre-Tg mice were purchased from The Jackson Laboratory. IFNAR1$^{flox/flox}$ mice were kindly provided by Dr. Ulrich Kalinke of the Institute for Experimental Infection Research, Hanover, Germany. STING$^{-/-}$ mice were kindly provided by Dr. Glen N. Barber of University of Miami School of Medicine, Miami. IRF3$^{-/-}$ mice were kindly provided by T. Taniguchi of University of Tokyo, Tokyo, Japan. All the mice were maintained under specific pathogen free conditions and used in accordance to the animal experimental guidelines set by the Institute of Animal Care and Use Committee. This study has been approved by the Institutional Animal Care and Use Committee of the University of Chicago.

Tumor Growth and Treatments

1×10$^6$ MC38 tumor cells were subcutaneously injected into the flank of mice. Tumor volumes were measured along three orthogonal axes (a, b, and c) and calculated as tumor volume=abc/2. Tumors were allowed to grow for 9-10 days and treated by local radiation (Deng et al., 2014). Briefly, the body was protected with a lead cover and the tumor was exposed, allowing local radiation. Tumors were irradiated using RS-2000 Biological Irradiator (RAD SOURCE) at the dose of 20 Gy with 160 kV and 25 mA. For type I IFN blockade experiments, 200 µg anti-IFAR1 mAb was intratumorally injected on day 0 and 2 after radiation. For HMGB-1 blockade experiments, 200 µg anti-HMGB-1 mAb (clone 3B1, generated by inventors) was administered i.p. on day 0 and 3 after radiation. For CD8$^+$ T cell depletion experiments, 300 g anti-CD8 mAb (Clone 2.43, BioXCell) was delivered 5 times by i.p. injection every three days starting one day before radiation. For exogenous IFN-β treatment experiments, 1×10$^{10}$ viral particles of Ad-IFN-β (Burnette, B., et al., The Efficacy of Radiotherapy Relies upon Induction of Type I Interferon-Dependent Innate and Adaptive Immunity, Cancer Res Apr. 1, 2011 71; 2488; (doi: 10.1158/0008-5472.CAN-10-2820)) were intratumorally administered on day 2 after radiation. Ad-null was used as negative control. For cGAMP treatment experiments, 10 µg 2'3'-Cgamp (InvivoGen; cyclic [G(2',5')pA(3',5')p]); CAS 1441190-66-4) in PBS was intratumorally administered on day 2 and 6 after radiation at a dose of 0.45 µg/mg.

In Vitro Culture and Function Assay of BMDCs

Single-cell suspensions of bone marrow cells were obtained from C57BL/6J, STING$^{-/-}$ and IRF3$^{-/-}$ mice. Bone marrow from cGAS$^{-/-}$ mice was kindly provided by Dr. Zhijian J. Chen of University of Texas Southwestern Medical Center, Dallas. The cells were placed in 10 cm petri dish and cultured in RPMI-1640 medium containing 10% fetal bovine serum (DENVILLE), supplemented with 20 ng/ml GM-CSF. Fresh media with GM-CSF was added into culture on day 3. BMDCs (bone marrow-derived dendritic cells) were harvest for stimulation assay on day 7. 8×10$^6$ MC38-SIY$^{hi}$ cells were plated into 10 cm cell culture dishes overnight, and then pretreated with 40 Gy and incubated for 5 hours. BMDCs were added and co-cultured with MC38-SIY$^{hi}$ cells at the ratio of 1:1 in the presence of fresh GM-CSF for additional 8 hours. Subsequently purified CD11c cells with EasySep™ Mouse CD11c Positive Selection Kit II (STEMCELL) were incubated with isolated CD8$^+$ T cells from naive 2 C mice for three days. For the bypassing assay, 10 ng/ml murine IFN-β was added in the co-culture of BMDCs and tumor cells, or 100 µg/ml DMXAA was added into isolated CD11c$^+$ cells with additional 3 h incubation. For IFN-β detection, BMDCs were co-cultured with tumor cells at the ratio of 1:1 for additional 8 hours, and 1×10$^6$ cells/ml purified CD11c$^+$ cells were seed into 96-well plates for 48 hours.

RNA Interference siRNAs (Mission siRNA) against murine cGAS and control siRNA were purchased from Sigma as described. BMDCs were transfected with siRNA by Lipofectamine RNAiMAX Reagent (Invitrogen) at a final concentration of 50 nM: mmcGAS 5'-GAGGAAAUCCGCUGAGU-CAdTdT-3' (SEQ ID NO:8); MissionsiRNA Universal Negative control 1. Forty-eight hours after transfection, cells were used for further experiments.

RNA Extraction and Quantitative Real-Time RT-PCR

Total RNA from sorted cells was extracted with the RNeasy Micro Kit (QIAGEN) and reversed-transcribed with Seniscript Reverse Transcription Kit (QIAGEN). Real-time RT-PCR was performed with SSoFast EvaGreen supermix (Bio-Rad) according to the manufacturer's instructions and different primer sets on StepOne Plus (Applied Biosystems). Data were normalized by the level of 18S expression in each individual sample. $2^{-\Delta\Delta Ct}$ method was used to calculate relative expression changes.

ELISA

Tumor tissues were excised on day 3 after radiation and homogenized in PBS with protease inhibitor. After homogenization, Triton X-100 was added to obtain lysates. Cell culture supernatants were obtained from isolated CD11c$^+$ cells after 48 h-incubation with fresh GM-CSF. The concentration of IFN-β and CXCL10 was measured with VeriKine-HS™ Mouse Interferon Beta Serum ELISA Kit (PBL Assay Science) and mouse CXCL10 Quantikine ELISA kit (R&D) in accordance with the manufacturer's instructions, respectively.

Measurement of IFNγ-Secreting CD8$^+$ T Cells by ELISPOT Assay

For bone-marrow CD11c$^+$ cells functional assay, 2×10$^4$ purified CD11c$^+$ cells with were incubated with isolated CD8$^+$ T cells from naive 2 C mice with EasySep™ Mouse CD8a Positive Selection Kit (STEMCELL) for three days at the ratio of 1:10. For tumor-specific CD8$^+$ T cells functional assay, eight days after radiation, tumor DLNs were removed and CD8$^+$ T cells were purified. MC38 tumor cells were exposed to 20 ng/ml murine IFN-γ for 24 hr prior to plating with purified CD8$^+$ T. 2×10$^5$ CD8$^+$ T cells were incubated with MC38 at the ratio of 10:1 for 48 hours. 96-well HTS-IP plate (Millipore) was pre-coated with 2.5 µg/ml anti-IFN-γ antibody (clone R4-6A2, BD Pharmingen) overnight at 4° C. After co-culture, cells were removed, 2 µg/ml biotinylated anti-IFN-γ antibody (clone XMG1.2, BD Pharmingen) was added, and the plate was incubated for 2 h at room temperature or overnight at 4° C. Avidin-horseradish peroxidase (BD Pharmingen) with a 1:1000 dilution was then added and the plate was incubated for 1 h at room temperature. The cytokine spots of IFN-γ were developed according to product protocol (Millipore).

Cell Lines and Reagents

MC38 is a murine colon adenocarcinoma cell line. MC38-SIY was selected for a single clone after being transduced by lentivirus expressing human EGFR (L858R)-SIY. Anti-mIF-NAR1 neutralizing mAb (clone MAR1-5A3) and anti-CD8 depleting mAb (clone 2.43) were purchased from BioXcell (West Lebanon, N.H.). Anti-HMGB-1 neutralizing mAb (clone 3B1) was produced in house. Anti-HMGB-1 mAb is capable of neutralizing HMGB-1 in vivo. Conjugated antibodies against CD11b, CD11c and CD45, and 7-AAD were purchased from BioLegend. 2'3'-cGAMP was purchased from InvivoGen. DMXAA was purchased from Selleck Chemicals. Murine IFN-β, murine IFN-γ and murine GM-CSF was purchased from PEPROTECH.

Direct Priming Assay

Bone-marrow CD11c cells were co-cultured with purified CD8$^+$ T cells from 2 C mice in the presence of 1 µg/ml SIY peptide (SIYRYYGL) for three days. The supernatants were harvested for IFN-γ detection.

Flow Cytometric Sorting and Analysis

To obtain single cell suspensions, tumor tissues were cut into small pieces and mechanical dissociated with the gentleMACS™ Dissociators (Miltenyi Biotech). Then tumor tissues were digested by 1 mg/ml collagenase IV (Sigma) and 0.2 mg/ml DNase I (Sigma) for 30 min at 37° C. For the staining, single cell suspensions were blocked with anti-FcR (clone 2.4G2, BioXcell) and then stained with antibodies against CD11c, CD11b and CD45, and 7-AAD. Cells were performed on FACSAria II Cell Sorter (BD). For Mouse IFN-γ Flex Set CBA assay, IFN-γ detection in the supernatants was performed on FACSCalibur Flow Cytometer (BD). Data were analyzed with FlowJo Software (ThreeStar).

Primer Sequences for Real-Time PCR

Primer sequences for quantitative real-time PCR were as follows:

```
mIFN-β forward
                                        (SEQ ID NO: 9)
5'-GGTGGAATGAGACTATTGTTG-3', mIFN-β reverse
                                       (SEQ ID NO: 10)
5'-AAGTGGAGAGCAGTTGAG-3';

m-cGAS forward
                                       (SEQ ID NO: 11)
5'-ACCGGACAAGCTAAAGAAGGTGCT-3', m-cGAS reverse
                                       (SEQ ID NO: 12)
5'-GCAGCAGGCGTTCCACAACTTTAT-3';
and 18S forward
                                       (SEQ ID NO: 13)
5'-CGTCTGCCCTATCAACTTTCG-3', 18S reverse
                                       (SEQ ID NO: 14)
5'-TGCCTTCCTTGGATGTGGTA-3'.
```

Statistical Analysis

Experiments were repeated three times. Data were analyzed using Prism 5.0 Software (GraphPad) and presented as mean values±SEM. The P values were assessed using two-tailed unpaired Student t tests and $p<0.05$ was considered significant. For tumor-bearing mice frequency, statistics were done with the log rank (Mantel-Cox) test.

Discussion

We previously demonstrated that antitumor effects of radiation were dependent on type I IFN signaling by utilizing IFNAR1$^{-/-}$ mice (Burnette et al., 2011). To rule out the possibility that failure of tumors to respond to radiation was due to the intrinsic or developmental deficiency of IFNAR$^{-/-}$ mice, we administered blocking antibody against IFNAR1 in wild type (WT) mice following radiation. The results were similar to the effects observed in the knockout (KO) mice in that the antitumor effect of radiation was greatly attenuated by the neutralization of type I IFNs signaling with antibodies (FIG. 16A). The prevailing understanding of type I induction by the detection of DAMPs is dominated by the activation of TLRs (Chen and Nunez, 2010; Kono and Rock, 2008). The adaptor proteins MyD88 and TRIF mediate the induction of type I IFNs by TLRs activation with DAMPs recognition (Desmet and Ishii, 2012). In addition, it has been demonstrated that MyD88 is essential for antitumor immunity of chemotherapy and targeted therapies with anti-HER2 (Apetoh et al., 2007; Park et al., 2010; Stagg et al., 2011). To test the role of MyD88 upon radiation, we implanted tumor cells on flanks of WT and MyD88$^{-/-}$ mice. The inhibition of tumor growth post radiation was comparable between WT and MyD88$^{-/-}$ mice (FIG. 16B). This surprising result demonstrates that MyD88 in the host is dispensable for antitumor effect of radiation. To examine whether TRIF is important for the antitumor effect of radiation, we injected tumor cells into WT and TRIF$^{-/-}$ mice. The deficiency of TRIF in the host failed to reverse tumor inhibition by radiation (FIG. 16C). This result is consistent with our previous observation, confirming that TRIF is redundant for antitumor effect of radiation (Burnette et al., 2011). HMGB-1 secretion has been shown to be essential for antitumor immunity of chemotherapy and targeted therapies with anti-HER2 (Apetoh et al., 2007; Park et al., 2010). Similar to chemotherapy and targeted therapies, radiotherapy induces cell stress and result in the secretion of DAMPs. To examine whether HMGB-1 secretion is critical for the antitumor effect of radiation, we blocked HMGB-1 with antibodies following radiation. Tumor control of radiation was unaffected by anti-HMGB-1 treatment (FIG. 16D), suggesting that HMGB-1 secretion is also not required for the antitumor effect of radiation. The cathelicidin-related antimicrobial peptide (CRAMP in mice and LL37 in human) has been identified as a mediator of type I IFN induction by binding self-DNA to trigger TLR9-MyD88 pathway (Diana et al., 2013; Lande et al., 2007). To validate the possibility that CRAMP is responsible for the radiation response, we inoculated tumor cells into WT and CRAMP$^{-/-}$ mice. The deficiency of CRAMP was unable to dampen the antitumor effect of radiation (FIG. 16E), indicating that CRAMP is unnecessary for radiation response. Taken together, these data indicate that well-characterized TLRs-dependent molecular mechanisms involved in chemotherapy and targeted therapies using antibodies are not responsible for antitumor efficacy of radiation. Also, these results raise the possibility that a unique molecular mechanism which is TLRs-independent for type I IFN induction mediates the antitumor effect of radiation.

Recently, STING-mediated cytosolic DNA sensing cascade has been demonstrated to be one major mechanism of TLR-independent type I IFN induction. This process requires TBK1 and its downstream transcription factor, IRF3 (Desmet and Ishii, 2012; Wu and Chen, 2014). To determine the role of STING in radiation response, we implanted tumor cells on flanks of WT and STING$^{-/-}$ mice to monitor tumor growth curve. Without radiation treatment, the tumor growth was identical in WT mice and in STING$^{-/-}$ mice. In contrast, the tumor burden was significantly reduced by radiation in WT mice, whereas the deficiency of STING in the host significantly impaired the antitumor effect of radiation (FIG. 16F), demonstrating that STING signaling is important for the antitumor effect of radiation. Taken together, these results suggest that newly-defined STING-dependent cytosolic DNA sensing pathway, not well-characterized TLRs-dependent nucleic acids sensing pathways, mediates the antitumor effect of radiation.

Results

Figures 17A, 17B, 17C:
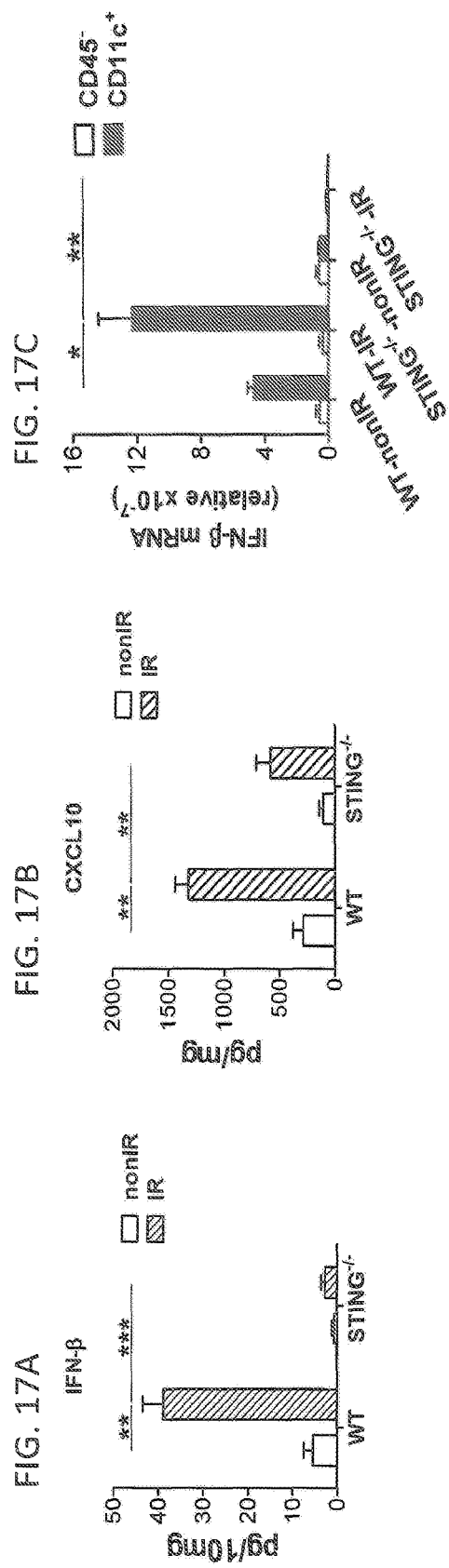
FIGS. 17A, 17B, and 17C show STING signaling in IFN-β induction by radiation.

STING Signaling Controls Type I IFN Induction and Innate Immune Responses Upon Radiation To test whether STING was responsible for type I induction following radiation, we measured the protein level of IFN-β in tumors. The induction of IFN-β in tumors was significantly abrogated in the absence of STING in the host after radiation (FIG. 17A). To validate whether STING mediates type I IFN induction, we determined the protein level of CCL10, a type I IFN-stimulated gene (Ablasser et al., 2013; Holm et al., 2012). The induction of CXCL10 in tumors was markedly diminished after radiation in the STING-deficient host (FIG. 17B), confirming that radiation-mediated type I IFN induction is determined by the presence of STING. These results indicate that STING in the host, not in tumor cells, mediates type I induction by radiation. Next, to determine in which cell population STING mediates type I IFN induction, we performed quantitative real-time PCR assay of IFN-β in different sorted cell populations from tumors after radiation. We observed that DCs (CD11c$^+$)

were the major producer of IFN-β after radiation, compared to CD45⁻ population and the rest of myeloid cells (data not shown), whereas radiation-mediated the induction of IFN-β mRNA by DCs was abolished in the host with STING deficiency (FIG. 17C). Together, these data suggest that host STING controls radiation-mediated type I IFN induction in tumors and that the presence of STING in tumor-infiltrating DCs plays a major role in type I IFN induction after radiation.

Figure 18A:
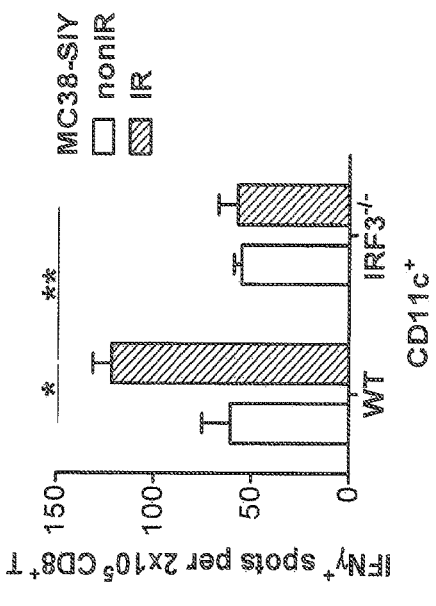
FIGS. 18A, 18B, 18C and 18D show STING-IRF3 axis in dendritic cells is activated by irradiated-tumor cells.
Figure 18C:
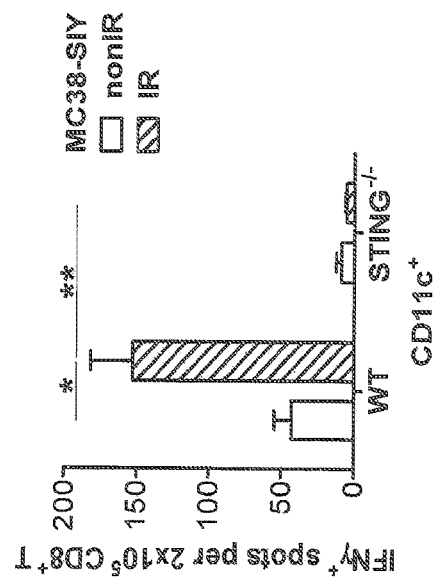
Figure 18B:
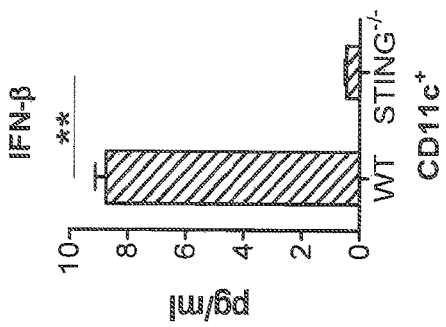

To determine whether STING signaling is activated by irradiated-tumor cells and whether it is essential to cross-priming of DCs for CD8⁺ T cells, a cross-priming assay was conducted with BMDCs from WT and STING⁻/⁻ mice. The function of DCs was significantly elevated by the stimulation of irradiated-tumor cells compared to non-irradiated-tumor cells, whereas the deficiency of STING in DC resulted in failed responses of DCs to cross-prime T cells (FIG. 18A). It has been demonstrated that STING-dependent type I IFN production is mediated by IRF3 phosphorylation (Wu and Chen, 2014). To confirm that STING-associated downstream for radiation-mediated type I IFN production is essential to the function of DCs, we performed cross-priming assay with WT-BMDCs and IRF3⁻/⁻BMDCs. Similar to STING⁻/⁻ BMDC, IRF3⁻/⁻BMDCs failed to cross-prime CD8⁺ T cells with the stimulation of irradiated-tumor cells (FIG. 18B). These results indicate that STING-IRF3 axis in DCs is activated by irradiated-tumor cells, in turn, the activation of the STING-IRF3 axis predominates the cross-priming ability of DCs.

Figure 18D:
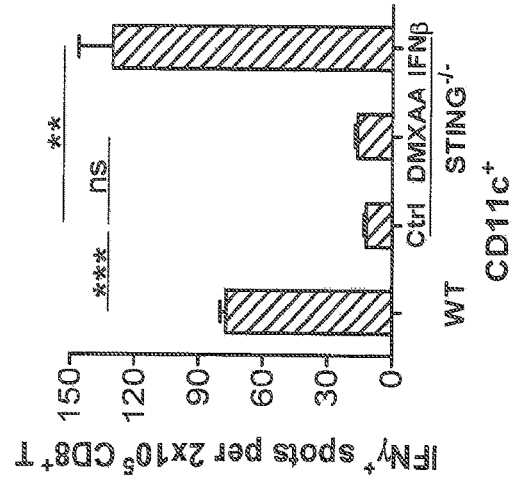
Figure 23:
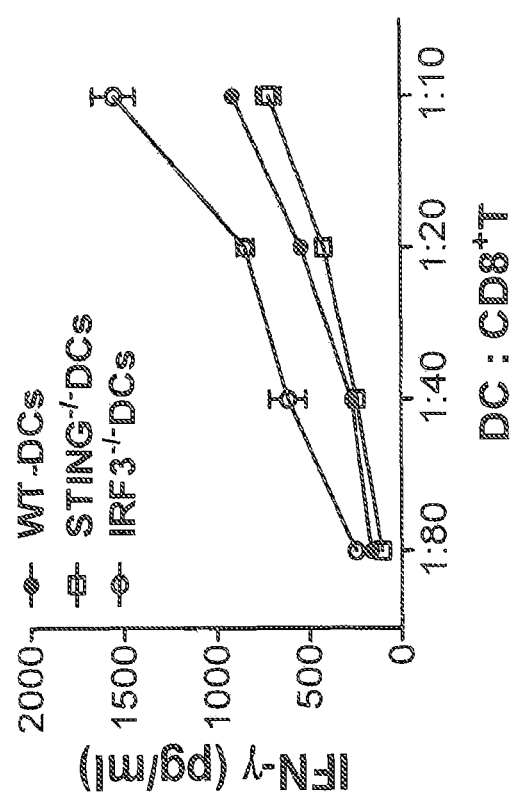
FIG. 23 shows the ability of WT, STING$^{-/-}$ and IRF3$^{-/-}$ BMDCs in the direct-priming of CD8$^+$ T cells. BMDCs were stimulated with 20 ng/ml GM-CSF for 7 days. BMDCs were co-cultured with isolated CD8$^+$ T cells from naive 2 C mice at different ratios in the presence of 1 μg/ml SIY peptide for three days. The supernatants were harvested and subjected to CBA assay. Representative data are shown from three experiments. Data are represented as mean±SEM.

To determine whether exogenous IFN-β treatment rescues the functions of STING⁻/⁻BMDCs, we added IFN-β into the co-culture system of BMDCs and tumor cells. The functions of STING⁻/⁻BMDCs were restored in the presence of exogenous IFN-β treatment (FIG. 18C). Recently, it has been demonstrated that DMXAA binds to murine STING and activates STING signaling to induce type I IFN production (Gao et al., 2013b). DMXAA fails to rescue the function of STING⁻/⁻BMDCs, confirming activation of STING is required to increase cross-priming through IFN pathway (FIG. 18C). Next, to rule out the possibility that the discrepancy in priming ability of STING⁻/⁻ DCs and IRF3⁻/⁻ DCs are due to intrinsic defects of these cells, a direct priming assay was performed with peptide stimulation. Remarkably, no significant difference was observed between WT-BMDCs and STING⁻/⁻ BMDCs function in priming 2 C cells with the stimulation of SIY peptide (FIG. 23). It suggests that DC has not intrinsic defect in cross priming. IRF3⁻/⁻ DCs were even more efficient than WT DCs in priming 2 C cells with SIY peptide stimulation (FIG. 23), probably due to pro-apoptotic function of IRF3. To validate STING signaling is activated by irradiated-tumor cells, we determined the production of IFN-3 by WT-BMDCs and STING⁻/⁻BMDCs stimulated by irradiated-tumor cells. The protein level of IFN-β was remarkably reduced in STING⁻/⁻ BMDCs compared to WT-BMDCs (FIG. 18D). These results indicate that activation of STING by irradiated-tumor cells controls type I IFN induction in DCs and this process is a pivotal contributor to the ability of DCs to cross-prime CD8⁺ T cells. On the other hand, these results raise the possibility that STING molecules in DCs are activated by a certain stimulator, presumably DNA, provided by irradiated-tumor cells.

cGAS Mediates Dendritic Cell Sensing of Irradiated-Tumor Cells

Recent studies have shown that cGAS is a cytosolic DNA-sensing enzyme that catalyses the production of cyclic GMP-AMP (cGAMP), a second-messenger activator of STING-dependent type I IFN production (Wu and Chen, 2014). Furthermore, elevation of cGAS mRNA level in CD11c⁺ cells from tumors is observed after radiation (FIG. 19A), indicating that cGAS in DC is likely induced by its substrate, cytosol DNA, following radiation. To interrogate whether cGAS is required for DCs sensing of irradiated-tumor cells to stimulate adaptive immunity, we silenced cGAS in BMDCs using siRNA. The silencing of cGAS in BMDCs greatly diminished the function of DCs compared to the silencing of non-target controls, when stimulated with irradiated-tumor cells (FIG. 19B). To validate the role of cGAS in DCs sensing of irradiated-tumor cells, we compared the function of BMDCs from WT and cGAS⁻/⁻ mice. In contrast to WT BMDCs, cGAS⁻/⁻ BMDCs failed to cross-prime 2 C cells in response to stimulation by irradiated-tumor cells (FIG. 19C), confirming that cGAS is important for DCs sensing of irradiated-tumor cells. To map whether cGAS-STING-type I IFN axis determines the function of BMDCs, we performed bypass experiments with the treatment of exogenous IFN-β and DMXAA. The functions of cGAS⁻/⁻ BMDCs were restored with IFN-β and DMXAA treatment, respectively (FIG. 19D). To further confirm that cGAS is required for the BMDCs sensing of irradiated-tumor cells, we determined the production of IFN-β in WT-BMDCs and cGAS⁻/⁻BMDCs after stimulation of irradiated-tumor cells. The protein level of IFN-β was greatly decreased in cGAS⁻/⁻BMDCs compared to WT-BMDCs (FIG. 19E). Therefore, these results indicate that cGAS mediates type I IFN production to enhance the function of DCs in response to irradiated-tumor cells. Also, these results suggest that DNA from irradiated-tumor cells is delivered into the cytosol of DCs and then binds to cGAS to trigger STING-dependent type I IFN induction.

Figure 24A:
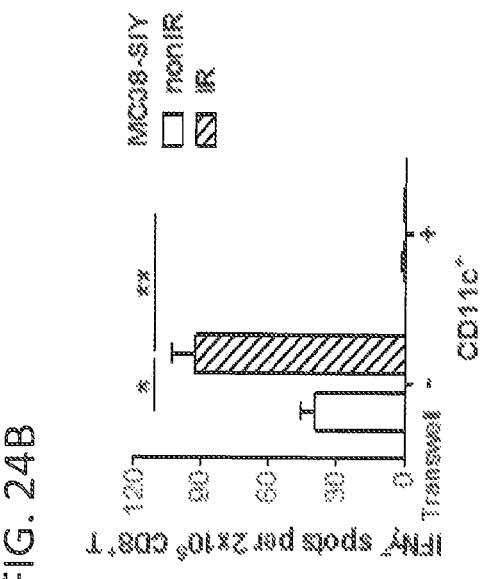
FIGS. 24A and 24B show that irradiated-tumor cells are sensed by dendritic cells in a direct cell-to-cell contact manner.
Figure 24B:
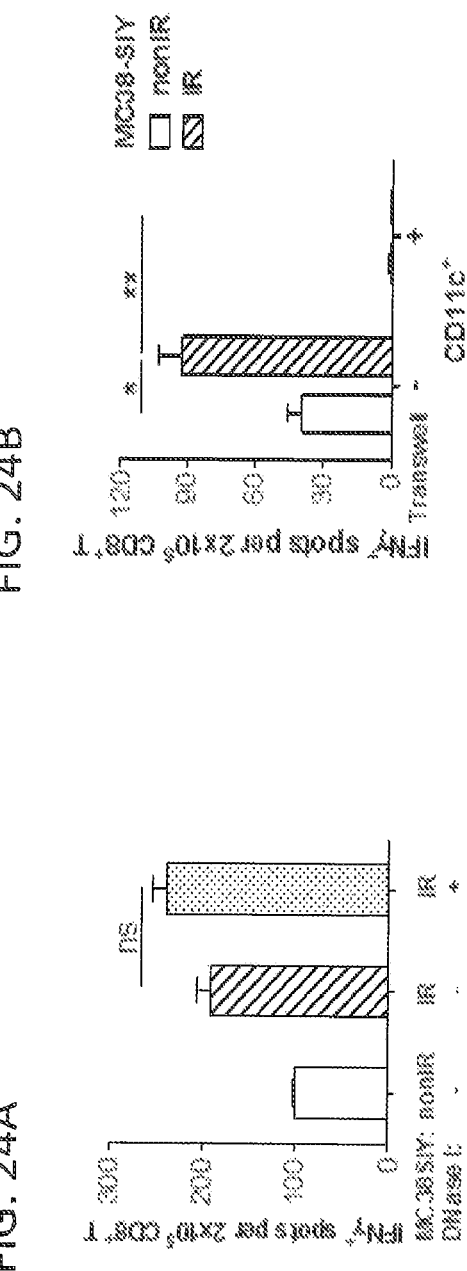

We next determine how DNA from irradiated-tumor cells is delivered into the cytosol of DCs. With the damaging effects of radiation, we hypothesize that cells might either lose membrane integrity and release endogenous DNA fragments which are engulfed by DCs, or maintain membrane integrity and DNA fragments are transferred by phagocytosis. In the presence of DNase I, the priming ability of DCs response was not impaired when stimulated by irradiated-tumor cells (FIG. 24A), suggesting that DCs unlikely engulf floating naked DNA fragments. To test whether DNA is delivered by exosome vesicles, BMDCs were stimulated with irradiated-tumor cells in a contact or a non-contact system. Separating BMDCs and irradiated-tumor cells via a trans-well screen which only allows media to travel freely, completely abolished the functions of DCs (FIG. 24B), indicating DNA delivery is mediated by direct cell-to-cell contact, not exosome vesicles. Taken together, these results suggest that DNA from irradiated-tumor cells is sensed by host cGAS during cell-cell contact engulfing process, such as phagocytosis.

STING Signaling Promotes Adaptive Immune Responses Upon Radiation

Our previous studies have shown that adaptive immune responses play an important role for the anti-tumor effect with either radiation alone or combined immunotherapy (Deng et al., 2014; Lee et al., 2009; Liang et al., 2013). To validate the role of CD8⁺ T cells after radiation in the current tumor model, MC38, depleting antibodies against CD8⁺ T cells were administrated following radiation. In agreement with our previous reports, the anti-tumor effect of radiation was greatly reduced with the depletion of CD8⁺ T cells after radiation (FIG. 20A), mimicking the tumor growth curve in STING⁻/⁻ mice post radiation. We sought to examine whether the failure of response to radiation in STING⁻/⁻ mice is due to impairment in the function of CD8+ T cells. To test whether STING signaling impacts a tumor antigen-specific CD8+ T cell response, we performed ELISPOT assay with purified CD8+ T cells from tumor draining lymph nodes (DLNs). Radiation induced a robust tumor antigen-specific CD8+ T cell responses in WT mice, whereas the antigen-specific CD8+ T cell responses in STING$^{-/-}$ mice after radiation were significantly diminished (FIG. 20B). To confirm that the impairment of CD8+ T cell responses in STING$^{-/-}$ mice post radiation is due to the insufficient induction of type I IFNs, STING$^{-/-}$ mice received intratumorally treatment with Ad-IFN-β following radiation. Exogenous IFN-β treatment was able to restore the CD8+ T cell functions in STING$^{-/-}$ mice after radiation (FIG. 20C). In addition, the intrinsic defect of CD8+ T cell responses has previously been examined through the vaccination of ovalbumin and incomplete Freunds adjuvant. The CD8+ T cell response in STING$^{-/-}$ mice and WT mice was demonstrated to be equivalent (Ishikawa et al., 2009). As a result, these data together show that the reduction of type I IFNs, not intrinsic defect of T cells, accounts for inadequate adaptive immune responses in STING$^{-/-}$ mice after radiation. Together, these results suggest that STING signaling is important for radiation-induced antitumor adaptive immune response.

Figure 21A:
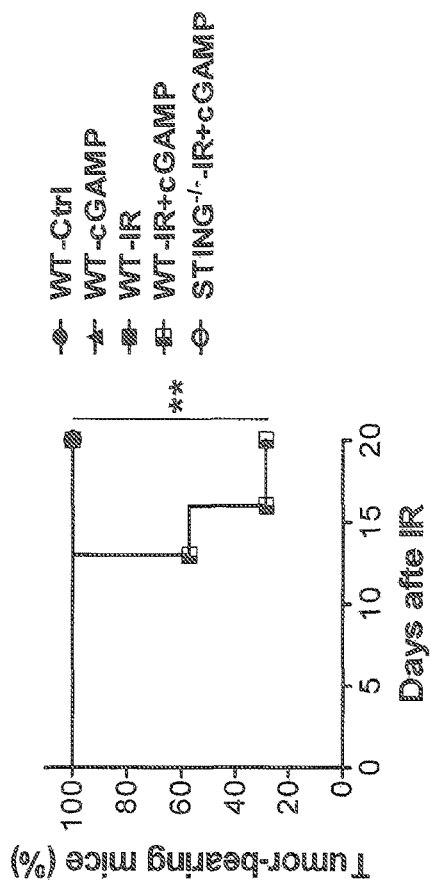
FIGS. 21A, 21B, 21C, and 21D show cGAMP treatment promotes the antitumor effect of radiation in a STING-dependent manner.
Figure 21B:
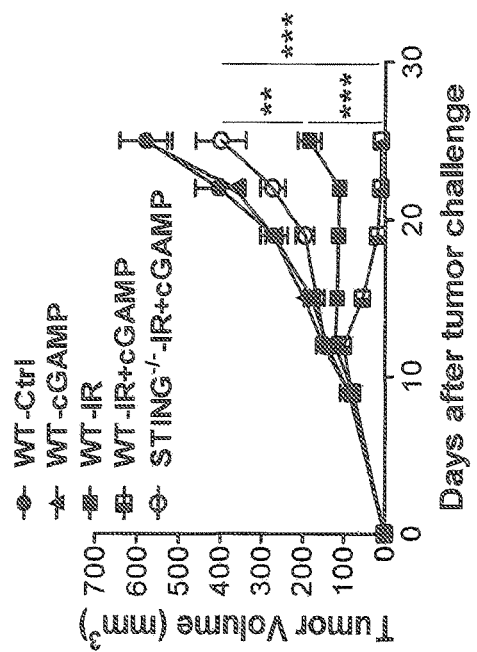
Figure 21C:
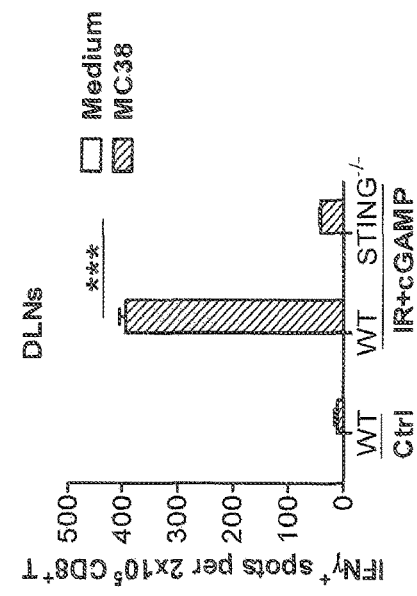
Figure 21D:
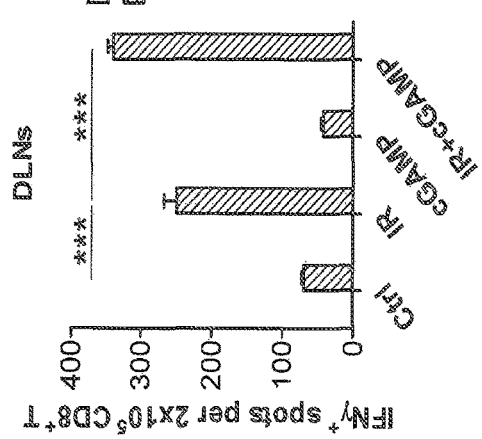

To further determine whether DCs are responsible for the type I IFN signaling after radiation, we implanted tumor cells into CD11c$^{Cre+}$-IFNAR1$^{f/f}$ mice and IFNAR1$^{f/f}$ mice. Conditional deletion of IFNAR1 on DCs hampered the antitumor effect of radiation (FIG. 20D), demonstrating that type I IFN signaling on DCs are responsible for antitumor effects of radiation. Next, we determined the CD8+ T cell response in DLNs of CD11c$^{Cre+}$-IFNAR1$^{f/f}$ mice and IFNAR1$^{f/f}$ mice following radiation. The CD8+ T cell function was remarkably compromised in DLNs of CD11c$^{Cre+}$-IFNAR1$^{f/f}$ mice versus IFNAR1$^{f/f}$ mice following radiation (FIG. 20E). These results indicate that type I IFN signaling on DCs is required for antitumor efficacy of radiation by boosting adaptive immune responses.

cGAMP Treatment and Radiation Synergistically Amplify the Antitumor Immune Responses It has been demonstrated that 2'3'-cGAMP (cyclic [G(2',5')pA(3',5')p]) is generated in mammalian cells by cGAS in response of double-stranded DNA in the cytoplasm. 2'3'-cGAMP is potent to activate innate immune responses by binding STING and subsequently inducing TBK1-IRF3-dependent IFN-β production (Gao et al., 2013a; Wu et al., 2013; Zhang et al., 2013). We hypothesized that exogenous 2'3'-cGAMP treatment improves the antitumor effect of radiation by enhancing STING activation. To test this hypothesis, 2'3'-cGAMP was intratumorally administrated after radiation at a dose of 10 µg administered to mice 6-8 weeks of age of approximately 25-35 g each. Treatment with a combination of 2'3'-cGAMP and radiation effectively reduce tumor burden compared to 2'3'-cGAMP or radiation alone in WT mice, suggesting cGAMP treatment can reduce tumor radiation resistance, a common cause of tumor relapse (FIGS. 21A and 21B). In contrast, the synergy of 2'3'-cGAMP and radiation was abrogated in STING$^{-/-}$ mice (FIGS. 21A and 21B). Together, these data indicate boosting the activation of STING signaling is able to remarkably inhibit tumor growth. To address whether the combination of 2'3'-cGAMP and radiation enhances tumor-specific T cell responses, ELISPOT assay were performed with isolated CD8+ T cells from DLNs, co-cultured with IFN-γ-treated MC38. The number of tumor-specific IFN-γ-producing CD8+ T cells was significantly increased in DLNs of mice that received combination treatment compared with those that received radiation or 2'3'-cGAMP alone (FIG. 21C). However, the robust antitumor CD8+ T cell response induced by the combination of 2'3'-cGAMP and radiation was dampened by the deficiency of STING in the host (FIG. 21D). Together, these results indicate that 2'3'-cGAMP treatment reduces radiation resistance by further enhancing tumor-specific CD8+ T cell functions and that the synergy is dependent on the presence of STING in the host, not in tumor cells.

Conclusions

Figure 22:
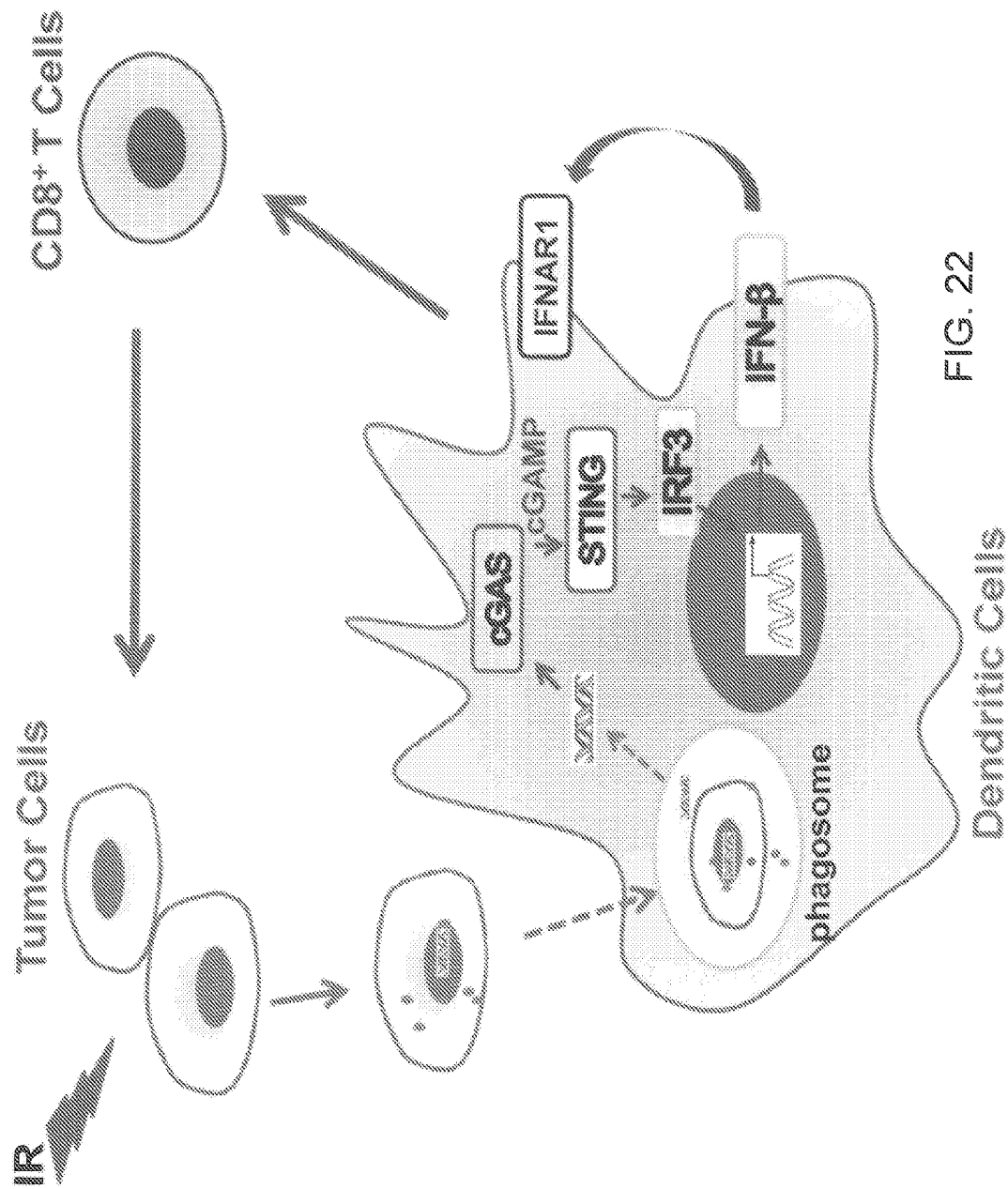
FIG. 22 shows schematic of proposed mechanism: cGAS-STING pathway is activated and orchestrates tumor immunity after radiation. Radiation results in the up-regulation of "find-me" and "eat-me" signals from tumor cells. During phagocytosis in dendritic cells, the DNA fragments hidden in irradiated-tumor cells are released from phagosomes to cytoplasm, acting as a danger signal. The cyclase cGAS binds tumor DNA, becomes catalytically active, and generate cGAMP as a second messenger. cGAMP binds to STING, which in turn activates IRF3 to induce type I IFN production. Type I IFN signaling on dendritic cells promotes the cross-priming of CD8$^+$ T cells, leading to tumor control. Exogenous cGAMP treatment could optimize antitumor immune responses of radiation.

Radiation has been demonstrated to induce adaptive immune responses to mediate tumor regression (Apetoh et al., 2007; Lee et al., 2009). The induction of type I IFNs by radiation is essential for the function of CD8+ T cells (Burnette et al., 2011). Although the importance of type I IFNs has been elucidated by utilizing the mice with whole body depletion of IFNAR1, which immune cells are responsible for type I IFN responses after radiation remained unsolved. More importantly, because the stimuli of type I IFN induction are diverse, discerning the mechanism responsible for type I IFN induction by radiation has been elusive. Various nucleic acid-sensing pathways from different subcellular compartments have been reported to play a critical role in inducing type I IFNs in response to pathogen infection and tissue injury (Desmet and Ishii, 2012; Wu and Chen, 2014). Indeed, radiation induces cell stress and causes excess DNA breaks, indicating that nucleic acid-sensing pathway likely account for the induction of type I IFNs upon radiation. We identify that cGAS-STING dependent-cytosolic DNA sensing pathway in DCs is required for type I IFN induction after radiation, and then the type I IFN signaling on DCs determines radiation-mediated adaptive immune responses. In addition, enhancing STING signaling by exogenous cGAMP treatment facilitates the antitumor effect of radiation. Therefore, our current study reveals that cGAS-STING-dependent cytosolic DNA sensing pathway is a key mediator of tumor immune responses to therapeutic radiation (See FIG. 22).

This study shows that type I IFN responses in DCs dictate the efficacy of antitumor radiation and proposed that HMGB-1 release by dying tumor cells and MyD88 signaling in the host are dispensable for radiation treatment. In contrast, chemotherapeutic agents and anti-HER2 antibody treatment have been demonstrated to depend on a distinct immune mechanism to trigger adaptive immune responses (Apetoh et al., 2007; Park et al., 2010). Anti-HER2 treatment and chemotherapy require HMGB-1 release from dying tumor cells, and TLR4 and its adaptor MyD88 on DCs. The interaction of HMGB-1 and TLR4 potentiates the processing of dying tumor cells by DCs, leading to efficient cross-priming of CD8+ T cells. However, antitumor effects of chemotherapy have been shown to depend on MyD88 signaling but not TLR4 (Iida et al., 2013). The inconsistencies are likely due to the treatment schedule including the tumor size of starting treatment and the dose of chemotherapeutic agent. Although MyD88 signaling has been shown to be necessary for the vaccination with irradiated-tumor cells, it is unanticipated that this signaling is dispensable in radiation treatment of established tumors. Nevertheless, our study demonstrates that the induction of type I IFNs by radiation depends on STING signaling, validating that a particular molecular mechanism mediates antitumor immune responses to radiation. Therefore, it is evident that therapeutic radiation-mediated antitumor immunity depends on a proper cytosolic DNA sensing pathway.

It has been shown that cGAS-STING sensing pathway is a key component in activating innate immune response to various DNA from pathogens, including virus, bacteria and parasites (Gao et al., 2013b; Lahaye et al., 2013; Li et al., 2013; Lippmann et al., 2011; Sharma et al., 2011). Also, cGAS-STING signaling pathway might play a dominant role in response to transfected DNA. Two groups have linked this signaling with DNA vaccines performed by intramuscular electroporation. One report found that TBK1 mediates antigen-specific B cell and T cell immune response after DNA vaccination through type I IFN induction (Ishii et al., 2008). Another report pointed out that STING is essential for DNA vaccine-induced adaptive immune responses (Ishikawa et al., 2009). However, whether DNA from dying cells acts as DAMPs to provoke immune responses remains unclear. The release of DNA from dying host cells has been shown to stimulate adaptive immune responses in the TBK1-IRF3-type I IFN-dependent manner, leading to alum adjuvant activity (Marichal et al., 2011). Specifically, oxidized self-DNA released from dying cells has been demonstrated to activate cGAS-STING-dependent cytosolic DNA sensing pathway as a mechanistic interpretation of UV-exposed skin lesions (Bernard et al., 2012). Our results uncover that cGAS-STING-dependent cytosolic DNA sensing pathway mediates the efficacy of therapeutic radiation. Moreover, cGAS-STING signaling is important for direct DCs sensing of irradiated-tumor cells as tested by an in vitro assay. It is likely that cytosol DNA from irradiated-tumor cells is a mediator to activate cGAS-STING signaling in DCs. Although DNA can be sensed by T cells and induce costimulatory responses, this process is independent on known DNA sensing pathways, including STING signaling (Imanishi et al., 2014). In addition, our result shows that DCs are major producer of type I IFNs following radiation. We propose that cGAS-STING signaling in DCs plays a key role in the sensing of irradiated-tumor cell DNA to induce subsequent tumor-specific $CD8^+$ T cell responses.

How DNA from irradiated-tumor cells is delivered into the cytosol of DCs remains unknown. DNA binding proteins such as LL37 are prevalent in neutrophil extracellular traps (NETs) and enhance cytoplasmic delivery of DNA (Diana et al., 2013; Lande et al., 2007). Indeed, several reports have shown that STING signaling is activated by DNA-LL37 complex (Chamilos et al., 2012; Gehrke et al., 2013). However, our results ruled out the possibility that DNA is delivered either by free floating form or by complex forms. Our data show that the direct cell-to-cell contact is required for the delivery of DNA from irradiated tumor cells, suggesting that phagocytosis mediates DNA delivery. Indeed, several groups have observed that phagosomal instability allows the content of this compartment to access to the cytosol, such as bacterial RNA (Sander et al., 2011). It is therefore possible that DNA from irradiated-tumor cells is delivered into the cytosol of DCs during membrane fusing process. Moreover, radiation is able to induce tumor cells and phagocytes to generate ROS, and then oxidated DNA modified by ROS is resistant to cytosolic exonuclease TREX-1-mediated degradation (Gehrke et al., 2013; Moeller et al., 2004). It is contemplated that radiation-induced ROS maintains the stability of tumor cell DNA during delivery into the cytosol of DCs. Therefore, we conclude that mapping out how tumor cell DNA traverses into the cytosol of DC will lead to further therapeutic targets using the present disclosure.

In summary, we demonstrate that the adaptor protein STING instead of MyD88 and TRIF provides for the antitumor effect of radiation and the induction of type I IFNs. The DNA sensor cGAS is important for DCs sensing of nucleic acids from irradiated-tumor cells. Moreover, cGAS-STING-IRF3-Type I IFNs cascade through autocrine action in DCs mediates robust adaptive immune responses to radiation. In addition, exogenous cGAMP treatment synergizes with radiation to control tumors. Therefore, our findings reveal a novel molecular mechanism of radiation-mediated antitumor immunity and highlight the potential to improve radiotherapy by cGAMP administration and/or by increasing the levels of cGAS in a cancerous cell.

REFERENCES

Ablasser, A., Schmid-Burgk, J. L., Hemmerling, I., Horvath, G. L., Schmidt, T., Latz, E., and Hornung, V. (2013). Cell intrinsic immunity spreads to bystander cells via the intercellular transfer of cGAMP. Nature 503, 530-534.

Ahn, J., Gutman, D., Saijo, S., and Barber, G. N. (2012). STING manifests self DNA-dependent inflammatory disease. Proc Natl Acad Sci USA 109, 19386-19391.

Apetoh, L., Ghiringhelli, F., Tesniere, A., Obeid, M., Ortiz, C., Criollo, A., Mignot, G., Maiuri, M. C., Ullrich, E., Saulnier, P., et al. (2007). Toll-like receptor 4-dependent contribution of the immune system to anticancer chemotherapy and radiotherapy. Nat Med 13, 1050-1059.

Begg, A. C., Stewart, F. A., and Vens, C. (2011). Strategies to improve radiotherapy with targeted drugs. Nat Rev Cancer 11, 239-253.

Bernard, J. J., Cowing-Zitron, C., Nakatsuji, T., Muehleisen, B., Muto, J., Borkowski, A. W., Martinez, L., Greidinger, E. L., Yu, B. D., and Gallo, R. L. (2012). Ultraviolet radiation damages self noncoding RNA and is detected by TLR3. Nat Med 18, 1286-1290.

Burdette, D. L., and Vance, R. E. (2013). STING and the innate immune response to nucleic acids in the cytosol. Nat Immunol 14, 19-26.

Burnette, B. C., Liang, H., Lee, Y., Chlewicki, L., Khodarev, N. N., Weichselbaum, R. R., Fu, Y. X., and Auh, S. L. (2011). The efficacy of radiotherapy relies upon induction of type i interferon-dependent innate and adaptive immunity. Cancer Res 71, 2488-2496.

Chamilos, G., Gregorio, J., Meller, S., Lande, R., Kontoyiannis, D. P., Modlin, R. L., and Gilliet, M. (2012). Cytosolic sensing of extracellular self-DNA transported into monocytes by the antimicrobial peptide LL37. Blood 120, 3699-3707.

Chen, G. Y., and Nunez, G. (2010). Sterile inflammation: sensing and reacting to damage. Nat Rev Immunol 10, 826-837.

Chen, H., Sun, H., You, F., Sun, W., Zhou, X., Chen, L., Yang, J., Wang, Y., Tang, H., Guan, Y., et al. (2011). Activation of STAT6 by STING is critical for antiviral innate immunity. Cell 147, 436-446.

Deng, L., Liang, H., Burnette, B., Beckett, M., Darga, T., Weichselbaum, R. R., and Fu, Y. X. (2014). Irradiation and anti-PD-L1 treatment synergistically promote antitumor immunity in mice. J Clin Invest 124, 687-695.

Desmet, C. J., and Ishii, K. J. (2012). Nucleic acid sensing at the interface between innate and adaptive immunity in vaccination. Nat Rev Immunol 12, 479-491.

Diana, J., Simoni, Y., Furio, L., Beaudoin, L., Agerberth, B., Barrat, F., and Lehuen, A. (2013). Crosstalk between neutrophils, B-1a cells and plasmacytoid dendritic cells initiates autoimmune diabetes. Nat Med 19, 65-73.

Gall, A., Treuting, P., Elkon, K. B., Loo, Y. M., Gale, M., Jr., Barber, G. N., and Stetson, D. B. (2012). Autoimmunity initiates in nonhematopoietic cells and progresses via lymphocytes in an interferon-dependent autoimmune disease. Immunity 36, 120-131.

Gao, P., Ascano, M., Wu, Y., Barchet, W., Gaffney, B. L., Zillinger, T., Serganov, A. A., Liu, Y., Jones, R. A., Hartmann, G., et al. (2013a). Cyclic [G(2',5')pA(3',5')p] is the metazoan second messenger produced by DNA-activated cyclic GMP-AMP synthase. Cell 153, 1094-1107.

Gao, P., Ascano, M., Zillinger, T., Wang, W., Dai, P., Serganov, A. A., Gaffney, B. L., Shuman, S., Jones, R. A., Deng, L., et al. (2013b). Structure-function analysis of STING activation by c[G(2',5')pA(3',5')p] and targeting by antiviral DMXAA. Cell 154, 748-762.

Gehrke, N., Mertens, C., Zillinger, T., Wenzel, J., Bald, T., Zahn, S., Tuting, T., Hartmann, G., and Barchet, W. (2013). Oxidative damage of DNA confers resistance to cytosolic nuclease TREX1 degradation and potentiates STING-dependent immune sensing. Immunity 39, 482-495.

Holm, C. K., Jensen, S. B., Jakobsen, M. R., Cheshenko, N., Horan, K. A., Moeller, H. B., Gonzalez-Dosal, R., Rasmussen, S. B., Christensen, M. H., Yarovinsky, T. O., et al. (2012). Virus-cell fusion as a trigger of innate immunity dependent on the adaptor STING. Nat Immunol 13, 737-743.

Iida, N., Dzutsev, A., Stewart, C. A., Smith, L., Bouladoux, N., Weingarten, R. A., Molina, D. A., Salcedo, R., Back, T., Cramer, S., et al. (2013). Commensal bacteria control cancer response to therapy by modulating the tumor microenvironment. Science 342, 967-970.

Imanishi, T., Ishihara, C., Badr Mel, S., Hashimoto-Tane, A., Kimura, Y., Kawai, T., Takeuchi, O., Ishii, K. J., Taniguchi, S., Noda, T., et al. (2014). Nucleic acid sensing by T cells initiates Th2 cell differentiation. Nat Commun 5, 3566.

Ishii, K. J., Kawagoe, T., Koyama, S., Matsui, K., Kumar, H., Kawai, T., Uematsu, S., Takeuchi, O., Takeshita, F., Coban, C., and Akira, S. (2008). TANK-binding kinase-1 delineates innate and adaptive immune responses to DNA vaccines. Nature 451, 725-729.

Ishikawa, H., and Barber, G. N. (2008). STING is an endoplasmic reticulum adaptor that facilitates innate immune signalling. Nature 455, 674-678.

Ishikawa, H., Ma, Z., and Barber, G. N. (2009). STING regulates intracellular DNA-mediated, type I interferon-dependent innate immunity. Nature 461, 788-792.

Kono, H., and Rock, K. L. (2008). How dying cells alert the immune system to danger. Nat Rev Immunol 8, 279-289.

Lahaye, X., Satoh, T., Gentili, M., Cerboni, S., Conrad, C., Hurbain, I., El Marjou, A., Lacabaratz, C., Lelievre, J. D., and Manel, N. (2013). The capsids of HIV-1 and HIV-2 determine immune detection of the viral cDNA by the innate sensor cGAS in dendritic cells. Immunity 39, 1132-1142.

Lande, R., Gregorio, J., Facchinetti, V., Chatterjee, B., Wang, Y. H., Homey, B., Cao, W., Su, B., Nestle, F. O., Zal, T., et al. (2007). Plasmacytoid dendritic cells sense self-DNA coupled with antimicrobial peptide. Nature 449, 564-569.

Lee, Y., Auh, S. L., Wang, Y., Burnette, B., Meng, Y., Beckett, M., Sharma, R., Chin, R., Tu, T., Weichselbaum, R. R., and Fu, Y. X. (2009). Therapeutic effects of ablative radiation on local tumor require CD8$^+$ T cells: changing strategies for cancer treatment. Blood 114, 589-595.

Li, X. D., Wu, J., Gao, D., Wang, H., Sun, L., and Chen, Z. J. (2013). Pivotal roles of cGAS-cGAMP signaling in antiviral defense and immune adjuvant effects. Science 341, 1390-1394.

Liang, H., Deng, L., Chmura, S., Burnette, B., Liadis, N., Darga, T., Beckett, M. A., Lingen, M. W., Witt, M., Weichselbaum, R. R., and Fu, Y. X. (2013). Radiation-induced equilibrium is a balance between tumor cell proliferation and T cell-mediated killing. J Immunol 190, 5874-5881.

Liauw, S. L., Connell, P. P., and Weichselbaum, R. R. (2013). New paradigms and future challenges in radiation oncology: an update of biological targets and technology. Sci Transl Med 5, 173sr172.

Lippmann, J., Muller, H. C., Naujoks, J., Tabeling, C., Shin, S., Witzenrath, M., Hellwig, K., Kirschning, C. J., Taylor, G. A., Barchet, W., et al. (2011). Dissection of a type I interferon pathway in controlling bacterial intracellular infection in mice. Cell Microbiol 13, 1668-1682.

Marichal, T., Ohata, K., Bedoret, D., Mesnil, C., Sabatel, C., Kobiyama, K., Lekeux, P., Coban, C., Akira, S., Ishii, K. J., et al. (2011). DNA released from dying host cells mediates aluminum adjuvant activity. Nat Med 17, 996-1002.

Moeller, B. J., Cao, Y., Li, C. Y., and Dewhirst, M. W. (2004). Radiation activates HIF-1 to regulate vascular radiosensitivity in tumors: role of reoxygenation, free radicals, and stress granules. Cancer Cell 5, 429-441.

O'Neill, L. A., Golenbock, D., and Bowie, A. G. (2013). The history of Toll-like receptors—redefining innate immunity. Nat Rev Immunol 13, 453-460.

Paludan, S. R., and Bowie, A. G. (2013). Immune sensing of DNA. Immunity 38, 870-880.

Park, S., Jiang, Z., Mortenson, E. D., Deng, L., Radkevich-Brown, O., Yang, X., Sattar, H., Wang, Y., Brown, N. K., Greene, M., et al. (2010). The therapeutic effect of anti-HER2/neu antibody depends on both innate and adaptive immunity. Cancer Cell 18, 160-170.

Postow, M. A., Callahan, M. K., Barker, C. A., Yamada, Y., Yuan, J., Kitano, S., Mu, Z., Rasalan, T., Adamow, M., Ritter, E., et al. (2012). Immunologic correlates of the abscopal effect in a patient with melanoma. N Engl J Med 366, 925-931.

Sander, L. E., Davis, M. J., Boekschoten, M. V., Amsen, D., Dascher, C. C., Ryffel, B., Swanson, J. A., Muller, M., and Blander, J. M. (2011). Detection of prokaryotic mRNA signifies microbial viability and promotes immunity. Nature 474, 385-389.

Sharma, S., DeOliveira, R. B., Kalantari, P., Parroche, P., Goutagny, N., Jiang, Z., Chan, J., Bartholomeu, D. C., Lauw, F., Hall, J. P., et al. (2011). Innate immune recognition of an AT-rich stem-loop DNA motif in the *Plasmodium falciparum* genome. Immunity 35, 194-207.

Stagg, J., Loi, S., Divisekera, U., Ngiow, S. F., Duret, H., Yagita, H., Teng, M. W., and Smyth, M. J. (2011). Anti-ErbB-2 mAb therapy requires type I and II interferons and synergizes with anti-PD-1 or anti-CD137 mAb therapy. Proc Natl Acad Sci USA 108, 7142-7147.

Takeuchi, O., and Akira, S. (2010). Pattern recognition receptors and inflammation. Cell 140, 805-820.

Wu, J., and Chen, Z. J. (2014). Innate immune sensing and signaling of cytosolic nucleic acids. Annu Rev Immunol 32, 461-488.

Wu, J., Sun, L., Chen, X., Du, F., Shi, H., Chen, C., and Chen, Z. J. (2013). Cyclic GMP-AMP is an endogenous second messenger in innate immune signaling by cytosolic DNA. Science 339, 826-830.

Zhang, X., Shi, H., Wu, J., Sun, L., Chen, C., and Chen, Z. J. (2013). Cyclic GMP-AMP containing mixed phosphodiester linkages is an endogenous high-affinity ligand for STING. Mol Cell 51, 226-235.

The invention has been described in an illustrative manner and it is to be understood the terminology used is intended to be in the nature of description rather than of limitation. All patents and other references cited herein are incorporated herein by reference in their entirety. It is also understood that many modifications, equivalents, and variations of the present invention are possible in light of the above teachings. Therefore, it is to be understood that within the scope of the appended claims, the invention may be practiced other than as specifically described.

We claim:

1. A method of treating cancer in a subject in need thereof, comprising:
regulating endogenous Type I Interferon production in the subject by maintaining a therapeutically effective amount of activation of Type I Interferon and/or inducing Type I interferon production in the subject by administering to the subject a therapeutic amount of an agent to enhance STING signaling in the subject; and administering to the subject a therapeutic amount of ionizing radiation,
wherein the agent comprises one or more of cGAS mRNA, combretastatin A-1, combretastatin B1, CAS 181816-48, and cGAMP.

2. The method of claim 1, further comprising suppressing the product or the expression of an Interferon-Stimulated Gene (ISG).

3. The method of claim 2, wherein the ISG comprises at least one RIG1-like receptor (RLR) family member.

4. The method of claim 3, wherein ionizing radiation induced Type I Interferon production is substantially maintained in the subject at levels substantially found prior to the administration of the therapeutic amount of ionizing radiation.

5. The method of claim 4, wherein Mitochondrial Antiviral Signaling Protein (MAVS)-dependent induction of endogenous Type I Interferon production is maintained in the subject at substantially the same level found in the subject prior to the administration of the ionizing radiation.

6. The method of claim 3, wherein the RIG1-like receptor (RLR) family member comprises LGP2 (Laboratory of Genetics and Physiology 2).

7. The method of claim 2, wherein the suppression of the product or the expression of the ISG results in at least one of suppression of growth or proliferation of the cancer, cell death of the cancer, or sensitization of the cancer to the ionizing radiation and/or chemotherapy.

8. The method of claim 2, wherein the suppression of the product of the ISG comprises suppression of expression of at least one Cytoplasmic Pattern-recognition Receptor (PRR) protein.

9. The method of claim 8, wherein the at least one PRR protein comprises at least one of LGP2 and MDA5.

10. The method of claim 1, wherein the method maintains ionizing radiation and chemotherapy sensitization in the subject.

11. The method of claim 1 further comprising down-regulating cytoplasmic DNA-sensing pathway-exonuclease TREX1 (Three Prime Repair Exonuclease 1).

12. The method of claim 1 further comprising up-regulating at least one of DAI (DNA-dependent Activator of IFN regulatory factors), IFI16 (Gamma-interferon-inducible protein Ifi-16), and Aim2 (Interferon-inducible protein AIM2).

13. The method of claim 1, wherein the ionizing radiation comprises at least one of brachytherapy, external beam radiation therapy, or radiation from cesium, iridium, iodine, or cobalt.

14. The method of claim 1, wherein the agent is delivered by a pharmaceutical carrier.

15. The method of 30, wherein the pharmaceutical carrier comprises at least one of a nanocarrier, a conjugate, a nucleic-acid-lipid particle, a vesicle, an exosome, a protein capsid, a liposome, a dendrimer, a lipoplex, a micelle, a virosome, a virus like particle, and a nucleic acid complex.

16. The method of claim 15, wherein the agent is delivered into a cytosol of a dendritic cell.

17. The method of claim 1, wherein the agent further comprises one or more of a DNA damaging agent and DNA from irradiated tumor cells.

18. The method of claim 1, wherein the agent comprises cGAMP.

* * * * *

```
                             SEQUENCE LISTING

<160> NUMBER OF SEQ ID NOS: 14

<210> SEQ ID NO 1
<211> LENGTH: 18
<212> TYPE: RNA
<213> ORGANISM: Artificial Sequence
<220> FEATURE:
<223> OTHER INFORMATION: Dharmacon siGENOME

<400> SEQUENCE: 1
ccaguaccua gaacuuaa                                                        18

<210> SEQ ID NO 2
<211> LENGTH: 19
<212> TYPE: RNA
<213> ORGANISM: Artificial Sequence
<220> FEATURE:
<223> OTHER INFORMATION: Dharmacon siGENOME

<400> SEQUENCE: 2
agaaugagcu ggcccacuu                                                       19

<210> SEQ ID NO 3
<211> LENGTH: 21
<212> TYPE: DNA
<213> ORGANISM: Artificial Sequence
<220> FEATURE:
<223> OTHER INFORMATION: LGP2 shRNA sequence

<400> SEQUENCE: 3
attcttgcgg tcatcgaaca g                                                    21

<210> SEQ ID NO 4
<211> LENGTH: 24
<212> TYPE: DNA
<213> ORGANISM: Artificial Sequence
<220> FEATURE:
<223> OTHER INFORMATION: human gene-specific primers, IFN  sense primer

<400> SEQUENCE: 4
aactttgaca tccctgagga gatt                                                 24

<210> SEQ ID NO 5
<211> LENGTH: 17
<212> TYPE: DNA
<213> ORGANISM: Artificial Sequence
<220> FEATURE:
<223> OTHER INFORMATION: human gene-specific primers, IFN antisense
      primer

<400> SEQUENCE: 5
gcggcgtcct ccttctg                                                         17

<210> SEQ ID NO 6
<211> LENGTH: 20
<212> TYPE: DNA
<213> ORGANISM: Artificial Sequence
<220> FEATURE:
<223> OTHER INFORMATION: human gene-specific primer, GAPDH sense

<400> SEQUENCE: 6
```
ctctgctcct cctgttcgac                                          20

<210> SEQ ID NO 7
<211> LENGTH: 20
<212> TYPE: DNA
<213> ORGANISM: Artificial Sequence
<220> FEATURE:
<223> OTHER INFORMATION: human gene-specific primer, GAPDH antisense

<400> SEQUENCE: 7
gttaaaagca gccctggtga                                          20

<210> SEQ ID NO 8
<211> LENGTH: 23
<212> TYPE: DNA
<213> ORGANISM: Artificial Sequence
<220> FEATURE:
<223> OTHER INFORMATION: mmcGAS

<400> SEQUENCE: 8
gaggaaaucc gcugagucad tdt                                      23

<210> SEQ ID NO 9
<211> LENGTH: 21
<212> TYPE: DNA
<213> ORGANISM: Artificial Sequence
<220> FEATURE:
<223> OTHER INFORMATION: mIFN- beta forward

<400> SEQUENCE: 9
ggtggaatga gactattgtt g                                        21

<210> SEQ ID NO 10
<211> LENGTH: 18
<212> TYPE: DNA
<213> ORGANISM: Artificial Sequence
<220> FEATURE:
<223> OTHER INFORMATION: mIFN-beta reverse

<400> SEQUENCE: 10
aagtggagag cagttgag                                            18

<210> SEQ ID NO 11
<211> LENGTH: 24
<212> TYPE: DNA
<213> ORGANISM: Artificial Sequence
<220> FEATURE:
<223> OTHER INFORMATION: m-cGAS forward

<400> SEQUENCE: 11
accggacaag ctaaagaagg tgct                                     24

<210> SEQ ID NO 12
<211> LENGTH: 24
<212> TYPE: DNA
<213> ORGANISM: Artificial Sequence
<220> FEATURE:
<223> OTHER INFORMATION: m-cGAS reverse

<400> SEQUENCE: 12
gcagcaggcg ttccacaact ttat                                     24

<210> SEQ ID NO 13
<211> LENGTH: 21
<212> TYPE: DNA

```
<213> ORGANISM: Artificial Sequence
<220> FEATURE:
<223> OTHER INFORMATION: 18S forward

<400> SEQUENCE: 13
cgtctgccct atcaactttc g                                               21

<210> SEQ ID NO 14
<211> LENGTH: 20
<212> TYPE: DNA
<213> ORGANISM: Artificial Sequence
<220> FEATURE:
<223> OTHER INFORMATION: 18S reverse

<400> SEQUENCE: 14
tgccttcctt ggatgtggta                                                 20
```